United States Patent [19]
Igarashi et al.

[11] Patent Number: 5,627,204
[45] Date of Patent: May 6, 1997

[54] CHROMONE DERIVATIVE, AND ALDOSE REDUCTASE INHIBITOR COMPRISING SAID COMPOUND AS ACTIVE COMPONENT

[75] Inventors: Yasushi Igarashi; Takuji Yamaguchi; Yoshimitsu Ogawa; Mika Tomita; Hiroko Hayashi; Toshitsugu Sato; Kunio Hosaka, all of Ibaraki-ken, Japan

[73] Assignee: Tsumura & Company, Tokyo, Japan

[21] Appl. No.: 465,950

[22] Filed: Jun. 6, 1995

Related U.S. Application Data

[62] Division of Ser. No. 322,396, Oct. 12, 1994, Pat. No. 5,455,267, which is a continuation of Ser. No. 915,995, Jul. 30, 1992, abandoned.

[30] Foreign Application Priority Data

Nov. 30, 1990 [JP] Japan .................. 2-330519
Nov. 30, 1990 [JP] Japan .................. 2-330520

[51] Int. Cl.$^6$ .............. A61K 31/355; A61K 31/495; A61K 31/44; A61K 31/415
[52] U.S. Cl. .............. 514/456; 514/367; 514/363; 514/362; 514/337; 514/253
[58] Field of Search ................ 549/400, 401, 549/214; 514/456, 367, 363, 362, 337, 253; 548/324, 159, 128, 127; 544/376

[56] References Cited

U.S. PATENT DOCUMENTS 4,532,254  7/1985  Okuda et al. .................. 514/456

FOREIGN PATENT DOCUMENTS

| | | | |
|---|---|---|---|
| 54-114768 | 9/1979 | Japan . | |
| 58-99414 | 6/1983 | Japan .................. | A61K 31/35 |
| 63-104920 | 5/1988 | Japan .................. | A61K 31/35 |
| 1-228914 | 9/1989 | Japan . | |
| 2-169586 | 6/1990 | Japan . | |

OTHER PUBLICATIONS

Tanimoto, Tsuyoshi (1988) Pharmacie 24:459.
Sato et al. Inhibition of Aldehyde Reductase by Aldose Reductase Inhibitors (1990) Biochemical Pharmacology, 40:1033–1042.
Komiya et al. Studies on "Inchinko," Studies on the Compounds related to Capillarisin and Flavonoids, (1979) J. of Pharm. Soc. of Japan 96:855.
Komiya et al (1979) J. of Pharm. Soc. of Japan 96:841.
Komiya et al., Yakugaku Zasshi (1976) 96:7 855–862.
Journal of the Pharmaceutical Society of Japan, Jul. 1976, vo. 96, No. 7, pp. 841–862.
Chemical Abstracts, vol. III, 1989, p. 60, column 1. US Abstract No. 90199j, "Aldose Reductase Inhibitors of Inchinko".
Peter F. Kador, Norman B. Sharpless, Biophysical Chemistry, vol. 8, No. 1, Mar. 1978, pp. 81–85, "Structure–Activity Studies of Aldose Reductase Inhibitors Containing the 4–OXO–4H Chromen Ring System".
A. Laurens et al. Therapeutique, vol. 38, No. 6, 1983, pp. 659–663 "Les Inhibitors De L'Aldose Reductase ".
Sarges, et al., Spiro Hydantoin Aldose Reductase Inhibitors (1988) J. Med. Chemn 31:230–243.
Wrobel, et al., Orally Active Aldose Reductase Inhibitors from Bioisosteric Substitutions on Tolrestat (1989) J. Med. Chem 32:2493–2500.
Patent Abstracts of Japan, English language abstract of JP 2–169586, 1990.
Chemical Abstract vol. 86, 1987, p.420, col. 1, No. 86–55239r "Studies on 'Inchinko', ".

*Primary Examiner*—Nicky Chan
*Attorney, Agent, or Firm*—Limbach & Limbach L.L.P.

[57] ABSTRACT

The present invention relates to a chromone derivative and an aldose reductase inhibitor comprising said compound as efective component, which is represented by the following formula:

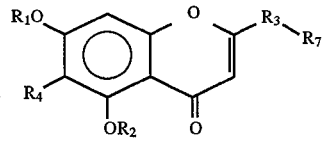

wherein $R_1$ and $R_2$ each represent a lower alkyl group, etc., $R_3$ represents an oxygen atom, a sulfur atom, etc., $R_7$ represents a phenyl group substituted or not substituted, etc., and R represents a hydrogen atom or a lower alkoxy group. The present compounds exhibit superior inhititory action on aldose reductase and are useful for the treatment of various complications of diseases in diabetes, such as cataract, retinopathy, keratopathy, nephropathy, and neuropathy.

16 Claims, No Drawings

CHROMONE DERIVATIVE, AND ALDOSE REDUCTASE INHIBITOR COMPRISING SAID COMPOUND AS ACTIVE COMPONENT

This is a divisional of application Ser. No. 08/322,396, filed Oct. 12, 1994, now U.S. Pat. No. 5,455,267, which was a file wrapper continuation of application Ser. No. 07/915,995 filed Jul. 30, 1992, now abandoned.

TECHNICAL FIELD

The present invention relates to chromone derivatives with the inhibitory action on aldose reductase which are effective for the treatment of a complication due to diabetes, as well as to utilities thereof.

TECHNICAL BACKGROUND

In recent years, attention is drawn to the accumulation of sorbitol in cells via a polyol pathway, i.e. a metabolic pathway of glucose, as a causative factor of various of a complication in diabetes of cataract, retinopathy, keratopathy, nephrosis, and neuropathy. This polyol pathway is the metabolic pathway of converting aldoses e.g. glucose, galactose, etc., through polyols e.g. sorbitol, galactitol, etc., into ketoses e.g. fructose, etc. According to immunotissue-chemical techniques, this pathway was proved to occur widely in various tissues.

The enzyme catalyzing conversion between aldoses and polyols (i.e. the first step of this pathway) is called aldose reductase, and this enzyme is considered the rate-limiting enzyme in the polyol pathway. It has been reported that various complications in patients with diabetes are effectively prevented and cured by inhibiting of aldose reductase and lowering the production and accumulation of sorbitol (Pharmacia, 24:459 (1988)).

Under the circumstances, it has been desired to develop pharmaceuticals with the inhibitory action on aldose reductase.

As pharmaceuticals with the inhibitory action on aldose reductase, Japanese Patent Appln. LOP Publication No. 228914/1989 discloses chromone derivatives, Capillarisin (R=H) and 7-methyl Capillarisin (R=$CH_3$), which having been isolated from the herb of Artemisia capillaris thunb and are represented by Formula:

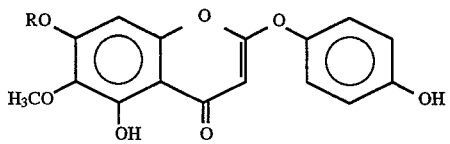

Among prior art compounds similar in structure to Capillarisin, chromone derivatives, which are represented by Formula (A):

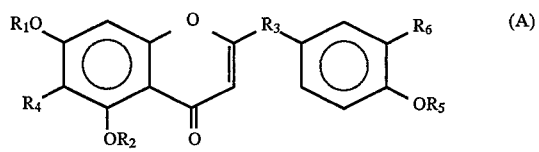

wherein $R_1$, $R_2$, $R_3$, $R_4$, $R_5$, and $R_6$ are set forth in Table 2, belong to the prior art (for example, Japanese Patent Appln. LOP Publications Nos. 169586/1990, 39085/1981 and 322066/88 and Journal of the Pharmaceutical Society of Japan, 96: 841(1926) and 96: 855 (1976)). However, no reports have revealed whether the chromone derivatives exhibit the inhibitory action on aldose reductase.

TABLE 2

| $R_1$ | $R_2$ | $R_3$ | $R_4$ | $R_5$ | $R_6$ |
|---|---|---|---|---|---|
| $CH_3$ | H | O | $OCH_3$ | H | H |
| $CH_3$ | H | O | $OCH_3$ | $CH_3$ | H |
| $CH_3$ | $CH_3$ | O | $OCH_3$ | $CH_3$ | H |
| $C_2H_5$ | H | O | $OCH_3$ | $C_2H_5$ | H |
| $C_2H_5$ | $C_2H_5$ | O | $OCH_3$ | $C_2H_5$ | H |
| $COCH_3$ | $COCH_3$ | O | $OCH_3$ | $COCH_3$ | H |
| H | H | S | $OCH_3$ | H | H |
| H | $CH_3$ | O | H | H | H |
| $CH_3$ | $CH_3$ | O | H | $CH_3$ | H |
| $CH_3$ | H | O | H | H | H |
| H | H | O | H | H | H |
| H | H | O | H | $CH_3$ | H |
| $CH_3$ | H | O | H | $CH_3$ | H |

DISCLOSURE OF THE INVENTION

As a result of extensive researches, the present inventors have found that specific known compounds or novel compounds prepared by chemical modification of Capillarisin are superior to Capillarisin in respect of the inhibitory action on aldose reductase. That is, the present invention relates primarily to an aldose reductase inhibitor comprising as active components chromone derivatives or pharmacologically acceptable salts thereof, which are represented by Formula (I):

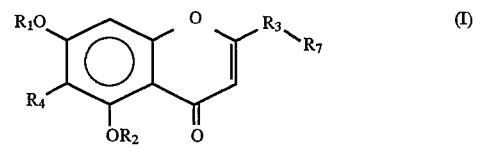

wherein $R_1$ and $R_2$ are the same or different and each represent a hydrogen atom, a lower alkyl group, a lower akenyl group, or an acyl group; $R_3$ represents an oxygen atom, a sulfur atom, —SO—, —$SO_2$—, or —NH—; $R_7$ represents a phenyl, aralkyl, or heterocyclic group substituted or not substituted; and $R_4$ represents a hydrogen atom or a lower alkoxy group, said derivatives excluding compounds represented by the following formula:

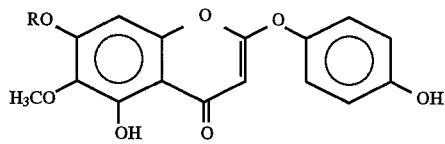

wherein R represents a hydrogen atom or a methyl group.

Compounds represented by Formula (I) other than those represented by Formula (A):

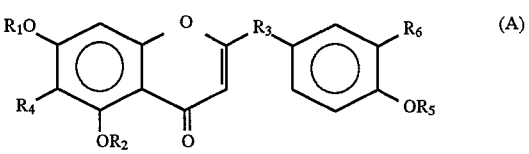

wherein $R_1$, $R_2$, $R_3$, $R_4$, $R_5$, and $R_6$ are set forth in Table 1, are novel compounds, and the present invention relates to these novel compounds.

TABLE 1

| $R_1$ | $R_2$ | $R_3$ | $R_4$ | $R_5$ | $R_6$ |
|---|---|---|---|---|---|
| H | H | O | OCH$_3$ | H | H |
| CH$_3$ | H | O | OCH$_3$ | H | H |
| CH$_3$ | H | O | OCH$_3$ | CH$_3$ | H |
| CH$_3$ | CH$_3$ | O | OCH$_3$ | CH$_3$ | H |
| C$_2$H$_5$ | H | O | OCH$_3$ | C$_2$H$_5$ | H |
| C$_2$H$_5$ | C$_2$H$_5$ | O | OCH$_3$ | C$_2$H$_5$ | H |
| COCH$_3$ | COCH$_3$ | O | OCH$_3$ | COCH$_3$ | H |
| H | H | S | OCH$_3$ | H | H |
| H | CH$_3$ | O | H | H | H |
| CH$_3$ | CH$_3$ | O | H | CH$_3$ | H |
| CH$_3$ | H | O | H | H | H |
| H | H | O | H | H | H |
| H | H | O | H | CH$_3$ | H |
| CH$_3$ | H | O | H | CH$_3$ | H |

In Formula (I) above, the lower alkyl group represented by $R_1$ or $R_2$ includes a $C_{1-6}$ alkyl group, such as a methyl, ethyl, propyl, isopropyl, butyl, isobutyl, sec-butyl, tert-butyl, pentyl, isopentyl, 1-ethylpropyl, or hexyl group.

The lower alkenyl group represented by $R_1$ or $R_2$ includes a $C_{2-6}$ alkenyl group, such as a vinyl, allyl, or prenyl group.

The acyl group represented by $R_1$ or $R_2$ includes an aliphatic acyl group, such as an acetyl or acryloyl group and an aromatic acyl group, such as a benzoyl group.

$R_7$ stands for an aralkyl group, such as a benzyl group, and a heterocyclic group, preferably a nitrogen-containing heterocyclic group, such as a pyridyl, benzimidazolyl, benzthiazolyl, thiazolynyl, or thiadiazolyl group.

The phenyl, aralkyl, or heterocyclic group represented by $R_7$ may be substituted by a suitable substituent group, which is preferably a $C_{1-6}$ alkyl group, a halogen atom, an amino, hydroxy, nitro, carboxyl, hydroxymethyl, methylenedioxy, $C_{1-6}$ alkoxy, $C_{1-6}$ alkenyloxy, $C_{1-6}$ alkoxycarbonyl, tert-butyldimethylsilyloxy, amino acid-derived acyloxy, or substituted or unsubstituted benzoyloxy group.

The lower alkoxy group represented by $R_4$ includes a $C_{1-6}$ alkoxy group, such as a methoxy, ethoxy, propoxy, or isopropoxy group. In respect of the inhibitory action on aldose reductase, the following groups are preferred: i.e. $R_1$ represents an ethyl group or a branched alkyl group represented by Formula (II):

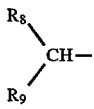

(II)

wherein $R_8$ and $R_9$ are the same or different and each represent a methyl or ethyl group, and $R_2$ is a hydrogen atom, a methy or ethyl group, or a branched alkyl group of Formula (II) above.

$R_3$ is preferably a sulfur atom or —SO—, particularly preferably a sulfur atom; $R_4$ is, preferably, a lower alkoxy group for inhibition of aldose reductase and a hydrogen atom for easiness of synthesis.

Examples of compounds preferred for the inhibition of aldose reductase include: 5,7-diisopropoxy-2-(4-hydroxyphenylthio)-6-methoxychromone, 5,7-diethoxy-2-(4-hydroxyphenylthio)-6-methoxychromone, 5,7-di-s-butoxy-2-(4-hydroxyphenylthio)-6-methoxychromone, 7-s-butoxy-2-(4-hydroxyphenylthio)-5-isopropoxy-6-methoxychromone, 5-ethoxy-2-(4-hydroxyphenylthio)-7-isopropoxy-6-methoxychromone, 5-hydroxy-2-(4-hydroxyphenylthio)-7-isopropoxy-6-methoxychromone, 5,6-dimethoxy-2-(4-hydroxyphenylthio)-7-isopropoxychromone, 7-s-butoxy-5,6-dimethoxy-2-(4-hydroxyphenylthio)chromone, 5,6-dimethoxy-7-(1-ethylpropoxy)-2-(4-hydroxyphenylthio)chromone, and 5,7-diisopropoxy-2-(4-hydroxyphenylthio)chromone.

Compounds represented by Formula (I) above, in which $R_7$ represents a phenyl group substituted by a glycyloxy group, —OC(=O)—CH$_2$CH(NH$_2$)COOH, or a 4-(4-methylpiperazinomethyl)benzoyloxy group can be converted into pharmacologically acceptable acid addition salts. Such acid addition salts are superior in respect of solubility in water. Examples are 5,6-dimethoxy-2-(4-glycyloxyphenylthio)-7-isopropoxychromone hydrochloride, 5-ethoxy-2-(4-glycyloxyphenylthio)-7-isopropoxy-6-methoxychromone hydrochloride, 7-(1-ethylpropoxy)-5,6-dimethoxy-2-(4-glycyloxyphenylthio)chlormone hydrochloride, 2-(4-β-asparthyloxyphenylthio)-5-ethoxy-7-isopropoxy-6-methoxychromone hydrochloride, 5,6-dimethoxy-7-(1-ethylpropoxy)-2-{4-[4-(4-methylpiperazinomethyl)benzoyloxy]phenylthio}chromone dihydrochloride, and 7-(1-ethylpropoxy)-5-hydroxy-2-{4-[4-(4-methylpiperazinomethyl)benzoyloxy]phenylthio}-6-methoxychromone dihydrochloride.

Compounds of Formula (I) above, in which $R_3$ represents an oxygen atom, exhibit as such the inhibitory action on aldose reductase and are thus useful as the present inhibitory agents of aldose reductase, and said compounds are also useful as synthetic intermediates of compounds of Formula (I) wherein $R_3$ represents a sulfur atom, —SO—, —SO$_2$—, or —NH—.

The present compounds of Formula (I) can be converted into pharmacologically acceptable salts. Such salts are preferably chlorides, phosphates, sulfates, fumarates, maleates, or acetates.

The present compounds can be prepared e.g. according to the following method.

That is, in a solvent e.g. acetone, etc., Capillarisin is methylated using dimethylsulfuric acid or alkylated using alkyl halide, and in the case of the preparation of a compound of Formula (I) above in which $R_3$ stands for a sulfur atom, the product is further reacted with benzenethiol in the presence of a base, so that the present compound can be prepared.

The present compounds can also be prepared as follows: at least one of hydroxy groups at the 2'-, 4'-, and 6'-positions in commercial floroacetophenone is alkylated, followed by reaction with potassium t-butoxide and carbon disulfide, thereby giving a thion compound. Then, in the presence of a base, this product is reacted with 4-methoxybenzyl chloride or methylated, thereby giving sulfide. Subsequently, this sulfide is oxidized to give sulfoxide (referred to as "Intermediate (I)", hereinafter), which in turn is substituted by benzenethiol or p-hydroquinone in the presence of a base, whereby the present compounds can also be prepared.

Examples of alkyl halide include alkyl iodide, such as methyl iodide, ethyl iodide, propyl iodide, isopropyl iodide, butyl iodide, isobutyl iodide, and s-butyl iodide and alkyl bromide, such as methyl bromide, ethyl bromide, etc.

In alkylation, it is preferred to use a base such as potassium carbonate etc. The reaction can be effected at room temperature. In consideration of reaction efficiency, etc., the reaction may be conducted under heating at approx. 50°–60° C. and if necessary under reflux, etc.

Benzenethiols used for substitution reaction may be commercial ones, e.g. benzenethiol, 2-chlorobenzenethiol, 3-chlorobenzenethiol, 4-chlorobenzenethiol, 4-nitrobenzenethiol, 2-methoxybenzenethiol, 3-methoxybenezenethiol, 4-methoxybenzenethiol, 2-aminobenzenethiol, 3-aminobenzenethiol, 4-aminobenzenethiol, 2-methylbenzenethiol, 3-methylbenzenethiol, 4-benzenethiol, 2-hydroxybenzenethiol, 3-hydroxybenzenethiol, 4-hydroxybenzenethiol, 4-hydroxybenzenethiol, 4-hydroxy-3,5-di-t-butylbenzenethiol. Potassium carbonate is preferably used as a base.

Other examples of benzenethiols are 4-mercaptobenzoic acid, methyl 4-mercaptobenzoate, 4-mercaptobenzylalcohol, 3,4-methylenedioxybenzenethiol, 3,4-dihydroxybenzenethiol, and these thiols can be prepared as follows: after diazotization of 4-aminobenzoic acid, 3,4-methylenedioxyaniline, or 3,4-dimethoxyaniline, the resulting sulfide is reduced (or methylated and then reduced) by sodium borohydride in an aqueous solution of sodium hydroxide or reduced by lithium aluminium hydride or, if necessary, demethylated using boron tribromide, etc.

Purification of the product comprises customarily used methods e.g. column chromatography using a carrier such as silica gel etc. and recrystallization from methanol, ethanol, chloroform, dimethylsulfoxide, water, etc. Eluting solvent in column chromatography includes chloroform, acetone, hexane, dichloromethane, and ethyl acetate.

The following is the example for the preparation of Intermediate (1).

EXAMPLE 336.0 g of potassium t-butoxide was suspended in 2 l of toluene. Under cooling on ice, 196.0 g of 2'-hyroxy-4',6'-dimethoxyacetophenone and 2 l of toluene solution of 72.0 ml carbon sulfide were added dropwise to the solution. The mixture was stirred over 20 hours at room temperature, and 7 l of water was added in order to extract the toluene layer. This toluene solution was adjusted to pH 4–5 by addition of 800 ml of 10% aqueous sulfuric acid solution and was then stirred for 5 hours at room temperature. Subsequently, the solution was allowed to stand overnight. The resulting yellow crystals were collected by filtration under reduced pressure, sufficiently washed with water, and dried at 50° C. for 3 days under reduced pressure, whereby crude 4-hydroxy-5,7-dimethoxychromene-2-thion, 160.0 g, was obtained. 160.0 g of 4-hydroxy-5,7-dimethoxychromene-2-thion and 110.4 g of potassium carbonate were suspended in 4.8 l of water. 125.0 ml methyl iodide was added to the mixture at room temperature, followed by stirring for 2.5 hours. The resulting crystals were collected by filtration under reduced pressure, sufficiently washed with water, and dried at 60 C. under reduced pressure, whereby crude 5,7-dimethoxy-2-methylthiochromone, 146.8 g, was obtained. 146.8 g of 5,7-dimethoxy-2-methylthiochromone was suspended in 3 l of methanol. Under cooling on ice, 1.5 l aqueous solution of 252.2 g oxone was added thereto, followed by stirring for 3 hours at room temperature. 4 l of water was added to the reaction solution. The product was extracted twice with dichloromethane (4 l and 2 l, respectively), and the resulting organic layer was washed with saturated salt water and dried over sodium sulfate anhydride. The solvent was distilled out under reduced pressure. The crude product was subjected to recrystallization from 8 l methanol, whereby 5,7-dimethoxy-2-methylsulfinylchromone (Intermediate (1)), 91.5 g, was obtained.

The inhibitory action on aldose reductase demonstrated by the present compounds is explained in the following experimental examples.

Experimental Example 1

<Determination of Aldose Reductase Activity (In Vitro)>

6 week-old Wistar rats were sacrificed under ether anesthesia, and immediately lenses were removed and stored at –20° C. The crystalline lenses were homogenized in 135 mM sodium-potassium-phosphate buffer (pH 7.0) and centrifuged for 30 min. at 30,000 rpm. The supernatant was used as an aldose-reductase solution. The above procedure was carried out at 4° C. The enzyme solution was stored at –20° C.

The measurement of aldose reductase activity was conducted according to the method as described by Dufrane et al. (Biochemical Medicine, 32: 99–105 (1984)).

That is, 100 µl of the above enzyme solution and 100 µl of a solution prepared by dissolving a compound obtained in the following example to a final concentration of from $1.0 \times 10^{-5}$ to $4.0 \times 10^{-7}$ M in dimethylsulfoxide (DMSO) were added to 800 µl of 135 mM sodium-potassium-phosphate buffer (pH 7.0) containing 100 mM lithium sulfate, 0.03 mM NADPH (reduced form of nicotinamide adenine dinucleotide phosphate) and 20 mM glucose as a substrate. The sample was allowed to react for 30 min. at 30° C. The reaction was stopped by addition of 0.3 ml of 0.5N hydrochloric acid. The NADP (oxided form of nicotinamide adenine dinucleotide) formed during the above reaction was converted into a fluorescent substance by addition of 1 ml of 6N sodium hydroxide containing 10 mM imidazole. 30 min. thereafter, the sample was measured for fluorescence intensity at the fluorescence wavelength of 460 nm (excitation wavelength: 360 nm) using a fluorescence photometer F-4000 (manufactured by Hitachi, Ltd.) at room temperature. A sample containing DMSO in place of the present compound was used as a control, and its fluorescence intensity was determined in the same manner as above.

Aldose reductase is an enzyme to convert DL-glyceraldehyde or glucose into polyol in the presence of NADPH as a coenzyme. As this reaction proceeds, NADPH is converted into NADP, so that the smaller amount of NADP formed indicates higher inhibition of aldose reductase.

Experimental Example 2

<Determination of Aldose Reductase Activity (In Vivo)>

Streptozotocin (STZ) dissolved in 10 mM citrate buffer (pH 4.5) was administered intravenously to 6 week-old Wistar male rats at the brush in an amount of 65 mg/kg. 48 hours thereafter, blood was collected from the carotid acteries of the rats. Rats with a blood glucose level of 200 mg/dl or more were clasfied as those with diabetes. Rats with a persistent high level of blood sugar were employed in the experiment. The blood glucose level was determined by the glucose oxidase method.

2 weeks after administration of STZ, a compound obtained in the following examples was suspended in purified water or 0.5% carboxy sodium cellulose solution. This solution was orally administered into a rat in an amount of 30 mg/kg for 2 weeks. 2 weeks after the adminstration, sciatic nerves were removed from the rat under ether anesthesia. The sciatic nerves were weighed and stored at –20° C.

The amount of sorbitol contained in the sciatic nerves was determined as follows.

That is, the sciatic nerves were subjected to extraction with 1 ml of purified water containing 10 µg/ml arabinitol at 100° C. for 20 min., followed by addition of 0.2 ml each of 0.2M barium hydroxide and 0.19M zinc sulfate. The mixture was centrifuged (3000 rpm, 30 min.), and the supernatant was evaporated to dryness. The resulting sample was trimethysilylated and was then analyzed by gas chromatography. Sorbitol is an intermediate which occurs during convertion of glucose to fructose by aldose reductase, and this intermediate is accumulated together with fructose in the crystalline lenses and sciatic nerves, particularly under a high level of blood glucose. Therefore, the smaller amount of sorbitol formed indicates higher inhibition of aldose reductase. Table 3 shows inhibition rate (%) by the present compounds at the concentration of 10 µM, 50% inhibition concentration [$IC_{50}$ (M)] and repression rate (%) at 30 mg/kg.

TABLE 3

| | 50% Inhibition Conc. [$IC_{50}(M)$] | Inhibition rate % | Repression rate % |
|---|---|---|---|
| Compound obtained in Example 1 | $1.1 \times 10^{-7}$ | 97.3 | |
| Compound obtained in Example 2 | $1.1 \times 10^{-7}$ | 87.1 | |
| Compound obtained in Example 11 | $4.0 \times 10^{-8}$ | 98.5 | |
| Compound obtained in Example 12 | $1.5 \times 10^{-7}$ | 93.0 | |
| Compound obtained in Example 13 | $1.8 \times 10^{-8}$ | 93.7 | |
| Compound obtained in Example 14 | $1.9 \times 10^{-7}$ | 86.8 | |
| Compound obtained in Example 15 | $3.8 \times 10^{-8}$ | 98.4 | |
| Compound obtained in Example 16 | $3.8 \times 10^{-8}$ | 96.5 | |
| Compound obtained in Example 17 | $1.3 \times 10^{-7}$ | 95.1 | |
| Compound obtained in Example 18 | $1.8 \times 10^{-8}$ | 98.7 | 5.9 (50 mg/Kg) |
| Compound obtained in Example 19 | $4.0 \times 10^{-6}$ | 69.8 | |
| Compound obtained in Example 22 | $3.0 \times 10^{-8}$ | 98.3 | 6.8 (50 mg/Kg) |
| Compound obtained in Example 23 | $4.4 \times 10^{-8}$ | 100 | |
| Compound obtained in Example 25 | $6.0 \times 10^{-8}$ | 93.2 | 16.0 (50 mg/Kg) |
| Compound obtained in Example 26 | $6.5 \times 10^{-8}$ | 98.1 | |
| Compound 1 obtained in Example 28 | $1.7 \times 10^{-7}$ | 95.4 | |
| Compound 2 obtained in Example 28 | $3.0 \times 10^{-7}$ | 95.4 | |
| Compound obtained in Example 31 | $2.3 \times 10^{-7}$ | 100 | |
| Compound obtained in Example 33 | $1.1 \times 10^{-7}$ | 96.7 | |
| Compound 1 obtained in Example 34 | $4.6 \times 10^{-7}$ | 98.0 | |
| Compound 2 obtained in Example 34 | $1.0 \times 10^{-6}$ | 96.6 | |
| Compound obtained in Example 35 | | 43.7 | |
| Compound obtained in Example 36 | | 12.3 | |
| Compound 1 obtained in Example 37 | | 51.6 | |
| Compound 2 obtained in Example 39 | | 4.6 | |
| Compound obtained in Example 40 | | 27.9 | |
| Compound obtained in Example 41 | | 52.4 | |
| Compound obtained in Example 42 | | 47.7 | |
| Compound obtained in Example 43 | | 44.0 | |
| Compound obtained in Example 46 | | 28.4 | |
| Compound obtained in Example 47 | | 36.5 | |
| Compound obtained in | | 48.2 | |

TABLE 3-continued

| | 50% Inhibition Conc. [IC$_{50}$(M)] | Inhibition rate % | Repression rate % |
|---|---|---|---|
| Example 49 Compound obtained in Example 52 | | 31.7 | |
| Compound obtained in Example 53 | | 22.8 | |
| Compound obtained in Example 56 | | 35.9 | |
| Compound obtained in Example 57 | | 50.5 | |
| Compound obtained in Example 58 | | 37.4 | |
| Compound obtained in Example 59 | | 37.1 | |
| Compound obtained in Example 63 | | 31.1 | |
| Compound obtained in Example 64 | | 52.9 | |
| Compound obtained in Example 65 | | 23.1 | |
| Compound obtained in Example 66 | | 31.5 | |
| Compound obtained in Example 69 | $1.8 \times 10^{-8}$ | 97.7 | |
| Compound obtained in Example 70 | $1.0 \times 10^{-6}$ | 85.5 | |
| Compound obtained in Example 71 | $1.0 \times 10^{-7}$ | 88.7 | |
| Compound obtained in Example 72 | $1.0 \times 10^{-7}$ | 84.0 | |
| Compound obtained in Example 73 | | 16.4 | |
| Compound obtained in Example 74 | | 52.1 | |
| Compound obtained in Example 75 | | 43.5 | |
| Compound 2 obtained in Example 77 | | 40.0 | |
| Compound (Formula B) | $1.8 \times 10^{-7}$ | 94.5 | |
| Capillarisin | $1.6 \times 10^{-6}$ | 81.0 | 18.9 (100 mg/kg) |

Compound (Formula B):

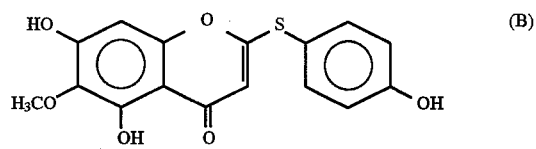

It has been reported that some aldose reductase inhibitors exhibit inhibition of aldehyde reductase, i.e. an enzyme analogous to aldose reductase (Biochemical Pharmacology, 40: 1033–1042 (1990)). Aldehyde reductase is present together with aldose reductase within the same tissues. If such an aldose reductase inhibitor acts on said two enzymes to the same extent, then the effect of the inhibitor is lowered depending on the amount of aldehyde reductase present. It is expected therefore that such an inhibitor also having the inhibitory action on aldehyde reductase is consumed for aldehyde reductase before it acts on aldose reductase, and thus no sufficient effects can be expected unless the inhibitor is selective toward aldose reductase.

Therefore, the present inventors have conducted the following experiment in order to examine the ability of selective inhibition of aldose reductase demonstrated by the present compounds.

Experimental Example 3

<Ability of Selective Inhibition of Aldose Reductase>

From rats under ether anesthesia, the kidneys were removed and stored at −20° C. The kidneys were homogenized in 0.1M phosphate buffer (pH 7.2) containing 5 mM 2-mercaptoethanol (kidneys:buffer=1:10 (by volume)), followed by centrifugation (14,000 rpm, 20 min., 4° C.), whereby a supernatant was obtained. The supernatant thus obtained was subjected to 30–60% ammonium sulfate fractionation. The resulting precipitates were collected by centrifugation (9,200 rpm, 20 min., 4° C.) The precipitates were suspended in a buffer with the same composition as described above. This suspension was dialyzed overnight at 4° C. against a buffer with the same composition, so that a crude aldehyde reductase solution was obtained. The activity of aldehyde reductase was determined in the same manner as for aldose reductase except for use of 0.1M phosphate buffer (pH 7.0) and as substrate 50 mM DL-glyceraldehyde.

The ability of selective inhibition of aldose reductase was determined by dividing the thus obtained 50% inhibition concentration [IC$_{50}$(M)] of aldehyde reductase by the above 50% inhibition concentration [IC$_{50}$(M)] of aldose reductase.

TABLE 4

|  | 50% Inhibition Aldose reductase | conc [IC$_{50}$(M)] Aldehyde reductase | Ability of selective inhibition |
|---|---|---|---|
| Compound [formular (B)] | $1.8 \times 10^{-7}$ | $1.0 \times 10^{-5}$ | 55.5 |
| Compound obtained in Example 1 | $1.1 \times 10^{-7}$ | $>1.0 \times 10^{-4}$ | >1000 |
| Compound obtained in Example 16 | $3.8 \times 10^{-8}$ | $>1.0 \times 10^{-4}$ | >1000 |
| Compound obtained in Example 18 | $1.8 \times 10^{-8}$ | $>1.0 \times 10^{-4}$ | >1000 |
| Compound obtained in Example 22 | $3.0 \times 10^{-8}$ | $>1.0 \times 10^{-4}$ | >1000 |
| Compound obtained in Example 23 | $4.4 \times 10^{-8}$ | $>1.0 \times 10^{-4}$ | >1000 |
| Compound obtained in Example 25 | $6.0 \times 10^{-8}$ | $>1.0 \times 10^{-4}$ | >1000 |
| Compound obtained in Example 33 | $1.1 \times 10^{-7}$ | $1.0 \times 10^{-4}$ | 1000 |

The result shown in Table 4 indicates that the present compounds exhibit significantly high selective inhibition of aldose reductase. The compounds obtained in the Examples were examined for acute toxicity using ICR strain mice by oral administration. As a result, no death was observed by the oral administration of 1 g/kg. It follows that the present compounds are of very low toxicity and high safety.

Next, an explanation is made of the amount of the present composition administered as well as of the pharmaceutical manufacturing thereof.

The present compounds can be administered as such or together with customary pharmaceutical carriers into animals and humans. The form of administration is not particularly limited and can be suitably selected as necessary: i.e. the present compounds can be used as drugs for oral administration, e.g. in the form of tables, capsules, granules, fine granules, and powder or as drugs for parenteral administration, e.g. in the form of injection liquid and suppositories.

In order to achieve the desired effects of drugs for oral administration, the present compound is suitably administered into an adult person in an amount 30 mg to 2 g per day at suitable intervals, depending on the body weight age of the patient as well as the degree of diseases.

The drugs for oral administration are manufactured using e.g. starch, milk sugar, white sugar, mannitol, carboxymethylcellulose, corn starch, inorganic salts, etc., according to a conventional method. For the pharmaceutical manufacturing of this type of drug, a binding agent, an disintegration agents, fluidity promoters, correctives, coloring agents, spices, etc., can be suitably used together with the above vehicles. Specific examples are as follows:

[Binding Agents]

Starch, dextrin, powder of gum arabic, gelatin, hydroxypropyl starch, methyl cellulose, carboxymethylcellulose sodium, hydroxypropylcellulose, crystalline cellulose, ethyl cellulose, polyvinylpyroridone, and macrogol.

[Disintegration Agents]

Starch, hydroxypropyl starch, carboxylmethylcellulose sodium, carboxycellulose calcium, low substituted hydroxypropyl cellulose.

[Surface Active Agents]

Sodium lauryl sulfate, soybean lecithin, sucrose fatty acid ester, Polysolvate 80.

[Moisture Agents]

Talc, waxes, hydrogenated vegetable oils, sucrose fatty acid ester, magnesium stearate, calcium stearate, aluminium stearate, polyethylene glycol.

[Fluidity Promoters]

Light silicic acid anhydride, Dried gel of aluminium hydroxide, synthetic aluminium silicate, magnesium silicate.

The present compounds can be administered in the form of suspension, emulsion, syrup, and elixir, and these forms of drugs may contain correctives and coloring agents.

In order to achieve the desired effects of drugs for parenteral administration, the present compound is suitably administered into an adult person at intravenously, subcutaneously, intramuscularly, or by intravenous drip injection in an mount 0.1 mg to 600 mg per day at suitable intervals, depending on the body weight and age of the patient as well as the degree of diseases.

The drugs for parenteral administration are manufactured according to a conventional method, which may comprises generally use, as diluents, of distilled water for injection, physiological saline, an aqueous glucose solution, vegetable oils for injection, sesame oil, peanut oil, soybean oil, corn oil, polypropylene glycol, polyethylene glycol, etc. A disinfectant, antiseptic, stabilizer may be added as necessary. In respect of stability, these parenteral drugs may be introduced into vials, etc., and then lyophilized according to a conventional techniques so that liquid drugs can be reconstituted from the lyophilized drugs just before use. Furthermore, an isotonic agent, a stabilizer, a disinfectant, and an analgesia agent may be incorporated as necessary.

Other parenteral drugs include surgical liquid drugs and ointments, as well as suppositories for administration into the rectum, and these are manufactured in accordance with a usual manner.

THE BEST MODE FOR CARRYING OUT THE INVENTION

The present invention is explained in detail by referring the following examples, to which however the invention is not restricted.

EXAMPLE 1

5.05 g Capillarisin, 22.05 g potassium carbonate, and 500 ml acetone were introduced into a reaction vessel. 9.95 ml methyl iodide was added to the mixture under stirring, and the solution was refluxed over 20 hours. Then, water was added to the solution thus reacted. The product was extracted twice with ethyl acetate. The organic layer was washed with saturated salt water and dried over sodium sulfate anhydride. The solvent was distilled out under reduced pressure, and the resulting crystals containing impurities were purified by flash column chromatography (chloroform:acetone=30:1), whereby 4.66 g trimethyl Capillarisin was obtained.

2.013 g trimethyl Capillarisin, 1.551 g potassium carbonate, 30 ml acetone, and 30 ml water were placed in a reaction vessel. After 1.416 g of 4-hydroxybenzenethiol was added, the mixture was stirred over 3 hours at room temperature. The solution thus reacted was made weakly acidic by addition of dilute hydrochloric acid. The product was extracted twice with ethyl acetate, and the organic layer was washed with saturated salt water and dried over sodium sulfate anhydride. The solvent was distilled out under reduced presssure, and the resulting crystals containing impurities were subjected to recrystallization from 150 ml ethanol, whereby 1.405 g of 2-(4-hydroxyphenylthio)-5,6,7-trimethoxychromone with the following physicochemical properties was obtained.

Melting point: 235°–238° C.

Infrared absorption spectrum (IR, ν max cm$^{-1}$, KBr): 3176, 1614, 1580 1486, 1468, 1420, 1326, 1272, 1200, 1122, 1112

Proton nuclear magnetic resonance spectrum (δ ppm in DMSO-d$_6$): 10.15 (1H, br s), 7.49 (2H, d, J=8.3Hz), 6.97 (1H, s) 6.94 (2H, d, J=8.3Hz), 5.40 (1H, s), 3.91 (3H, s), 3.74 (3H, s), 3.73 (3H, s)

Mass spectrum (EI-MS) m/z (%): 360, 349

Elemental analysis: $C_{18}H_{16}O_6S$ Calculated; C:59.99, H:4.48 Found; C:59.90, H:4.53

EXAMPLE 2

5.00 g Capillarisin, 5.46 g potassium carbonate, and 500 ml acetone were introduced into a reaction vessel. 3.74 ml dimethyl sulfate was added to the solution under stirring, and the mixture was allowed to react for 24 hours at room temperature. The solution thus reacted was made weakly acidic by addition of dilute hydrochloric acid. The product was extracted twice with ethyl acetate, and the organic layer was washed with saturated salt water and dried over sodium sulfate anhydride. The solvent was distilled out under reduced presssure, and the resulting crystals containing impurities were purified by flash column chromatography (chloroform:acetone=100:1), so that 4.25 g dimethyl Capillarisin was obtained.

2.034 g trimethyl Capillarisin, 1.490 g potassium carbonate, 30 ml acetone, and 30 ml water were placed in a reaction vessel. After 1.631 g of 4-hydroxybenzenethiol was added, the mixture was stirred over 3 hours at room temperature. The solution thus reacted was made weakly acidic by addition of dilute hydrochloric acid. The product was extracted twice with ethyl acetate, and the organic layer was washed with saturated salt water and dried over sodium sulfate anhydride. The solvent was distilled out under reduced presssure, and the resulting crystals containing impurities were subjected to recrystallization from 220 ml ethanol, whereby 1.699 g of 5-hydroxy-2-(4-hydroxyphenylthio)-6,7 -dimethoxychromone with the following physicochemical properties was obtained.

Melting point: 240°–243° C.

Infrared absorption spectrum (IR, ν max cm$^{-1}$, KBr): 3304, 1650, 1616, 1600, 1584, 1502, 1492, 1456, 1434, 1334, 1276, 1126, 1112, 822

Proton nuclear magnetic resonance spectrum (δ ppm in DMSO-d$_6$): 12.57 (1H, br s), 7.51 (2H, d, J=8.8Hz), 6.96 (2H, d, J=8.8Hz), 6.74(1H, s), 5.52(1H, s), 3.89(3H, s), 3.70(3H, s)

Mass spectrum (EI-MS) m/z (%): 346, 331, 317, 303, 300

Elemental analysis: $C_{17}H_{14}O_6S$ Calculated; C:58.95, H:4.07, S: 9.26 Found; C:58.88, H:3.93, S: 9.35

EXAMPLE 3

A mixture consisting of 1.03 g Capillarisin, 15.97 ml of n-propyl iodide, 4.50 g potassium carbonate, and 50 ml acetone was stirred under reflux over 3 days at a bath temperature of 60° C. Subsequently, water was added to the mixture thus reacted, and the product was extracted twice with ethyl acetate. The organic layer was washed with saturated salt water and dried over sodium sulfate anhydride. The solvent was distilled out under reduced presssure, and 1.36 g of the resulting crystals containing impurities were purified by flash column chromatography (chloroform:acetone=80:1), so that 1.26 g of 5,7-dipropoxy-6-methoxy-2-(4-propoxyphenoxy)chromone with the following physicochemical properties was obtained.

Melting point: 93°–94° C. Infrared absorption spectrum (IR, ν max cm$^{-1}$, KBr): 1640, 1630, 1602, 1504, 1392, 1370, 1222, 1184, 1120

Proton nuclear magnetic resonance spectrum (δ ppm in CDCl$_3$): 7.08 (2H, d, J=9.3Hz), 6.92 (2H, d, J=9.3Hz), 6.66(1H, s), 5.24(1H, s), 4.02 (2H, t, J=6.5Hz), 4.00 (2H, t, J=6.5Hz), 3.93 (2H, t, J=6.5Hz), 3.87 (3H, s), 1.97–1.72 (6H, m), 1.09 (3H, t, J=7.5Hz), 1.05 (3H, t, J=7.5Hz), 1.04 (3H, t, J=7.5Hz)

Mass spectrum (EI-MS) m/z (%): 442, 427, 413, 399, 371

Elemental analysis: $C_{25}H_{30}O_7$ Calculated; C:67.86, H:6.83 Found; C:67.85, H:6.83

EXAMPLE 4

A mixture consisting of 506 mg Capillarisin, 6.4 ml isopropyl iodide, 1.77 g potassium carbonate, and 25 ml acetone was stirred under reflux over 5 days at a bath temperature of 60° C. Subsequently, water was added to the mixture thus reacted, and the product was extracted twice with ethyl acetate. The organic layer was washed with saturated salt water and dried over sodium sulfate anhydride. The solvent was distilled out under reduced presssure, and 1.36 g of the resulting crystals containing impurities were purified by flash column chromatography (hexane:ethyl acetate=6:1), whereby 470.8 mg of 5,7-diisopropoxy-2-(4-isopropoxyphenoxy)-6-methoxychromone and 71.8 mg of 5-hydroxy-7-isopropoxy-2-(4-isopropoxyphenoxy)-6-methoxychromone with the following physicochemical properties were respectively obtained.

(1) 5,7-diisopropoxy-2-(4-isopropoxyphenoxy)-6-methoxychromone

Infrared absorption spectrum (IR, ν max cm$^{-1}$, neat): 2980, 1632, 1602, 1502, 1450, 1426, 1384, 1332, 1226, 1190, 1138, 1114, 1080, 824, 752

Proton nuclear magnetic resonance spectrum (δ ppm in CDCl$_3$): 7.08 (2H, d, J=9.3Hz), 6.91 (2H, d, J=9.3Hz), 6.67(1H, s), 5.23(1H, s), 4.63–4.47 (3H, m), 3.85 (3H, s), 1.44 (1H, d, J=6.1Hz), 1.35 (6H, d, J=6.1Hz), 1.34 (6H, d, J=6.1Hz)

Mass spectrum (EI-MS) m/z (%): 442, 427, 400, 357, 343, 341, 325, 315, 300, 298

High resolution mass spectrum (HR-EI-MS) (Hereafter referred to as "HRMS"): $C_{25}H_{30}O_7$ Calculated; 442.19914 Found; 442.20009

(2) 5-hydroxy-7-isopropoxy-2-(4-isopropoxyphenoxy)-6-methoxychromone

Melting point: 124°–125° C.

Infrared absorption spectrum (IR, ν max cm$^{-1}$, KBr): 2976, 2932, 1664, 1614, 1502, 1456, 1414, 1374, 1350, 1232, 1192, 1170, 1120

Proton nuclear magnetic resonance spectrum (δ ppm in CDCl$_3$): 12.66 (1H, s) 7.08 (2H, d, J=9.3Hz), 6.93 (2H, d, J=9.3Hz), 6.42 (1H, s), 5.24 (1H, s), 4.66–4.51 (2H, m), 3.87 (3H, s), 1.43 (6H, d, J=6.3Hz), 1.36 (6H, d, J=6.3Hz)

Mass spectrum (EI-MS) m/z (%): 400, 385, 357, 343, 315, 301, 298, 273

HRMS: C$_{22}$H$_{24}$O$_7$ Calculated; 400.15219 Found; 400.15143

EXAMPLE 5

A mixture consisting of 520 mg Capillarisin, 9.4 ml n-butyl iodide, 2.23 g potassium carbonate, and 30 ml acetone was stirred under reflux over 3 days at a bath temperature of 60° C. Subsequently, water was added to the mixture thus reacted, and the product was extracted twice with ethyl acetate. The organic layer was washed with saturated salt water and dried over sodium sulfate anhydride. The solvent was distilled out under reduced presssure. 1.00 g of the resulting crystals containing impurities were purified by flash column chromatography (hexane:ethyl acetate= 6:1), to give 730 mg of 2-(4-butoxyphenoxy)-5,7-dibutoxy-6-methoxychromone with the following physicochemical properties.

Melting point: 62°–63° C.

Infrared absorption spectrum (IR, ν max cm$^{-1}$, KBr): 2956, 2936, 1642, 1604, 1504, 1466, 1452, 1392, 1374, 1344, 1220, 1184, 1118

Proton nuclear magnetic resonance spectrum (δ ppm in CDCl$_3$): 7.08 (2H, d, J=9.3Hz), 6.91 (2H, d, J=9.3Hz), 6.66 (1H, s), 5.24 (1H, s), 4.05 (2H, t, J=6.6Hz), 4.04 (2H, t, J=6.6Hz), 3.97 (2H, t, J=6.6Hz), 3.86 (3H, s), 1.91–1.75 (6H, m), 1.60–1.45 (6H, m), 1.01 (3H, t, J=7.1Hz), 0.99 (3H, t, J=7.1Hz), 0.96 (3H, t, J=7.1Hz)

Mass spectrum (EI-MS) m/z (%): 484, 469, 455, 441, 427, 285

HRMS: C$_{28}$H$_{36}$O$_7$ Calculated; 484.24608 Found; 484.24626

EXAMPLE 6

A mixture consisting of 535 mg Capillarisin, 9.7 ml of s-butyl iodide, 2.33 g potassium carbonate, and 30 ml acetone was stirred over 5 days under reflux at a bath temperature of 60° C. Then, water was added to the mixture thus reacted, and the product was extracted twice with ethyl acetate. The organic layer was washed with saturated salt water and dried over sodium sulfate anhydride. The solvent was distilled out under reduced presssure. 1.08 g of the resulting crystals containing impurities were purified by flash column chromatography (hexane:ethyl acetate=8:1), whereby 485 mg of 7-s-butoxy-2-(4-s-butoxyphenoxy)-5-hydroxy-6-methoxychromone and 199 mg of 2-(4-s-butoxyphenoxy)-5,7-di-s-butoxy-6-methoxychromone with the following physicochemical properties were respectively obtained.

(1) 2-(4-s-butoxyphenoxy)-5,7-di-s-butoxy-6-methoxychromone

Infrared absorption spectrum (IR, ν max cm$^{-1}$, neat): 2972, 2936, 1634, 1602, 1502, 1450, 1424, 1382, 1336, 1268, 1224, 1188, 1168, 1110, 1026, 984, 834, 752

Proton nuclear magnetic resonance spectrum (δ ppm in CDCl$_3$): 7.07 (2H, d, J=9.0Hz), 6.91 (2H, d, J=9.0Hz), 6.65(1H, s), 5.21(1H, s), 4.40–4.22 (3H, m), 3.83 (3H, s), 1.84–1.65 (6H, m), 1.40 (3H, d, J=5.9Hz), 1.31 (3H, d, J=6.1Hz), 1.27 (3H, dd, J=6.3, 2.7Hz), 1.03 (3H, t, J=7.3Hz), 0.99 (3H, t, J=7.5Hz) 0.95 (3H, t, J=7.6Hz)

Mass spectrum (EI-MS) m/z (%): 484, 455, 428, 372, 357, 316, 301, 298, 273

HRMS: C$_{28}$H$_{36}$O$_7$ Calculated; 484.24608 Found; 484.24908

(2) 7-s-butoxy-2-(4-s-butoxyphenoxy)-5-hydroxy-6-methoxychromone

Infrared absorption spectrum (IR, ν max cm$^{-1}$, neat): 2972, 2936, 2880, 1660, 1610, 1566, 1500, 1452, 1428, 1384, 1346, 1298, 1232, 1186, 1120, 1026, 1008, 982, 834

Proton nuclear magnetic resonance spectrum (δ ppm in CDCl$_3$): 12.7 (1H, s), 7.08 (2H, d, J=9.3Hz), 6.93 (2H, d, J=9.3Hz), 6.42 (1H, s), 5.24 (1H, s), 4.44–4.24 (2H, m), 3.87 (3H, s), 1.86–1.61 (4H, m), 1.38 (3H, d, J=6.4Hz), 1.32 (3H, d, J=6.4Hz), 1.02 (3H, t, J=7.3Hz), 1.00 (3H, t, J=7.3HZ)

Mass spectrum (EI-MS) m/z (%): 428, 372, 357, 316, 301, 298, 273

HRMS: C$_{24}$H$_{28}$O$_7$ Calculated; 484.18349 Found; 484.18385

EXAMPLE 7

A mixture consisting of 515 mg Capillarisin, 9.4 ml isobutyl iodide, 2.25 g potassium carbonate, and 30 ml acetone was stirred over 4 days under reflux at a bath temperature of 60° C. Then, water was added to the mixture thus reacted, and the product was extracted twice with ethyl acetate. The organic layer was washed with saturated salt water and dried over sodium sulfate anhydride. The solvent was distilled out under reduced presssure. 750 mg of the resulting oil was purified by flash column chromatography (hexane:ethyl acetate=7:1), whereby 435 mg of 5-hydroxy-7-isobutoxy-2-(4-isobutoxyphenoxy)-6-methoxychromone with the following physicochemical properties was obtained.

Melting point: 115°–116° C.

Infrared absorption spectrum (IR, ν max cm$^{-1}$, KBr): 2956, 1666, 1612, 1566, 1506, 1492, 1460, 1416, 1382, 1366, 1232, 1188, 1172, 1124

Proton nuclear magnetic resonance spectrum (δ ppm in CDCl$_3$): 12.7 (1H, s), 7.09 (2H, d, J=9.3Hz), 6.94 (2H, d, J=9.3Hz), 6.39 (1H, s), 5.24 (1H, s), 3.89 (3H, s), 3.80 (2H, d, J=6.3Hz) 3.73 (2H, d, J=6.3Hz), 2.23–2.07 (2H, m), 1.07 (6H, d, J=6.4Hz), 1.04 (6H, d, J=6.4Hz)

Mass spectrum (EI-MS) m/z (%): 428, 412, 398, 385, 371, 367, 357, 354, 329

HRMS: C$_{24}$H$_{28}$O$_7$ Calculated; 484.18349 Found; 484.18404

EXAMPLE 8

A mixture consisting of 144 mg of 7-s-butoxy-2-(4-s-butoxyphenoxy)-5-hydroxy-6-methoxychromone prepared in Example 6, 1.3 ml isopropyl iodide, 235 mg potassium carbonate, and 8 ml acetone was stirred over 2 days under reflux at a bath temperature of 60° C.

Then, water was added to the mixture thus reacted, and the product was extracted twice with ethyl acetate. The organic layer was washed with saturated salt water and dried over sodium sulfate anhydride. The solvent was distilled out under reduced presssure, whereby 154 mg of 7-s-butoxy-2-(4-s-butoxyphenoxy)-5-isopropoxy-6-methoxychromone with the following physicochemical properties was obtained.

Infrared absorption spectrum (IR, ν max cm⁻¹, neat): 2972, 2936, 1640, 1602, 1502, 1478, 1450, 1424, 1384, 1268, 1250, 1222, 1188, 1106, 1082, 1028, 984, 828

Proton nuclear magnetic resonance spectrum (δ ppm in CDCl₃): 7.07 (2H, d, J=9.0Hz) 6.91 (2H, d, J=9.0Hz), 6.66 (1H, s), 5.22 (1H, s), 4.58–4.22 (3H, m), 3.85 (3H, s), 1.95–1.60 (4H, m), 1.40 (3H, d, J=6.1Hz) 1.35 (3H, d, J=6.1Hz), 1.34 (3H, d, J=6.1Hz), 1.31 (3H, d, J=6.1Hz), 1.03 (3H, t, J=7.3Hz) 0.99 (3H, t, J=7.3Hz)

Mass spectrum (EI-MS) m/z (%): 470, 455, 428, 412, 398, 372, 355, 298

HRMS: $C_{27}H_{34}O_7$ Calculated; 470.23044 Found; 470.23044

EXAMPLE 9

A mixture consisting of 115 mg of 5-hydroxy-7-isobutoxy-2-(4-isobutoxyphenoxy)-6-methoxychromone prepared in Example 7, 1 ml isopropyl iodide, 186 mg potassium carbonate, and 7 ml acetone was stirred over 2 days under reflux at a bath temperature of 60° C. Then, water was added to the mixture thus reacted, and the product was extracted twice with ethyl acetate. The organic layer was washed with saturated salt water and dried over sodium sulfate anhydride. The solvent was distilled out under reduced presssure, whereby 131 mg of 7-isobutoxy-2-(4-isobutoxyphenoxy)-5-isopropoxy-6-methoxychromone with the following physicochemical properties was obtained.

Proton nuclear magnetic resonance spectrum (δ ppm in CDCl₃): 7.08 (2H, d, J=9.0Hz), 6.92 (2H, d, J=9.0Hz), 6.65 (1H, s), 5.23 (1H, s), 4.57–4.45 (1H, m), 3.86(3H, s), 3.81 (2H, d, J=6.6Hz), 3.72 (2H, d, J=6.6Hz), 2.30–2.10 (2H, m), 1.34 (3H, d, J=6.1Hz), 1.08 (3H, d, J=6.6Hz), 1.04 (3H, d, J=6.8Hz)

Mass spectrum (EI-MS) m/z (%): 470, 455, 428, 412, 385, 371, 357

EXAMPLE 10

A mixture consisting of 64 mg of 5-hydroxy-7-isopropoxy-2-(4-isopropoxyphenoxy)-6-methoxychromone prepared in Example 4, 0.25 ml ethyl iodide, 110 mg potassium carbonate, and 4 ml acetone was stirred over 2 days under reflux at a bath temperature of 60° C. Then, water was added to the mixture thus reacted, and the product was extracted twice with ethyl acetate. The organic layer was washed with saturated salt water and dried over sodium sulfate anhydride. The solvent was distilled out under reduced presssure, whereby 68 mg of 5-ethoxy-7-isopropoxy-2-(4-isopropoxyphenoxy)-6-methoxychromone with the following physicochemical properties was obtained.

Melting point: 110°–111° C.

Infrared absorption spectrum (IR, ν max cm⁻¹, KBr): 2980, 1642, 1602, 1502, 1478, 1454, 1394, 1380, 1344, 1226, 1192, 1172, 1140, 1116, 1088, 1026

Proton nuclear magnetic resonance spectrum (δ ppm in CDCl₃): 7.08 (2H, d, J=9.3Hz), 6.61 (2H, d, J=9.3Hz), 6.67 (1H, s), 5.23 (1H, s), 4.63 (1H, h, J=6.1Hz), 4.53 (1H, h, J=6.1Hz), 4.11 (2H, q, J=7.1Hz), 3.86 (3H, s), 1.45 (3H, t, J=7.1Hz), 1.44 (6H, d, J=6.1Hz), 1.35 (6H, d, J=6.1Hz)

Mass spectrum (EI-MS) m/z (%): 428, 413, 371, 357, 341, 329, 322 299, 280

HRMS: $C_{24}H_{28}O_7$ Calculated; 428. 18349 Found; 428. 18322

EXAMPLE 11

A mixture consisting of 1.07 g Capillarisin, 8.13 ml ethyl iodide, 2.80 g potassium carbonate, and 500 ml acetone was stirred under reflux over 4 days at a bath temperature of 60° C. Then, water was added to the mixture thus reacted, and the product was extracted twice with ethyl acetate. The organic layer was washed with saturated salt water and dried over sodium sulfate anhydride. The solvent was distilled out under reduced pressure, and 1.24 g of the resulting crystals containing impurities were purified by flash column chromatography (chloroform:acetone=40:1), so that 955 mg triethyl Capillarisin was obtained. 213 mg of the triethyl Capillarisin, 267 g of 4-hydroxybenzenethiol, 585 mg potassium carbonate, 3 ml acetone, and 3 ml water were placed in a reaction vessel. The mixture was stirred overnight at room temperature. The reaction solution was made weakly acidic by addition of dilute hydrochloric acid. The product was extracted twice with chloroform, and the organic layer was washed with saturated salt water and dried over sodium sulfate anhydride. The solvent was distilled out under reduced pressure, and 492 mg crystals containing impurities were recrystallized from 8 ml methanol, whereby 141 mg of 5,7-diethoxy-2-(4-hydroxyphenylthio)-6-methoxychromone with the following physicochemical properties was obtained.

Melting point: 236°–237° C.

Infrared absorption spectrum (IR, ν max cm⁻¹, KBr): 3150, 1614, 1574, 1472, 1452, 1432, 1326, 1284, 1114

Proton nuclear magnetic resonance spectrum (δ ppm in DMSO-d₆): 7.36 (2H, d, J=8.5Hz), 6.85 (2H, d, J=8.5Hz), 6.70 (1H, s), 5.62 (1H, s), 4.16 (2H, q, J=7.1Hz), 4.11 (2H, q, J=7.1Hz), 3.89 (3H, s), 1.53 (3H, t, J=7.1Hz), 1.43 (3H, t, J=7.1Hz)

Mass spectrum (EI-MS) m/z (%): 388, 373, 359, 355, 345

Elemental analysis: $C_{20}H_{20}O_6S$ Calculated; C:61.84, H:5.19 Found; C:61.61, H:5.03

EXAMPLE 12

A mixture consisting of 221 mg of 5,7-dipropoxy-6-methoxy-2-(4-propoxyphenoxy)chromone prepared in Example 3, 189 mg of 4-hydroxybenzenethiol, 414 mg potassium carbonate, 3 ml acetone, and 3 ml water was stirred overnight at room temperature. The reaction solution was made weakly acidic by addition of dilute hydrochloric acid. The product was extracted twice with chloroform, and the organic layer was washed with saturated salt water and dried over sodium sulfate anhydride. The solvent was distilled out under reduced pressure, and 479 mg crystals containing impurities were recrystallized from 4 ml methanol, whereby 135 mg of 5,7-dipropoxy-2-(4-hydroxyphenylthio)-6-methoxychromone with the following physicochemical properties was obtained.

Melting point: 212°–213° C.

Infrared absorption spectrum (IR, ν max cm⁻¹, KBr): 1614, 1570, 1454, 1428, 1330, 1288, 1188, 1116

Proton nuclear magnetic resonance spectrum (δ ppm in CDCl₃): 7.36 (2H, d, J=8.6Hz), 6.85 (2H, d, J=8.6Hz) 6.70 (1H, s), 5.61 (1H, s), 4.04 (2H, t, J=6.5Hz), 3.99 (2H, t, J=6.5Hz), 3.87 (3H, s), 1.95–1.83 (4H, m), 1.10 (3H, t, J=7.3Hz), 1.02 (3H, t, J=7.3Hz)

Mass spectrum (EI-MS) m/z (%): 416, 401, 387, 373, 345

Elemental analysis: $C_{22}H_{24}O_6S$ Calculated; C:63.44, H:5.81 Found; C:63.38, H:5.84

EXAMPLE 13

A mixture consisting of 277 mg of 5,7-diisopropoxy-2-(4-isopropoxyphenoxy)-6-methoxychromone prepared in Example 4, 236 mg of 4-hydroxybenzenethiol, 518 mg potassium carbonate, 3 ml acetone, and 3 ml water was stirred overnight at room temperature. The solution thus reacted was made weakly acidic by addition of dilute hydrochloric acid. The product was extracted twice with chloroform, and the organic layer was washed with saturated salt water and dried over sodium sulfate anhydride. The solvent was distilled out under reduced pressure, and 530 mg crystals containing impurities were recrystallized from 4 ml methanol, whereby 94 mg of 5,7-diisopropoxy-2-(4-hydroxyphenylthio)- 6-methoxychromone with the following physicochemical properties was obtained.

Melting point: 233°–234° C.

Infrared absorption spectrum (IR, ν max $cm^{-1}$, KBr): 3100, 2980, 1612, 1580, 1478, 1454, Proton nuclear magnetic resonance spectrum (δ ppm in $CDCl_3$): 7.35 (2H, d, J=8.5Hz), 6.84 (2H, d, J=8.5Hz) 6.70 (1H, s), 5.59 (1H, s), 4.69–4.46 (2H, m), 3.84 (3H, s), 1.46 (6H, d, J=6.1Hz), 1.32 (6H, d, J=6.3Hz)

Mass spectrum (EI-MS) m/z (%): 416, 401, 374, 331, 317, 314, 303, 289

Elemental analysis: $C_{22}H_{24}O_6S$ Calculated; C:63.44, H:5.81 Found; C:63.24, H:5.89

EXAMPLE 14

A mixture solution consisting of 179 mg of 2-(4-butoxyphenoxy)-5,7-dibutoxy-6-methoxychromone obtained in Example 5, 186 mg of 4-hydroxybenzenethiol, 306 mg potassium carbonate, 3 ml acetone, and 3 ml water was stirred overnight at room temperature. The solution thus reacted was made weakly acidic by addition of dilute hydrochloric acid. The product was extracted twice with chloroform, and the organic layer was washed with saturated salt water and dried over sodium sulfate anhydride. The solvent was distilled out under reduced pressure. The resulting crude oil was purified by flash column chromatography (chloroform:acetone=40:1), whereby 66 mg of 5,7-dibutoxy-2-(4-hydroxyphenylthio)-6-methoxychromone with the following physicochemical properties was obtained.

Melting point: 193°–194° C.

Infrared absorption spectrum (IR, ν max $cm^{-1}$, KBr): 2956, 1614, 1574, 1498, 1486, 1464, 1454, 1428, 1330, 1288, 1190, 1112

Proton nuclear magnetic resonance spectrum (δ ppm in $CDCl_3$): 7.35 (2H, d, J=8.8Hz), 6.84 (2H, d, J=8.8Hz), 6.70 (1H, s), 5.61 (1H, s) 4.08 (2H, t, J=6.6Hz) 4.03 (2H, t, J=6.6Hz), 3.86 (3H, s), 1.93–1.77 (4H, m), 1.60–1.40 (4H, m), 1.01 (3 H, t, J=7.3Hz), 0.93 (3H, t, J=7.3Hz)

Mass spectrum (EI-MS) m/z (%): 444, 429, 401, 345

HRMS: $C_{24}H_{28}O_6S$ Calculated; 444.16065 Found; 444.16026

EXAMPLE 15

A mixture consisting of 153 mg of 2-(4-s-butoxyphenoxy)-5,7-di-s-butoxy-6-methoxychromone obtained in Example 6, 161 mg of 4-hydroxybenzenethiol, 353 mg of potassium carbonate, 3 ml of acetone, and 3 ml of water was stirred overnight at room temperature. The reaction solution was made weakly acidic by addition of dilute hydrochloric acid. The product was extracted twice with chloroform. The organic layer was washed with saturated salt water and dried over sodium sulfate anhydride. The solvent was distilled out under reduced pressure. The resulting crude oil was purified by flash column chromatography (chloroform:acetone= 50:1), whereby 137 mg of 5,7-di-s-butoxy-2-(4-hydroxyphenylthio)-6-methoxychromone with the following physicochemical properties was obtained.

Melting point: 191°–192° C.

Infrared absorption spectrum (IR, ν max $cm^{-1}$, KBr): 2972, 2936, 1612, 1580, 1496, 1478, 1454, 1426, 1380, 1324, 1282, 1192, 1112, 834

Proton nuclear magnetic resonance spectrum (δ ppm in $CDCl_3$): 7.34 (2H, d, J=8.5Hz), 6.83 (2H, d, J=8.3Hz), 6.69 (1H, s), 5.58 (1H, s), 4.08–4.30 (2H, m), 3.84 (3H, s), 1.95–1.60 (4H, m), 1.41 (3H, d, J=6.1Hz), 1.25 (3H, dd, J=6.1, 1.0Hz), 1.04 (3H, t, J=7.3Hz), 0.93 (3H, td, J=7.3, 1.0Hz)

Mass spectrum (EI-MS) m/z (%): 444, 415, 388, 372, 359, 332, 317, 314

HRMS: $C_{24}H_{28}O_6S$ Calculated; 444.16065 Found; 444.16312

EXAMPLE 16

A mixture consisting of 153 mg of 7-s-butoxy-2-(4-s-butoxyphenoxy)-5-isopropoxy-6-methoxychromone obtained in Example 8, 121 mg of 4-hydroxybenzenethiol, 261 mg of potassium carbonate, and 3 ml of acetone was stirred overnight at room temperature. The solution thus reacted was made weakly acidic by addition of dilute hydrochloric acid. The product was extracted twice with ethyl acetate. The organic layer was washed with saturated salt water, followed by drying over sodium sulfate anhydride. The solvent was distilled out under reduced pressure. The resulting crude oil was purified by flash column chromatography (chloroform:methanol=70:1), whereby 116 mg of 7-s-butoxy-2-(4-hydroxyphenylthio)-5-isopropoxy-6-methoxychromone with the following physicochemical properties was obtained.

Melting point: 208°–209° C.

Infrared absorption spectrum (IR, ν max $cm^{-1}$, KBr): 2976, 1612, 1580, 1496, 1478, 1454, 1426, 1378, 1324, 1282, 1192, 1168, 1112, 834

Proton nuclear magnetic resonance spectrum (δ ppm in $CDCl_3$): 7.34 (2H, d, J=8.8Hz), 6.84 (2H, d, J=8.8Hz), 6.70 (1H, s), 5.59 (1H, s), 4.58–4.38 (2H, m), 3.85 (3H, s), 1.95–1.70 (2H, m), 1.41 (3H, d, J=5.9Hz), 1.33 (3H, d, J=6.1Hz), 1.32 (3H, d, J=6.1Hz), 1.04 (3H, t, J=7.3Hz)

Mass spectrum (EI-MS) m/z (%): 430, 415, 388, 372, 358, 332, 317, 314

HRMS: $C_{23}H_{26}O_6S$ Calculated; 430.14500 Found; 430.14557

EXAMPLE 17

A mixture consisting of 130 mg of 7-isobutoxy-2-(4-isobutoxyphenoxy)-5-isopropoxy-6-methoxychromone obtained in Example 9, 105 mg of 4-hydroxybenzenethiol, 229 mg of potassium carbonate, and 3 ml of acetone was stirred overnight at room temperature. The solution thus reacted was made weakly acidic by addition of dilute hydrochloric acid. The product was extracted twice with ethyl acetate. The organic layer was washed with saturated salt water and then dried over sodium sulfate anhydride. The solvent was distilled out under reduced pressure. The resulting crude oil was purified by flash column chromatography (chloroform:methanol=70:1), whereby 89 mg of 2-(4-hydroxyphenylthio)-7-isobutoxy-5-isopropoxy-6-methoxychromone with the following physicochemical properties was obtained.

Melting point: 219°–220° C.

Infrared absorption spectrum (IR, v max cm$^{-1}$, KBr): 2968, 1612, 1580, 1496, 1484, 1466, 1454, 1426, 1378, 1326, 1282, 1192, 1174, 1114, 834

Proton nuclear magnetic resonance spectrum (δ ppm in CDCl$_3$): 7.34 (2H, d, J=8.6Hz), 6.83 (2H, d, J=8.6Hz), 6.71 (1H, s), 5.59 (1H, s), 4.50 (1H, d, J=6.1Hz), 3.87 (3H, s), 3.83 (2H, d, J=6.6Hz), 2.23–2.13 (1H, m), 1.33 (6H, d, J=6.1Hz), 1.04 (6H, d, J=6.8Hz)

Mass spectrum (EI-MS) m/z (%): 430, 415, 388, 372, 358, 332, 317

HRMS: $C_{23}H_{26}O_6S$ Calculated; 430. 14500 Found; 430. 14529

EXAMPLE 18

A mixture consisting of 68 mg of 5-ethoxy-7-isopropoxy-2-(4-isopropoxyphenoxy)-6-methoxychromone prepared in Example 10, 60 mg of 4-hydroxybenzenethiol, 131 mg of potassium carbonate, 2 ml of acetone was stirred overnight at room temperature. The solution thus reacted was made weakly acidic by addition of dilute hydrochloric acid. The product was extracted twice with ethyl acetate. The organic layer was washed With saturated salt water and then dried over sodium sulfate anhydride. The solvent was distilled out under reduced pressure. The resulting crude oil was purified by flash column chromatography (chloroform:methanol=80:1), whereby 45 mg of 5-ethoxy-2-(4-hydroxyphenylthio)-7-isopropoxy-6-methoxychromone with the following physicochemical properties was obtained.

Melting point: 224°–225° C.

Infrared absorption spectrum (IR, v max cm$^{-1}$, KBr): 2980, 1612, 1580, 1498, 1478, 1454, 1428, 1392, 1372, 1320, 1282, 1228, 1194, 1168, 1112, 834

Proton nuclear magnetic resonance spectrum (δ ppm in CDCl$_3$): 7.34 (2H, d, J=8.9Hz), 6.84 (2H, d, J=8.9Hz), 6.71 (1H, s), 5.61 (1H, s), 4.66 (1H, d, J=6.1Hz), 4.11 (2H, q, J=7.1Hz), 3.86 (3H, s), 1.46 (6H, d, J=6.1Hz) 1.43 (3H, t, J=7.1Hz)

Mass spectrum (EI-MS) m/z (%): 402, 387, 359, 345

HRMS: $C_{21}H_{22}O_6S$ Calculated; 402.11370 Found; 402.11441

EXAMPLE 19

2.6 g of sodium sulfide hydrate (9 H2O), 340 g of sulfur, and 3 ml of water were stirred under heating. Following addition of an aqueous solution of sodium hydroxide (400 mg/10 ml water), the mixture was dissolved (sodium disulfide). 1.74 g of 3-chloro-4-methoxyaniline, 5 ml of water, 2 ml of conc. hydrochloric acid were mixed and cooled to 5° C., and an aqueous solution of sodium nitrite (690 mg/3 ml water) was added dropwise (diazonium salt). The diazonium salt solution was added little by little under stirring to the sodium disulfide solution having been cooled to 5° C. The solution was stirred for 2 hours with an increase in temperature by allowing to stand. Subsequently, water was added to the reaction solution, and the product was extracted twice with ethyl acetate. The organic layer was washed with saturated salt water and dried over sodium sulfate anhydride. The solvent was distilled out under reduced pressure. The resulting crude oil, 830 mg, was purified by flash column chromatography (hexane:ethyl acetate=15:1), whereby 503 mg of di(3-chloro-4-methoxyphenyl)disulfide was obtained.

324 mg of said di(3-chloro-4-methoxyphenyl)disulfide was dissolved in 10 ml of ethanol, followed by addition of 106 mg of sodium borohydride. The mixture was stirred over 2 hours at room temperature. The solution thus reacted was made weakly acidic by addition of dilute hydrochloric acid. The product was extracted twice with ethyl acetate. The organic layer was washed with saturated salt water and then dried over sodium sulfate anhydride. The solvent was distilled out under reduced pressure. The resulting crude product was purified by flash column chromatography (hexane:ethyl acetate=15:1), whereby 239 mg of 3-chloro-4-methoxybenzenethiol was obtained. 231 mg of the resulting 3-chloro-4-methoxybenzenethiol was dissolved in 4 ml dichloromethane, followed by cooling to 0° C. 4 ml of boron tribromide in dichloromethane was added dropwise under stirring. The mixture was stirred for 2 hours under cooling on ice and then for 20 hours at room temperature. Subsequently, under cooling on ice, water was added to the solution thus reacted, and the product was extracted twice with chloroform. The organic layer was washed with saturated salt water and dried over sodium sulfate anhydride. The solvent was distilled out, whereby 208 mg of crude 3-chloro-4-hydroxybenzenethiol was obtained.

A mixture consisting of 70 mg of 5,7-diisopropoxy-2-(4-isopropoxyphenoxy)-6-methoxychromone obtained in Example 4, 87 mg of 3-chloro-4-hydroxybenzenethiol, 150 mg of potassium carbonate, and 4 ml of acetone was stirred overnight at room temperature. The solution thus reacted was made weakly acidic by addition of dilute hydrochloric acid. The product was extracted twice with chloroform. The organic layer was washed with saturated salt water and then dried over sodium sulfate anhydride. The solvent was distilled out under reduced pressure. 153 mg of the resulting crystals containing impurities were purified by flash column chromatography (chloroform-chloroform:acetone=50:2), whereby 59 mg of 2-(3-chloro-4-hydroxyphenylthio)-5,7-diisopropoxy-6-methoxychromone with the following physicochemical properties was obtained.

Melting point: 230°–231° C.

Infrared absorption spectrum (IR, v max cm$^{-1}$, KBr): 2980, 1610, 1558, 1478, 1454, 1424, 1378, 1322, 1292, 1194, 1114

Proton nuclear magnetic resonance spectrum (δ ppm in CDCl$_3$): 7.58 (1H, d, J=2.2Hz), 7.29 (1H, dd, J=8.3, 2.2Hz), 7.00 (1H, d, J=8.3Hz), 6.66 (1H, s), 5.66 (1H, s), 4.65 (1H, d, J=6.1Hz), 4.50 (1H, d, J=6.1Hz), 3.84 (3H, s), 1.45 (6H, d, J=6.1Hz), 1.33 (6H, d, J=6.1Hz)

Mass spectrum (EI-MS) m/z (%): 450, 435, 408, 392, 365, 351

HRMS: $C_{22}H_{23}O_6ClS$ Calculated; 450.09038 Found; 450.09150

EXAMPLE 20

A mixture consisting of 506 mg of Capillarisin, 0.8 ml of isopropyl iodide, 1.10 g of potassium carbonate, and 25 ml of acetone was stirred over 2 days under reflux at a bath temperature of 60° C. Then, 1.0 ml of methyl iodide was added to the solution thus reacted, and the mixture was further refluxed overnight. Subsequently, water was added to the solution. The product was extracted twice with ethyl acetate. The organic layer was washed with saturated salt water and then dried over sodium sulfate anhydride. The solvent was distilled out under reduced pressure. The resulting oil, 608 mg, was purified by flash column chromatography (hexane:ethyl acetate=3:1), whereby 336 mg of 5,6-dimethoxy-7-isopropoxy-2-(4-isopropoxyphenoxy)chromone and 108 mg of 5,6-dimethoxy-7-isopropoxy-2-(4-methoxyphenoxy)chromone with the following physicochemical properties were respectively obtained.

(1) 5,6-dimethoxy-7-isopropoxy-2-(4-isopropoxyphenoxy)chromone

Melting point: 139°–140° C.

Infrared absorption spectrum (IR, ν max $cm^{-1}$, KBr): 2980, 1644, 1600, 1504, 1464, 1416, 1378, 1346, 1224, 1190, 1112

Proton nuclear magnetic resonance spectrum (δ ppm in $CDCl_3$): 7.07 (2H, d, J=8.8Hz), 6.91 (2H, d, J=8.8Hz), 6.68 (1H, s), 5.25 (1H, s), 4.63 (1H, h, J=6.2Hz), 4.53 (1H, h, J=6.2Hz), 3.94 (3H, s), 3.87 (3H, s), 1.44 (6H, d, J=6.2Hz), 1.36 (6H, d, J=6.2Hz)

Mass spectrum (EI-MS) m/z (%): 414, 399, 357, 315, 237

HRMS: $C_{23}H_{23}O_7$ Calculated; 414.16784 Found; 414.16733

(2) 5,6-dimethoxy-7-isopropoxy-2-(4-methoxyphenoxy)chromone

Melting point: 114°–115° C.

Infrared absorption spectrum (IR, ν max $cm^{-1}$, KBr): 2972, 2936, 1640, 1602, 1502, 1462, 1420, 1382, 1346, 1328, 1232, 1192, 1108, 1088, 1026, 822

Proton nuclear magnetic resonance spectrum (δ ppm in $CDCl_3$): 7.10 (2H, d, J=8.8Hz), 6.94 (2H, d, J=8.8Hz), 6.67 (1H, s), 5.24 (1H, s), 4.63 (1H, h, J=6.4Hz), 3.94 (3H, s), 3.87 (3H, s), 3.83 (3H, s), 1.44 (6H, d, J=6.4Hz)

Mass spectrum (EI-MS) m/z (%): 386, 371, 329, 280, 238, 223, 196

HRMS: $C_{21}H_{22}O_7$ Calculated; 386.13654 Found; 386.13575

EXAMPLE 21

A mixture consisting of 512 mg Capillarisin, 0.9 ml s-butyl iodide, 1.12 g potassium carbonate, and 25 ml acetone was stirred over 2 days under reflux at a bath temperature of 60° C. Then, 2.0 ml of methyl iodide was added to the solution thus reacted, and the mixture was further refluxed overnight. Subsequently, water was added to the solution. The product was extracted twice with ethyl acetate. The organic layer was washed with saturated salt water and then dried over sodium sulfate anhydride. The solvent was distilled out under reduced pressure. The resulting oil, 693 mg, was purified by flash column chromatography (hexane:ethyl acetate=3:1), whereby 205 mg of 7-s-butoxy-2-(4-s-butoxyphenoxy)-5,6-dimethoxychromone and 262 mg of 7-s-butoxy-5,6-dimethoxy-2-(4-methoxyphenoxy)chromone with the following physicochemical properties were respectively obtained.

(1) 7-s-butoxy-2-(4-s-butoxyphenoxy)-5,6-dimethoxychromone

Infrared absorption spectrum (IR, ν max $cm^{-1}$, KBr): 2976, 2936, 1642, 1604, 1502, 1462, 1416, 1384, 1352, 1222, 1188, 1110.

Proton nuclear magnetic resonance spectrum (δ ppm in $CDCl_3$): 7.07 (2H, d, J=9.3Hz), 6.91 (2H, d, J=9.3Hz), 6.67 (1H, s), 5.25 (1H, s), 4.40–4.20 (2H, m), 3.94 (3H, s), 3.87 (3H, s), 1.90–1.60 (4H, m), 1.39 (3H, d, J=6.4Hz), 1.31 (3H, t, J=5.9Hz), 1.03 (3H, t, J=7.3Hz), 0.99 (3H, t, J=7.3Hz)

Mass spectrum (EI-MS) m/z (%): 442, 427, 371, 315

HRMS: $C_{25}H_{30}O_7$ Calculated; 442.19914 Found; 442.19991

(2) 7-s-butoxy-5,6-dimethoxy-2-(4-methoxyphenoxy)chromone

Infrared absorption spectrum (IR, ν max $cm^{-1}$, KBr): 2972, 2936, 1640, 1604, 1504, 1462, 1418, 1380, 1344, 1226, 1186, 1110, 1026

Proton nuclear magnetic resonance spectrum (δ ppm in $CDCl_3$): 7.10 (2H, d, J=8.8Hz), 6.93 (2H, d, J=8.8Hz), 6.66 (1H, s), 5.24 (1H, s), 4.40 (1H, m), 3.94 (3H, s), 3.87 (3H, s), 3.83 (3H, s), 1.80 (2H, m), 1.39 (3H, d, J=5.9Hz), 1.03 (3H, t, J=7.8Hz)

Mass spectrum (EI-MS) m/z (%): 400, 385, 329

HRMS: $C_{22}H_{24}O_7$ Calculated; 400.15219 Found; 400.15136

EXAMPLE 22

A mixture consisting of 293 mg of 5,6-dimethoxy-7-isopropxy-2-(4-isopropoxyphenoxy)chromone obtained in Example 20, 179 mg of 4-hydroxybenzenethiol, 196 mg of potassium carbonate, and 5 ml of acetone was stirred overnight at room temperature. The solution thus reacted was made weakly acidic by addition of dilute hydrochloric acid. The product was extracted twice with chloroform. The organic layer was washed with saturated salt water and then dried over sodium sulfate anhydride. The solvent was distilled out under reduced pressure. The resulting crude oil, 501 mg, was recrystallized from 4 ml methanol, so that 194 mg of 5,6-dimethoxy-2-(4-hydroxyphenylthio)-7-isopropoxychromone with the following physicochemical properties was obtained.

Melting point: 213°–215° C.

Infrared absorption spectrum (IR, ν max $cm^{-1}$, KBr): 3230, 1612, 1578, 1498, 1482, 1468, 1440, 1418, 1322, 1278, 1220, 1190, 1112

Proton nuclear magnetic resonance spectrum (δ ppm in $CDCl_3$): 7.36 (2H, d, J=8.8Hz), 6.85 (2H, d, J=8.8Hz), 6.70 (1H, s), 5.64 (1H, s), 4.65 (1H, h, J=6.1Hz), 3.92 (3H, s), 3.86 (3H, s), 1.45 (6H, d, J=6.1Hz)

Mass spectrum (EI-MS) m/z (%): 388, 373, 331

HRMS: $C_{20}H_{20}O_6S$ Calculated; 388.09805 Found; 388.09759

EXAMPLE 23

A mixture consisting of 258 mg of 7-s-butoxy-5,6-dimethoxy-2-(4-methoxyphenoxy)chromone obtained in Example 21, 163 mg of 4-hydroxythiophenol, 173 mg of potassium carbonate, and 5 ml of acetone was stirred overnight at room temperature. The solution thus reacted was made weakly acidic by addition of dilute hydrochloric acid. The product was extracted twice with chloroform. The organic layer was washed with saturated salt water and then dried over sodium sulfate anhydride. The solvent was distilled out under reduced pressure. The resulting crude oil was purified by flash column chromatography (hexane:ethyl acetate=2:1), whereby 172 mg of 7-s-butoxy-5,6-dimethoxy-2-(4-hydroxyphenylthio)chromone with the following physicochemical properties was obtained.

Melting point: 207°–209° C.

Infrared absorption spectrum (IR, ν max $cm^{-1}$, KBr): 3100, 2976, 2936, 1612, 1576, 1496, 1464, 1418, 1350, 1328, 1286, 1192, 1166, 1114, 832

Proton nuclear magnetic resonance spectrum (δ ppm in CDCl$_3$): 7.36 (2H, d, J=8.8Hz), 6.85 (2H, d, J=8.8Hz), 6.69 (1H, s), 5.64 (1H, s), 4.50–4.35 (1H, m), 3.93 (3H, s), 3.86 (3H, s), 1.95–1.65 (2H, m), 1.40 (3H, d, J=6.1Hz), 1.04 (3H, t, J=7.1Hz)

Mass spectrum (EI-MS) m/z (%): 402, 387, 331

HRMS: C$_{21}$H$_{22}$O$_6$S Calculated; 402.11370 Found; 401.11404

EXAMPLE 24

A mixture consisting of 206 mg of Capillarisin, 982 mg of 3-bromopentane, 449 mg of potassium carbonate, and 10 ml of acetone was stirred for 2 days under reflux at a bath temperature of 60° C. Methyl iodide was added to the solution thus reacted, and the mixture was further refluxed overnight. Subsequently, water was added to the reaction solution. The product was extracted twice with ethyl acetate. The organic layer was washed with saturated salt water and then dried over sodium sulfate anhydride. The solvent was distilled out under reduced pressure. The resulting oil was purified by flash column chromatography (hexane:ethyl acetate=3:1), whereby 46 mg of 5,6-dimethoxy-7-(1-ethylpropoxy)-2-[4-(1-ethylpropoxy)phenoxy]chromone and 23 mg of 5,6-dimethoxy-7-(1-ethylpropoxy)-2-(4-methoxyphenoxy)chromone with the following physicochemical properties were respectively obtained.

(1) 5,6-dimethoxy-7-(1-ethylpropoxy)-2-[4-(1-ethylpropoxy)phenoxy]chromone

Proton nuclear magnetic resonance spectrum (δ ppm in CDCl$_3$): 7.06 (2H, d, J=9.3Hz), 6.92 (2H, d, J=9.3Hz), 6.66 (1H, s), 5.24 (1H, s), 4.22 (1H, q, J=5.9Hz), 4.09 (1H, q, J=5.9Hz), 3.94 (3H, s), 3.87 (3H, s), 1.85–1.62 (8H, m), 1.01 (6H, t, J=7.3Hz), 0.97 (6H, t, J=7.3Hz)

Mass spectrum (EI-MS) m/z (%): 470, 455, 385, 356, 315

HRMS: C$_{27}$H$_{34}$O$_7$ Calculated; 470.23044 Found; 470.23264

(2) 5,6-dimethoxy-7-(1-ethylpropoxy)-2-(4-methoxyphenoxy)chromone

Proton nuclear magnetic resonance spectrum (δ ppm in CDCl$_3$): 7.10 (2H, d, J=9.3Hz), 6.93 (2H, d, J=9.3Hz), 6.66 (1H, s), 5.23 (1H, s), 4.22 (1H, q, J=5.7Hz), 3.94 (3H, s), 3.87 (3H, s), 3.83 (3H, s), 1.86–1.71 (4H, m), 1.01 (6H, t, J=7.4Hz)

Mass spectrum (EI-MS) m/z (%): 414, 399, 329

HRMS: C$_{23}$H$_{26}$O$_7$ Calculated; 414.16784 Found; 414.16789

EXAMPLE 25

A mixture consisting of 59 mg of a mixture of 5,6-dimethoxy-7-(1-ethylpropoxy)-2-[4-(1-ethylpropoxy)phenoxy]chromone and 5,6-dimethoxy-7-(1-ethylpropoxy)-2-(4-methoxyphenoxy)chromone, 33 mg of 4-hydroxythiophenol, 36 mg of potassium carbonate, and 2 ml of acetone was stirred overnight at room temperature. The solution thus reacted was made weakly acidic by addition of dilute hydrochloric acid. The product was extracted twice with chloroform. The organic layer was washed with saturated salt water and then dried over sodium sulfate anhydride. The solvent was distilled out under reduced pressure. The resulting crude oil, 124 mg, was purified by flash column chromatography (chloroform:methanol=70:1), whereby 50 mg of 5,6-dimethoxy-7-(1-ethylpropoxy)-2-(4-hydroxyphenylthio)chromone with the following physicochemical properties was obtained.

Proton nuclear magnetic resonance spectrum (δ ppm in CDCl$_3$): 7.34 (2H, d, J=8.6Hz), 6.86 (2H, d, J=8.6Hz), 6.69 (1H, s), 5.64 (1H, s), 4.26 (1H, q, J=5.9Hz), 3.94 (3H, s), 3.87 (3H, s), 1.80 (4H, m), 1.01 (6H, t, J=7.3Hz)

Mass spectrum (EI-MS) m/z (%): 416, 401, 345, 331

HRMS: C$_{22}$H$_{24}$O$_6$S Calculated; 416.12935 Found; 416.12841

EXAMPLE 26

A mixture consisting of 9.49 g of 5-hydroxy-7-isopropoxy-2-(4-isopropoxyphenoxy)-6-methoxychromone obtained in Example 4, 4.49 g of 4-hydroxythiophenol, 4.91 g of potassium carbonate, and 200 ml of acetone was stirred over 1.2 hours at room temperature. The solution thus reacted was made weakly acidic by addition of dilute hydrochloric acid. The product was extracted twice with chloroform. The organic layer was washed with saturated salt water and was then dried over sodium sulfate anhydride. The solvent was distilled out under reduced pressure. The resulting crude product was recrystallized from hexane-ethyl acetate, so that 7.95 g of 5-hydroxy-2-(4-hydroxyphenylthio)-7-isopropoxy-6-methoxychromone with the following physicochemical properties was obtained.

Melting point: 185°–186° C.

Infrared absorption spectrum (IR, ν max cm$^{-1}$, KBr): 1658, 1596, 1582, 1462, 1340, 1326, 1114

Proton nuclear magnetic resonance spectrum (δ ppm in CDCl$_3$): 12.19 (1H, S), 8.25 (1H, br s), 7.40 (2H, d, J=8.8Hz), 6.87 (2H, d, J=8.8Hz), 6.45 (1H, s), 5.59 (1H, s), 4.65 (1H, m), 3.87 (3H, s) 1.44 (6H, d, J=6.3Hz), Mass spectrum (EI-MS) m/z (%): 374, 317

Elemental analysis: C$_{19}$H$_{18}$O$_6$S Calculated; C:60.95, H:4.85 Found; C:60.88, H:5.02

EXAMPLE 27

(1) A mixture consisting of 1.36 g of Capillarisin, 4.13 g of 4-[(t-butyldimethylsilyl)oxy]benzenethiol, 2.37 g of potassium carbonate, 40 ml of acetone was stirred over 3 hours at room temperature. Subsequently, water was added to the solution thus reacted. The solution was made weakly acidic by addition of dilute hydrochloric acid. The product was extracted twice with ethyl acetate. The organic layer was washed with saturated salt water and then dried over sodium sulfate anhydride. The solvent was distilled out under reduced pressure. The resulting oil was purified by flash column chromatography (hexane:ethyl acetate=6:1), whereby 683 mg of 2-{4-[(t-butyldimethylsilyl)oxy]phenylthio}-5,7-dihydroxy-6-methoxychromone with the following physicochemical properties was obtained.

Infrared absorption spectrum (IR, ν max cm$^{-1}$, neat): 3352, 2952, 2932, 2856, 1650, 1608, 1588, 1494, 1462, 1434, 1358, 1266, 1160, 1108, 908, 832

Proton nuclear magnetic resonance spectrum (δ ppm in acetone-d$_6$): 12.91 (1H, s), 7.62 (2H, d, J=8.8Hz), 7.09 (2H, d, J=8.8Hz), 6.40 (1H, s), 5.60 (1H, s), 3.84 (3H, s), 1.02 (9H, s), 0.29 (6H, s)

Mass spectrum (EI-MS) m/z (%): 446, 431, 389, 371, 250

HRMS: C$_{22}$H$_{26}$O$_6$SSi Calculated; 446.12193 Found; 446.12178

1.07 ml of acetic acid anhydride was added to a mixture of 510 mg of 2-{4-[(t-butyldimethylsilyl)oxy]phenylthio}-

5,7-dihydroxy-6-methoxychromone obtained in (1) above, 1.58 ml of triethylamine, 139 mg of 4-dimethylaminopyridine (DMAP), and 20 ml of chloroform. The mixture was stirred over 4 hours at room temperature. Subsequently, water was added to the solution thus reacted. The product was extracted twice with chloroform. The organic layer was washed with saturated salt water and then dried over sodium sulfate anhydride. The solvent was distilled out under reduced pressure. The resulting oil, 696 mg, was purified by flash column chromatography (hexane:ethyl acetate=5:1), whereby 430 mg of 5,7-diacetoxy-2-{4-[(t-butyldimethylsilyl)oxy]phenylthio}-6-methoxychromone with the following physicochemical properties was obtained.

Infrared absorption spectrum (IR, ν max $cm^{-1}$, neat): 2952, 2936, 1780, 1644, 1622, 1590, 1492, 1478, 1428, 1320, 1266, 1184, 1156, 1076, 908, 838

Proton nuclear magnetic resonance spectrum (δ ppm in $CDCl_3$): 7.44 (2H, d, J=8.8Hz), 7.05 (1H, s), 6.90 (2H, d, J=8.8Hz), 5.70 (1H, s), 3.83 (3H, s), 2.42 (3H, s), 2.36 (3H, s), 1.00 (9H, s), 0.24 (6H, s)

Mass spectrum (EI-MS) m/z (%): 530, 488, 446, 431, 416, 3389

HRMS: $C_{26}H_{30}O_8SSi$ Calculated; 530.14305 Found; 530.14114

EXAMPLE 28

2 ml of 46% aqueous hydrogen fluoride (HF) solution was added to 8 ml in acetonitrile of 430 mg of 5,7-diacetoxy-2-{4-[(t-butyldimethylsilyl)oxy]phenylthio}-6-methoxychromone obtained in Example 27, followed by stirring for 1 hour at room temperature. Then, water was added to the solution thus reacted. The product was extracted twice with ethyl acetate. The organic layer was washed with saturated salt water and then dried over sodium sulfate anhydride. The solvent was distilled out under reduced pressure. The resulting oil, 312 mg, was purified by flash column chromatography (hexane:ethyl acetate=8:5), whereby 108 mg of 5,7-diacetoxy-2-(4-hydroxyphenylthio)-6-methoxychromone and 125 mg of 7-acetoxy-5-hydroxy-2-(4-hydroxyphenylthio)-6-methoxychromone with the following physicochemical properties were respectively obtained.

(1) 5,7-diacetoxy-2-(4-hydroxyphenylthio)-6-methoxychromone

Melting point: 189°–190° C.

Infrared absorption spectrum (IR, ν max $cm^{-1}$, KBr): 1780, 1614, 1582, 1550, 1478, 1454, 1428, 1364, 1330, 1278, 1190, 1158, 1110, 1078

Proton nuclear magnetic resonance spectrum (δ ppm in $CDCl_3$): 5.61 (1H, s), 3.85 (3H, s), 2.40 (3H, s), 2.38 (3H, s)

Mass spectrum (EI-MS) m/z (%): 416, 375, 359, 332, 317, 314

HRMS: $C_{20}H_{16}O_8S$ Calculated; 416.0562 Found; 416.0559

(2) 7-acetoxy-5-hydroxy-2-(4-hydroxyphenylthio)-6-methoxychromone

Melting point: 159°–160° C.

Infrared absorption spectrum (IR, ν max $cm^{-1}$, KBr): 1776, 1610, 1584, 1564, 1454, 1432, 1330, 1286, 1192, 1158, 1086, 834

Proton nuclear magnetic resonance spectrum (δ ppm in $CDCl_3$): 12.54 (1H, s), 7.80 (1H, br s), 7.41 (2H, d, J=8.3Hz), 6.87 (2H, d, J=8.3Hz), 5.67 (1H, s), 3.91 (3H, s), 2.37 (3H, s)

Mass spectrum (EI-MS) m/z (%): 374, 332, 317, 318, 314, 276, 234

HRMS: $C_{18}H_{14}O_7S$ Calculated; 374.0460 Found; 374.0460

EXAMPLE 29

A mixture consisting of 303 mg of Capillarisin, 1.43 g of prenyl bromide, 662 mg of potassium carbonate, 478 mg of potassium iodide, and 8 ml of acetone was stirred over 20 hours under reflux at a bath temperature of 60 C. Subsequently, water was added to the solution thus reacted. The product was extracted twice with ethyl acetate. The organic layer was washed with saturated salt water and then dried over sodium sulfate anhydride. The solvent was distilled out under reduced pressure. The resulting oil was purified by flash column chromatography (hexane:ethyl acetate=7:1), whereby 80 mg of 5-hydroxy-6-methoxy-7-prenyloxy-2-(4-prenyloxyphenoxy)chromone with the following physicochemical properties was obtained.

Melting point: 136 137° C.

Infrared absorption spectrum (IR, ν max $cm^{-1}$, KBr): 1658, 1606, 1564, 1504, 1492, 1454, 1412, 1366, 1296, 1226, 1188, 1110, 1096, 990, 856, 834

Proton nuclear magnetic resonance spectrum (δ ppm in $CDCl_3$): 12.68 (1H, br s), 7.09 (2H, d, J=8.9Hz), 6.96 (2H, d, J=8.9Hz), 6.43 (1H, s), 5.50 (2H, m), 5.25 (1H, s), 4.64 (2H, d, J=6.4Hz), 4.53 (2H, d, J=6.4Hz), 3.89 (3H, s), 1.82 (6H, br s), 1.77 (6H, br s), Mass spectrum (EI-MS) m/z (%): 452, 384, 316, 298

HRMS: $C_{26}H_{28}O_7$ Calculated; 452.18349 Found; 452.18273

EXAMPLE 30

A mixture consisting of 66 mg of 5-hydroxy-6-methoxy-7-prenyloxy-2-(4-prenyloxyphenoxy)chromone obtained in Example 29, 0.36 ml of ethyl iodide, 62 mg of potassium carbonate, and 3 ml of acetone was stirred over 20 hours under reflux at a bath temperature of 60° C. Subsequently, water was added to the solution thus reacted. The product was extracted twice with ethyl acetate. The organic layer was washed with saturated salt water and then dried over sodium sulfate anhydride. The solvent was distilled out under reduced pressure. The resulting oil was purified by flash column chromatography (hexane:ethyl acetate=5:1), whereby 51 mg of 5-ethoxy-6-methoxy-7-prenyloxy-2-(4-prenyloxyphenoxy)chromone with the following physicochemical properties was obtained.

Melting point: 119°–120° C.

Infrared absorption spectrum (IR, ν max $cm^{-1}$, KBr): 1638, 1604, 1504, 1454, 1396, 1378, 1360, 1222, 1182, 1116, 1024

Proton nuclear magnetic resonance spectrum (δ ppm in $CDCl_3$): 7.08 (2H, d, J=9.3Hz), 6.94 (2H, d, 9.3Hz), 6.67 (1H, s), 5.50 (2H, m), 5.34 (1H, s), 4.64 (2H, d, J=7.0Hz), 4.52 (2H, d, J=7.0Hz), 4.12 (2H, q, J=6.8Hz), 3.88 (3H, s), 1.82 (6H, br s), 1.77 (6H, br s), 1.44 (3H, t, J=6.8Hz)

Mass spectrum (EI-MS) m/z (%): 480, 465, 411, 387, 329

HRMS: $C_{28}H_{32}O_7$ Calculated; 480.21479 Found; 480.21601

EXAMPLE 31

A mixture consisting of 43 mg of 5-ethoxy-6-methoxy-7-prenyloxy-2-(4-prenyloxyphenoxy)chromone obtained in Example 30, 23 mg of 4-hydroxythiophenol, 25 mg of potassium carbonate, and 2 ml of acetone was stirred over 2 hours at room temperature. Subsequently, water was added to the solution thus reacted. The solution was made weakly acidic with dilute hydrochloric acid. The product was extracted twice with ethyl acetate. The organic layer was washed with saturated salt water and then dried over sodium sulfate anhydride. The solvent was distilled out under reduced pressure. The resulting oil was purified by flash column chromatography (chloroform:methanol=100:1), whereby 33 mg of 5-ethoxy-2-(4-hydroxyphenylthio)-6-methoxy-7-prenyloxychromone with the following physicochemical properties was obtained.

Melting point: 189°–190° C.

Infrared absorption spectrum (IR, ν max cm$^{-1}$, KBr): 3420, 1614, 1574, 1454, 1426, 1326, 1288, 1186, 1168, 1112

Proton nuclear magnetic resonance spectrum (δ ppm in CDCl$_3$): 7.35 (2H, d, J=8.8Hz), 6.85 (2H, d, 8.8Hz), 6.71 (1H, s), 5.63 (1H, s), 5.55 (1H, br t), 4.65 (2H, d, J=6.4Hz), 4.11 (2H, q, J=7.1Hz), 3.88 (3H, s), 1.82 (3H, br s), 1.78 (3H, br s) 1.43 (3H, t, J=7.1Hz)

Mass spectrum (EI-MS) m/z (%): 428

EXAMPLE 32

A mixture consisting of 10.38 g Capillarisin, 20.40 ml of 3-bromopentane, 27.20 g of potassium carbonate, 5.45 g of potassium iodide, and 250 ml of acetone was stirred over 3 days under reflux. Subsequently, water was added to the solution thus reacted. The product was extracted twice with ethyl acetate. The organic layer was washed with saturated salt water and then dried over sodium sulfate anhydride. The solvent was distilled out under reduced pressure. The resulting crude product was purified by flash column chromatography (hexane:ethyl acetate=2:1), whereby 7.45 g of 7-(1-ethoxypropoxy)-2-[4-(1-ethoxypropoxy)phenoxy]-5-hydroxy-6-methoxychromone and 2.02 g of 7-(1-ethoxypropoxy)-5-hydroxy-2-(4-hydroxyphenoxy)-6-methoxychromone with the following physicochemical properties were respectively obtained.

(1) 7-(1-ethoxypropoxy)-2-[4-(1-ethoxypropoxy)phenoxy]-5-hydroxy-6-methoxychromone Proton nuclear magnetic resonance spectrum (δ ppm in CDCl$_3$): 12.65 (1H, s), 7.07 (2H, d, J=9.3Hz), 6.93 (2H, d, J=9.3Hz), 6.41 (1H, s), 5.24 (1H, s), 4.30–4.05 (2H, m), 3.88 (3H, s), 1.90–1.60 (8H, m), 1.05–0.95 (12H, m)

Mass spectrum (EI-MS) m/z (%): 456 (M$^+$), 426, 386, 316, 298

(2) 7-(1-ethoxypropoxy)-5-hydroxy-2-(4-hydroxyphenoxy)-6-methoxychromone

Proton nuclear magnetic resonance spectrum (δ ppm in CDCl$_3$): 12.34 (1H, s), 6.98 (2H, d, J=8.8Hz), 6.84 (2H, d, J=8.8Hz), 6.46 (1H, s), 5.17 (1H, s), 4.24 (1H, m), 3.89 (3H, s), 1.78 (4H, m), 1.00 (6H, t, J=7.3Hz)

Mass spectrum (EI-MS) m/z (%): 386 (M$^+$), 330

EXAMPLE 33

3.51 g of 4-hydroxybenzenethiol, 3.84 g of potassium carbonate, and 120 ml of acetone were added to 6.09 g 7-(1-ethoxypropoxy)-2-[4-(1-ethoxypropoxy)phenoxy]-5-hydroxy-6-methoxychromone and 2.01 g of 7-(1-ethoxypropoxy)-5-hydroxy-2-(4-hydroxyphenoxy)-6-methoxychromone obtained in Example 32. The mixture was was stirred over 4 hours at room temperature. The solution thus reacted was made weakly acidic by addition of dilute hydrochloric acid. The product was extracted twice with chloroform. The organic layer was washed with saturated salt water, followed by drying over sodium sulfate anhydride. The solvent was distilled out under reduced pressure. The resulting residues were purified by flash column chromatography (hexane:ethyl acetate=4:1) and then subjected to recrystallization from hexane-ethyl acetate, so that 4.63 g of 7-(1-ethylpropoxy)-5-hydroxy-2-(4-hydroxyphenylthio)-6-methoxychromone with the following physicochemical properties was obtained.

Melting points: 170°–171° C.

Infrared absorption spectrum (IR, ν max cm$^{-1}$, KBr): 3280, 2968, 2936, 1652, 1598, 1456 1334, 1114

Proton nuclear magnetic resonance spectrum (δ ppm in CDCl$_3$): 12.20 (1H, s), 7.40 (2H, d, J=8.8Hz), 6.88 (2H, d, J=8.8Hz), 6.43 (1H, s), 5.59 (1H, s), 4.24 (1H, m), 3.87 (3H, s), 1.77 (4H, m), 1.00 (6H, t, J=7.3Hz)

Mass spectrum (EI-MS) m/z (%): 402 (M$^+$), 332, 317, 314

EXAMPLE 34

96 mg of m-chloroperbenzoic acid (mCPBA) was added under cooling on ice to 4 ml in chloroform of 107 mg of 5,6-dimethoxy-2-(4-hydroxyphenylthio)-7-isopropoxychromone obtained in Example 22. The solution was stirred for 2 hours at room temperature. Subsequently, water was added to the solution thus reacted. The product was extracted twice with ethyl acetate. The organic layer was washed with saturated salt water and then dried over sodium sulfate anhydride. The solvent was distilled out under reduced pressure. The resulting oil, 142 mg, was purified by flash column chromatography (chloroform:acetone=30:1), whereby 52 mg of 5,6-dimethoxy-2-(4-hydroxyphenylsulfinyl)-7-isopropoxychromone and 56 mg of 5,6-dimethoxy-2-(4-hydroxyphenylsulfonyl)-7-isopropoxychromone with the following physicochemical properties were respectively obtained.

(1) 5,6-dimethoxy-2-(4-hydroxyphenylsulfinyl)-7-isopropoxychromone

Melting points: 178°–179° C.

Infrared absorption spectrum (IR, ν max cm$^{-1}$, KBr): 3284, 1636, 1598, 1582, 1482, 1464, 1418, 1338, 1322, 1194, 1114, 1086

Proton nuclear magnetic resonance spectrum (δ ppm in CDCl$_3$): 7.60 (2H, d, J=8.6Hz), 7.00 (2H, d, 8.6Hz), 6.80 (1H, s), 6.60 (1H, s), 4.64 (1H, h, 6.1Hz), 3.94 (3H, s), 3.83 (3H, s), 1.42 (3H, d, J=6.1Hz), 1.40 (3H, d, J=6.1Hz)

Mass spectrum (FD-MS) m/z (%): 404

HRMS [EI]: C$_{20}$H$_{20}$O$_7$S Calculated; 404.09296 Found; 404.09413

(2) 5,6-dimethoxy-2-(4-hydroxyphenylsulfonyl)-7-isopropoxychromone

Melting points: 180°–181° C.

Infrared absorption spectrum (IR, ν max cm$^{-1}$, KBr): 1640, 1600, 1582, 1480, 1466, 1420, 1364, 1344, 1294, 1268, 1196, 1180, 1156, 1108, 1084, 1006

Proton nuclear magnetic resonance spectrum (δ ppm in CDCl$_3$): 7.87 (2H, d, J=8.8Hz), 7.04 (2H, d, J=8.8Hz), 6.89

(1H, s), 6.70 (s, 1H), 4.66 (1H, h, J=6.1Hz), 3.93 (3H, s), 3.83 (3H, s), 1.44 (6H, d, J=6.1 Hz)

Mass spectrum (EI-MS) m/z (%): 420, 405, 377, 363

HRMS: $C_{20}H_{20}O_8S$ Calculated; 420.08788 Found; 420.08629

EXAMPLE 35

300 ml in dichloromethane of 9.11 g of 5,6-dimethoxy-2-(4-hydroxyphenylthio)-7-isopropoxychromone obtained in Example 22, 4.52 g of N-t-butoxycarbonyl(Boc)glycine, and 5.32 g of dicyclohexylcarbodiimide (DCC) was stirred over 3.5 hours at room temperature. The solution thus reacted was gravitationally filtered. The solvent was distilled out from the filtrate, so that 10.95 g of N-t-butoxycarbonyl (Boc)glycine ester was obtained. 5.27 g of N-t-butoxycarbonyl(Boc)glycine ester thus prepared was dissolved in 100 ml of ethyl acetate. Then, hydrochloric acid gas was introduced and bubbled in the solution for 10 min., followed by stirring for 1 hour. Subsequently, 200 ml ether was added and the resulting crystals were collected by filtration and then dried, whereby 3.53 g of 5,6-dimethoxy-2-(4-glycyloxyphenylthio)-7-isopropoxychromone hydrochloride with the following physicochemical properties was obtained.

Melting points: 84°–85° C.

Infrared absorption spectrum (IR, $\nu$ max $cm^{-1}$, KBr): 2976, 2936, 1776, 1612, 1588, 1482, 1462, 1418, 1320, 1196, 1110

Proton nuclear magnetic resonance spectrum ($\delta$ ppm in $CD_3OD$): 7.77 (2H, d, J=8.8Hz), 7.41 (2H, d, J=8.8Hz), 6.86 (1H, s), 5.71 (1H, s), 4.76 (1H, m), 4.18 (2H, s), 3.86 (3H, s), 3.82 (3H, s), 1.40 (6H, d, J=6.1Hz)

Mass spectrum (FAB-MS) m/z (%): 402 ($M^+$-HCl+1)

EXAMPLE 36

300 ml in dichloromethane of 11.35 g of 5-ethoxy-2-(4-hydroxyphenylthio)-7-isopropoxy-6-methoxychromone obtained in Example 18, 5.43 g of N-t-butoxycarbonyl(Boc)glycine, and 6.40 g of dicyclohexylcarbodiimide (DCC) was stirred over 5.5 hours at room temperature. The solution thus reacted was gravitationally filtered. The solvent was distilled out from the filtrate, so that N-t-butoxycarbonyl(Boc)glycine ester was obtained. This product was dissolved in 100 ml of ethyl acetate. Then, hydrochloric acid gas was introduced and bubbled in the solution for 10 min., followed by stirring for 1 hour. Subsequently, 200 ml ether was added and the resulting crystals were collected by filtration and dried, whereby 11.28 g of 5-ethoxy-2-(4-glycyloxyphenylthio)-7-isopropoxy-6-methoxychromone hydrochloride with the following physicochemical properties was obtained.

Melting points: 105°–110° C.

Infrared absorption spectrum (IR, $\nu$ max $cm^{-1}$, KBr): 2976, 2932, 1776, 1642, 1610, 1588, 1480, 1452, 1426, 1392, 1316, 1260, 1200, 1108, 1016

Proton nuclear magnetic resonance spectrum ($\delta$ ppm in $CD_3OD$): 7.77 (2H, d, J=9.0Hz), 7.41 (2H, d, J=9.0Hz), 6.85 (1H, s), 5.74 (1H, s), 4.75 (1H, m), 4.20 (2H, s), 4.05 (2H, q, J=7.1Hz), 3.82 (3H, s), 1.40 (6H, d, J=5.4Hz), 1.39 (3H, t, J=7.1Hz)

Mass spectrum (FAB-MS) m/z (%): 460 ($M^+$-Cl)

EXAMPLE 37

300 ml in dichloromethane of 5.66 g of 5,6-dimethoxy-7-(1-ethylpropoxy)-2-(4-hydroxyphenylthio)chromone obtained in Example 25, 2.62 g of N-t-butoxycarbonyl(Boc) glycine, and 3.08 g of 1,3-dicyclohexylcarbodiimide (DCC) was stirred over 5.5 hours at room temperature. The solution thus reacted was gravitationally filtered. The solvent was distilled out from the filtrate, so that N-t-butoxycarbonyl (Boc)glycine ester was obtained. This product was dissolved in 100 ml of ethyl acetate. Then, hydrochloric acid gas was introduced and bubbled in the solution for 10 min., followed by stirring for 3 hours. Subsequently, 200 ml ether was added and the resulting crystals were collected by filtration and dried, whereby 6.44 g of 7-(1-ethylpropoxy)-5,6-dimethoxy-2-(4-glycyloxyphenylthio)chromone hydrochloride with the following physicochemical properties was obtained.

Melting points: 95°–100° C.

Infrared absorption spectrum (IR, $\nu$ max $cm^{-1}$, KBr): 2968, 2936, 2880, 1778, 1612, 1480, 1462, 1416, 1324, 1192, 1108, 1014

Proton nuclear magnetic resonance spectrum ($\delta$ ppm in $CD_3OD$): 7.77 (2H, d, J=d, 8.8Hz), 7.42 (2H, d, J=d, 8.8Hz), 6.85 (1H, s), 5.76 (1H, s), 4.41 (1H, m), 4.19 (2H, s), 3.87 (3H, s), 3.85 (3H, s), 1.76(4H, m), 0.99 (3H, t, J=7.5Hz)

Mass spectrum (FAB-MS) m/z (%): 474 ($M^+$-Cl)

EXAMPLE 38

15 ml in dichloromethane of 350 mg of 5-ethoxy-2-(4-hydroxyphenylthio)-7-isopropoxy-6-methoxychromone obtained in Example 18, 268 mg of $\alpha$-t-butoxy N-t-butoxycarbonyl-L-aspartate, and 198 mg of dicyclohexylcarbodiimide (DCC) was stirred over 20 hours at room temperature. The solution thus reacted was gravitationally filtered. The solvent was distilled out from the filtrate, whereby aspartate was obtained.

308 mg of the resulting aspartate was dissolved in 15 ml ethyl acetate. Under cooling on ice, hydrochloric acid gas was introduced and bubbled in the solution for 5 min. Then, the reaction vessel was sealed, followed by stirring for 1 hour at room temperature. The solution thus reacted was concentrated, and ether was added. The resulting crystals were collected by filtration and dried, whereby 197 mg of 2-(4-$\beta$-aspartyloxyphenylthio)-5-ethoxy-7-isopropoxy-6-methoxychromone hydrochloride with the following physicochemical properties was obtained.

Melting points: 106°–108° C.

Infrared absorption spectrum (IR, $\nu$ max $cm^{-1}$, KBr): 2976, 2932, 1754, 1640, 1612

Proton nuclear magnetic resonance spectrum ($\delta$ ppm in $CD_3OD$): 7.73 (2H, d, J=8.8Hz), 7.38 (2H, d, J=8.8Hz), 6.84 (1H, s), 5.72 (1H, s), 4.78 (1H, m), 4.50 (1H, m), 4.05 (2H, q, J=7.1 Hz), 3.82 (3H, s), 3.38 (2H, m), 1.40 (6H, d, J=6.0 Hz), 1.39 (3H, t, J=7.1 Hz) Mass spectrum (FAB-MS) m/z (%): 518 ($M^+$-Cl)

EXAMPLE 39

150 ml in dichloromethane of 4.09 g of 5,6-dimethoxy-7-(1-ethylpropoxy)-2-(4-hydroxyphenylthio)chromone obtained in Example 25, 6.39 g of 4-(4-methylpiperazinomethyl)benzoxychloride dihydrochloride, and 6.89 ml of triethylamine was stirred over 3 hours at room temperature. The solution thus reacted was concentrated, and an aqueous solution of sodium bicarbonate was added to the resulting residues, and then the product was extracted with ethyl acetate. The organic layer was concentrated, and the residues thus obtained were purified by flash column chromatography (chloroform:methanol=

30:1), whereby 2.04 g of 5,6-dimethoxy-7-(1-ethylpropoxy)-2-{4-[4-(4-methylpiperazinomethyl)benzoyloxy]phenylthio}chromone with the following physicochemical properties was obtained.

Proton nuclear magnetic resonance spectrum (δppm in CDCl$_3$): 8.15 (2H, d, J=8.3 Hz), 7.66 (2H, d, J=8.8 Hz), 7.50 (2H, d, J=8.3 Hz), 7.33 (2H, d, J=8.8 Hz), 6.58 (1H, s), 5.88 (1H, s), 4.23 (1H, m), 3.93 (3H, s), 3.86 (3H, s), 3.61 (2H, s), 2.51 (8H, br s), 2.31 (3H, s), 1.77 (4H, m), 1.00 (6H, t, J=7.3 Hz) Mass spectrum (FAB-MS) m/z (%): 633 (MH$^+$), 563

2.03 g of 5,6-dimethoxy-7-(1-ethylpropoxy)-2-{4-[4-(4-methylpiperazinomethyl)benzoyloxy]phenylthio}chromone thus obtained was dissolved in 30 ml ether. 20% hydrochloric acid-ethanol was added, and the solution was stirred over 20 min., under cooling on ice. The resulting crystals were collected by filtration and dried, whereby 1.67 g of 5,6-dimethoxy-7-(1-ethylpropoxy)-2-{4-[4-(4-methylpiperazinomethyl)benzoyloxy]phenylthio}chromone dihydrochloride with the following physicochemical properties was obtained.

Melting points: 178°–183° C. Infrared absorption spectrum (IR, vmax cm$^{-1}$, KBr): 2968, 2936, 1742, 1638, 1612 Proton nuclear magnetic resonance spectrum (δppm in CD$_3$OD): 8.30 (2H, d, J=8.3 Hz), 7.85 (2H, d, J=8.3 Hz), 7.78 (2H, d, J=8.8 Hz) 7.45 (2H, d, J=8.8 Hz), 6.83 (1H, s), 5.81 (1H, s), 4.58 (2H, s), 4.42 (1H, m), 3.87 (3H, s), 3.85 (3H, s), 3.70 (8H, br s), 3.03 (3H, s), 1.76 (4H, m), 0.99 (6H, t, J=7.3 Hz) High resolution mass spectrum (HR-FAB-MS): C$_{35}$H$_{41}$O$_7$N$_2$S Calculated; 633.26345 Found; 633.26341

EXAMPLE 40

150 ml in dichloromethane of 4.46 g of 7-(1-ethylpropoxy)-5-hydroxy-2-(4-hydroxyphenylthio)-6-methoxychromone obtained in Example 33, 7.21 g of 4-(4-methylpiperazinomethyl)benzoxychloride dihydrochloride, 7.78 ml of triethylamine was stirred over 3 hours at room temperature. The solution thus reacted was concentrated, and an aqueous solution of sodium bicarbonate was added to the resulting residues, and the product was extracted with ethyl acetate. The organic layer was concentrated, and the residues thus obtained were purified by flash column chromatography (chloroform:methanol=30:1), whereby 2.31 g of 7-(1-ethylpropoxy)-5-hydroxy-2-{4-[4-(4-methylpiperazinomethyl)benzoyloxy]phenylthio}-6-methoxychromone was obtained.

2.30 g of 7-(1-ethylpropoxy)-5-hydroxy-2-{4-[4-(4-methylpiperazinomethyl)benzoyloxy]phenylthio}-6-methoxychromone was dissolved in 30 ml ether, 20% hydrochloric acid-ethanol was added, and the solution was stirred over 20 min., under cooling on ice. The resulting crystals were collected by filtration and dried, whereby 2.35 g of 7-(1-ethylpropoxy)-5-hydroxy-2-{4-[4-(4-methylpiperazinomethyl)benzoyloxy]phenylthio}-6-methoxychromone dihydrochloride with the following physicochemical properties was obtained.

(1) 7-(1-ethylpropoxy)-5-hydroxy-2-{4-[4-(4-methylpiperazinomethyl)benzoyloxy]phenylthio}-6-methoxychromone Proton nuclear magnetic resonance spectrum (δppm in CDCl$_3$): 12.47 (1H, s), 8.15 (2H, d, J=8.3 Hz), 7.67 (2H, d, J=8.8 Hz), 7.51 (2H, d, J=8.3 Hz), 7.36 (2H, d, J=8.8 Hz), 6.35 (1H, s), 5.79 (1H, s), 4.22 (1H, m), 3.86(3H, s), 3.61 (2H, s), 2.50 (8H, br s), 2.30 (3H, s), 1.76 (4H, m), 0.99 (6H, t, J=7.3H) Mass spectrum (FAB-MS) m/z (%): 619 (MH$^+$), 546

(2) 7-(1-ethylpropoxy)-5-hydroxy-2-{4-[4-(4-methylpiperazinomethyl)benzoyloxy]phenylthio}-6-methoxychromone dihydrochloride Melting points: 195°–200° C. (Resolve) Infrared absorption spectrum (IR, vmax cm$^{-1}$, KBr): 3424, 2968, 2936, 1742, 1656, 1602 Proton nuclear magnetic resonance spectrum (δppm in CD$_3$OD): 8.29 (2H, d, J=8.3 Hz), 7.86 (2H, d, J=8.3 Hz), 7.79 (2H, d, J=8.8 Hz), 7.47 (2H, d, J=8.8 Hz), 6.57 (1H, s), 5.79 (1H, s), 4.40 (3H, m), 3.82 (3H, s), 3.60 (8H, m), 2.99 (3H, s), 1.76 (4H, m), 0.99 (6H, t, J=7.6 Hz) HRMS: C$_{34}$H$_{39}$O$_7$Cl$_2$N$_2$S Calculated: 619.24780 Found; 619.24795

EXAMPLE 41

2.02 g of Intermediate (1) obtained in the example, 2.08 g of potassium carbonate, 30 ml acetone, and 30 ml water were placed in a reaction vessel, followed by addition of 0.93 ml benzenethiol. The mixture was stirred for 4 hours at room temperature. Subsequently, water was added to the solution thus reacted. The product was extracted twice with dichloromethane. The organic layer was washed with saturated salt water and dried over sodium sulfate anhydride. The solvent was distilled out under reduced pressure. The crude product was purified by flash column chromatography (chloroform:acetone=30:1) and was then recrystallized from 60 ml methanol, whereby 1.79 g of 5,7-dimethoxy-2-phenylthiochromone with the following physicochemical properties was obtained.

Melting points: 185°–186° C. Infrared absorption spectrum (IR, vmax cm$^{-1}$, KBr): 1640, 1624, 1592, 1462, 1326, 1218, 1166, 1128 Proton nuclear magnetic resonance spectrum (δppm in CDCl$_3$): 7.60 (2H, m), 7.47 (3H, m), 6.38 (1H, d, J=2.2 Hz), 6.34 (1H, d, J=2.2 Hz), 5.82 (1H, s), 3.91 (3H, s), 3.86 (3H, s) Mass spectrum (EI-MS) m/z (%): 314, 285, 268 Elemental analysis: C$_{17}$H$_{14}$O$_4$S Calculated; C:64.95, H:4.49 Found; C:64.89, H:4.55

EXAMPLE 42

2.03 g of Intermediate (1) obtained in the example, 2.09 g of potassium carbonate, 30 ml acetone, and 30 ml water were placed in a reaction vessel, followed by addition of 1.03 ml 2-chlorobenzenethiol. The mixture was stirred for 3 hours at room temperature. Subsequently, water was added to the solution thus reacted. The product was extracted twice with dichloromethane. The organic layer was washed with saturated salt water and dried over sodium sulfate anhydride. The solvent was distilled out under reduced pressure. The crude product was recrystallized from ethanol-water (100 ml–50 ml), whereby 2.32 g of 5,7-dimethoxy-2-(2-chlorophenylthio)chromone with the following physicochemical properties was obtained.

Melting points: 170°–171° C. Infrared absorption spectrum (IR, vmax cm$^{-1}$, KBr): 1648, 1624, 1596, 1456, 1422, 1320, 1220, 1162, 1116, 760 Proton nuclear magnetic resonance spectrum (δppm in CDCl$_3$): 7.65 (1H, dd, J=8.0, 1.0 Hz) 7.55 (1H, dd, J=8.0, 1.0 Hz), 7.42 (1H, td, J=8.0, 1.0 Hz), 7.32 (1H, td, J=8.0, 1.0 Hz), 6.37 (1H, d, J=2.2 Hz), 6.35 (1H; d, J=2.2 Hz), 5.86 (1H, s), 3.92 (3H, s), 3.85 (3H,s) Mass spectrum (EI-MS) m/z (%): 350, 348, 321, 319, 304, 302 Elemental analysis: C$_{17}$H$_{13}$ClO$_4$S Calculated; C:58.54, H:3.76 Found; C:58.57, H:3.65

EXAMPLE 43

2.02 g of Intermediate (1) obtained in the example, 2.08 g of potassium carbonate, 30 ml acetone, and 30 ml water were placed in a reaction vessel, followed by addition of 1.05 ml 3-chlorobenzenethiol. The mixture was stirred for 3 hours at room temperature. Subsequently, water was added to the solution thus reacted. The product was extracted twice with dichloromethane. The organic layer was washed with saturated salt water and dried over sodium sulfate anhydride. The solvent was distilled out under reduced pressure. The crude product was recrystallized from 60 ml methanol, whereby 1.73 g of 5,7-dimethoxy-2-(3-chlorophenylthio) chromone with the following physicochemical properties was obtained.

Melting points: 150°–151° C. Infrared absorption spectrum (IR, vmax cm$^{-1}$, KBr): 1634, 1590, 1488, 1462, 1424, 1320, 1222, 1202, 1164, 1128, 796 Proton nuclear magnetic resonance spectrum (δppm in CDCl$_3$): 7.60 (1H, t, J=2.0 Hz), 7.54–7.35 (3H, m), 6.36 (1H, d, J=2.2 Hz), 6.35 (1H, d, J=2.2 Hz), 5.92 (1H, s), 3.92 (3H, s), 3.86(3H, s) Mass spectrum (EI-MS) m/z (%): 350, 348, 321, 319, 304, 302 Elemental analysis: C$_{17}$H$_{13}$ClO$_4$S Calculated; C:58.54, H:3.76 Found; C:58.59, H:3.70

EXAMPLE 44

2.03 g of Intermediate (1) obtained in the example, 2.08 g of potassium carbonate, 30 ml acetone, and 30 ml water were placed in a reaction vessel, followed by addition of 1.31 g of 4-chlorobenzenethiol. The mixture was stirred for 3 hours at room temperature. Subsequently, water was added to the solution thus reacted. The product was extracted twice with dichloromethane. The organic layer was washed with saturated salt water and dried over sodium sulfate anhydride. The solvent was distilled out under reduced pressure. The crude product was recrystallized from 300 ml methanol, whereby 2.52 g of 5,7-dimethoxy-2-(4-chlorophenylthio) chromone with the following physicochemical properties was obtained.

Melting points: 206°–208° C. Infrared absorption spectrum (IR, vmax cm$^{-1}$, KBr): 1640, 1624, 1592, 1328, 1216, 1166, 1130, 1092 Proton nuclear magnetic resonance spectrum (δppm in CDCl$_3$): 7.52 (2H, d, J=8.9 Hz), 7.43 (2H, d, J=8.9 Hz), 6.36 (1H, d, J=2.2 Hz), 6.34 (1H, d, J=2.2 Hz), 5.85 (1H, s), 3.92 (3H, s), 3.86 (3H, s) Mass spectrum (EI-MS) m/z (%): 350, 348, 321, 319, 304, 302 Elemental analysis: C$_{17}$H$_{13}$ClO$_4$S Calculated; C:58.54, H:3.76 Found; C:58.53, H:3.61

EXAMPLE 45

2.03 g of Intermediate (1) obtained in the example, 2.09 g of potassium carbonate, 30 ml acetone, and 30 ml water were placed in a reaction vessel, followed by addition of 1.41 g of 4-nitrobenzenethiol. The mixture was stirred for 3 hours at room temperature. Subsequently, water was added to the solution thus reacted. The product was extracted twice with dichloromethane. The organic layer was washed with saturated salt water and dried over sodium sulfate anhydride. The solvent was distilled out under reduced pressure. The crude product was recrystallized from 300 ml methanol, whereby 2.17 g of 5,7-dimethoxy-2-(4-nitrophenylthio) chromone with the following physicochemical properties was obtained.

Melting points: 182°–184° C. Infrared absorption spectrum (IR, vmax cm$^{-1}$, KBr): 1632, 1596, 1512, 1348, 1320, 1162 1124 Proton nuclear magnetic resonance spectrum (δppm in CDCl$_3$): 8.25 (2H, d, J=9.0 Hz), 7.65 (2H, d, J=9.0 Hz), 6.37 (1H, d, J=2.3 Hz), 6.32 (1H, d, J=2.3 Hz), 6.26 (1H, s), 3.94(3H, s), 3.85 (3H, s) Mass spectrum (EI-MS) m/z (%): 359, 330, 313 Elemental analysis: C$_{17}$H$_{13}$NO$_6$S Calculated; C:56.82, H:3.65, N:3.90 Found; C:56.74, H:3.61, N:4.14

EXAMPLE 46

2.05 g of Intermediate (1) obtained in the example, 2.11 g of potassium carbonate, 30 ml acetone, and 30 ml water were placed in a reaction vessel, followed by addition of 1.11 ml of 2-methoxybenzenethiol. The mixture was stirred for 3 hours at room temperature. Subsequently, water was added to the solution thus reacted. The product was extracted twice with dichloromethane. The organic layer was washed with saturated salt water and dried over sodium sulfate anhydride. The solvent was distilled out under reduced pressure. The crude product was purified by flash column chromatography (chloroform:acetone=30:1) and was then recrystallized from 60 ml methanol, whereby 1.38 g of 5,7-dimethoxy-2-(2-methoxyphenylthio)chromone with the following physicochemical properties was obtained.

Melting points: 185°–186° C. Infrared absorption spectrum (IR, vmax cm$^{-1}$, KBr): 1642, 1626, 1594, 1476, 1316, 1158, 1120 Proton nuclear magnetic resonance spectrum (δppm in CDCl$_3$): 7.55 (1H, m), 7.46 (1H, dd, J=8.1, 2.0 Hz), 7.01 (2H, m), 6.39 (1H, d, J=2.2 Hz), 6.33 (1H, d, J=2.2 Hz), 5.74 (1H, s), 3.91 (3H, s), 3.86 (3H, s), 3.85 (3H, s) Mass spectrum (EI-MS) m/z (%): 344, 315, 298 Elemental analysis: C$_{18}$H$_{16}$O$_5$S Calculated; C:62.78, H:4.68 Found; C:62.81, H:4.95

EXAMPLE 47

2.02 g of Intermediate (1) obtained in the example, 2.07 g of potassium carbonate, 30 ml acetone, and 30 ml water were placed in a reaction vessel, followed by addition of 1.12 ml of 3-methoxybenzenethiol. The mixture was stirred for 3 hours at room temperature. Subsequently, water was added to the solution thus reacted. The product was extracted twice with dichloromethane. The organic layer was washed with saturated salt water and dried over sodium sulfate anhydride. The solvent was distilled out under reduced pressure. The crude product was purified by flash column chromatography (chloroform:acetone=30: 1) and then recrystallized from 25 ml methanol, whereby 1.89 g of 5,7-dimethoxy-2-(3-methoxyphenylthio)chromone with the following physicochemical properties was obtained.

Melting points: 147°–148° C. Infrared absorption spectrum (IR, v max cm$^{-1}$, KBr): 1642, 1626, 1588, 1314, 1122 Proton nuclear magnetic resonance spectrum (δppm in CDCl$_3$): 7.36 (1H, dd, J=8.3, 7.8 Hz), 7.21 (1H, ddd, J=7.8, 2.1, 1.0 Hz), 7.11 (1H, dd, J=2.4, 2.1 Hz), 7.00 (1H, ddd, J=8.3, 2.4, 1.0, Hz), 6.39 (1H, d, J=2.2 Hz), 6.34 (1H, d, J=2.2 Hz), 5.86 (1H, s), 3.91 (3H, s), 3.86 (3H, s), 3.82 (3H, s) Mass spectrum (EI-MS) m/z (%): 344, 315, 298 Elemental analysis: C$_{18}$H$_{16}$O$_5$S Calculated; C:62.78, H:4.68 Found; C:62.78, H:4.67

EXAMPLE 48

2.02 g of Intermediate (1) obtained in the example, 2.07 g of potassium carbonate, 30 ml acetone, and 30 ml water were placed in a reaction vessel, followed by addition of 1.11 ml of 4methoxybenzenethiol. The mixture was stirred for 3 hours at room temperature. Subsequently, water was added to the solution thus reacted. The product was extracted twice with dichloromethane. The organic layer was washed with saturated salt water and dried over sodium sulfate anhydride. The solvent was distilled out under reduced pressure. The crude product was purified by flash column chromatography (chloroform:acetone=30:1) and then recrystallized from 220 ml methanol, whereby 1.96 g of 5,7-dimethoxy-2-(4-methoxyphenylthio)chromone with the following physicochemical properties was obtained.

Melting points: 207°–209° C. Infrared absorption spectrum (IR, vmax cm$^{-1}$, KBr): 1640, 1624, 1592, 1324, 1166, 1130 Proton nuclear magnetic resonance spectrum (δppm in CDCl$_3$): 7.52 (2H, d, J=9.0 Hz), 6.97 (2H, d, J=9.0 Hz), 6.39 (1H, d, J=2.2 Hz), 6.33 (1H, d, J=2.2 Hz), 5.67 (1H, s), 3.91 (3H, s), 3.86 (6H, s) Mass spectrum (EI-MS) m/z (%): 344, 315; 298 Elemental analysis: $C_{18}H_{16}O_5S$ Calculated; C:62.78, H:4.68 Found; C:62.75, H:4.62

EXAMPLE 49

2.04 g of Intermediate (1) obtained in the example, 2.10 g of potassium carbonate, 30 ml acetone, and 30 ml water were placed in a reaction vessel, followed by addition of 0.98 ml of 2-aminobenzenethiol. The mixture was stirred for 3 hours at room temperature. Subsequently, water was added to the solution thus reacted. The product was extracted twice with dichloromethane. The organic layer was washed with saturated salt water and dried over sodium sulfate anhydride. The solvent was distilled out under reduced pressure. The product was recrystallized from 240 ml methanol, whereby 1.23 g of 5,7-dimethoxy-2-(2-aminophenylthio)chromone with the following physicochemical properties was obtained.

Melting points: 208° C. (Resolve) Infrared absorption spectrum (IR, vmax cm$^{-1}$, KBr): 3444, 3340, 1640, 1622, 1588, 1484, 1462, 1322, 1218, 1164, 1126 Proton nuclear magnetic resonance spectrum (δppm in CDCl$_3$): 7.43 (1H, dd, J=7.7, 1.0 Hz), 7.26 (1H, td, J=7.7, 1.0 Hz), 6.82–6.73 (2H, m), 6.40 (1H, d, J=2.2 Hz), 6.33 (1H, d, J=2.2 Hz), 5.73 (1H, s), 4.35 (2H, br s), 3.90 (3H, s), 3.87 (3H, s) Mass spectrum (EI-MS) m/z (%): 329, 205, 181 Elemental analysis: $C_{17}H_{15}NO_4S$ Calculated; C:61.99, H:4.59, N:4.25 Found; C:61.99, H:4.55, N:4.40

EXAMPLE 50

2.03 g of Intermediate (1) obtained in the example, 2.09 g of potassium carbonate, 30 ml acetone, and 30 ml water were placed in a reaction vessel, followed by addition of 0.96 ml of 3-aminobenzenethiol. The mixture was stirred for 3 hours at room temperature. Subsequently, water was added to the solution thus reacted. The product was extracted twice with dichloromethane. The organic layer was washed with saturated salt water and dried over sodium sulfate anhydride. The solvent was distilled out under reduced pressure. The product was recrystallized from 150 ml methanol, whereby 564 mg of 5,7-dimethoxy-2-(3-aminophenylthio)chromone with the following physicochemical properties was obtained.

Melting points: 212°–213° C. Infrared absorption spectrum (IR, vmax cm$^{-1}$, KBr): 3436, 3336, 1626, 1588, 1322, 1126 Proton nuclear magnetic resonance spectrum (δppm in CDCl$_3$): 7.21 (1H, t, J=7.8 Hz), 6.95 (1H, br d, J=7.8 Hz), 6.88 (1H, t, J=1.0 Hz), 6.75 (1H, dd, J=7.8, 1.0 Hz), 6.39 (1H, d, J=2.2 Hz), 6.33 (1H, d, J=2.2 Hz), 5.88 (1H, s), 3.91 (3H, s), 3.86 (3H, s), 3.80 (2H, br s) Mass spectrum (EI-MS) m/z (%): 329, 300, 283, 149 Elemental analysis: $C_{17}H_{15}NO_4S$ Calculated; C:61.99, H:4.59, N:4.25 Found; C:61.72, H:4.52, N:4.38

EXAMPLE 51

2.04 g of Intermediate (1) obtained in the example, 2.11 g of potassium carbonate, 30 ml acetone, and 30 ml water were placed in a reaction vessel, followed by addition of 1.14 g of 4-aminobenzenethiol. The mixture was stirred for 3 hours at room temperature. Subsequently, water was added to the solution thus reacted. The product was extracted twice with dichloromethane. The organic layer was washed with saturated salt water and dried over sodium sulfate anhydride. The solvent was distilled out under reduced pressure. The product was recrystallized from 100 ml methanol, whereby 324 mg of 5,7-dimethoxy-2-(4aminophenylthio)chromone with the following physicochemical properties was obtained.

Melting points: 258°–260° C. Infrared absorption spectrum (IR, vmax cm$^{-1}$, KBr): 3376, 3228, 1632, 1582, 1498, 1326, 1126, 820 Proton nuclear magnetic resonance spectrum (δppm in CDCl$_3$): 7.35 (2H, d, J=8.8 Hz), 6.70 (2H, d, J=8.8 Hz), 6.40 (1H, d, J=2.2 Hz), 6.33 (1H, d, J=2.2 Hz), 5.69 (1H, s), 3.97 (2H, br s), 3.90 (3H, s), 3.86 (3H, s) Mass spectrum (EI-MS) m/z (%): 329, 300, 283, 149 Elemental analysis: $C_{17}H_{15}NO_4S$ Calculated; C:61.99, H:4.59, N:4.25 Found; C:61.93, H:4.66, N:4.37

EXAMPLE 52

2.01 g of Intermediate (1) obtained in the example, 2.07 g of potassium carbonate, 30 ml acetone, and 30 ml water were placed in a reaction vessel, followed by addition of 1.06 ml of 2-methylbenzenethiol. The mixture was stirred for 20 hours at room temperature. Subsequently, water was added to the solution thus reacted. The product was extracted twice with dichloromethane. The organic layer was washed with saturated salt water and dried over sodium sulfate anhydride. The solvent was distilled out under reduced pressure. The crude product was purified by flash column chromatography (chloroform:acetone=30:1) and then recrystallized from 40 ml methanol, whereby 1.73 g of 5,7-dimethoxy-2-(2-methylphenylthio)chromone with the following physicochemical properties was obtained.

Melting points: 168°–169° C. Infrared absorption spectrum (IR, vmax cm$^{-1}$, KBr): 1644, 1628, 1594, 1472, 1316, 1214, 1200, 1158, 1122 Proton nuclear magnetic resonance spectrum (δppm in CDCl$_3$): 7.59 (1H, br d, J=7.8 Hz), 7.50–7.22 (3H, m), 6.39 (1H, d, J=2.2 Hz), 6.34 (1H, d, J=2.2 Hz), 5.62 (1H, s), 3.91 (3H, s), 3.86 (3H, s), 2.45 (3H, s) Mass spectrum (EI-MS) m/z (%): 328, 299, 282, 151 Elemental analysis: $C_{10}H_{10}O_4S$ Calculated; C:65.84, H:4.91 Found; C:65.79, H:4.66

EXAMPLE 53

2.04 g of Intermediate (1) Obtained in the example, 2.10 g of potassium carbonate, 30 ml acetone, and 30 ml water were placed in a reaction vessel, followed by addition of 1.08 ml of 3-methylbenzenethiol. The mixture was stirred for 20 hours at room temperature. Subsequently, water was added to the solution thus reacted. The product was extracted twice with dichloromethane. The organic layer was washed with saturated salt water and dried over sodium sulfate anhydride. The solvent was distilled out under reduced pressure. The crude product was purified by flash column chromatography (chloroform:acetone=30:1) and then recrystallized from 30 ml methanol, whereby 1.50 g of 5,7-dimethoxy-2-(3-methylphenylthio)chromone with the following physicochemical properties was obtained.

Melting points: 146°–147° C. Infrared absorption spectrum (IR, vmax cm$^{-1}$, KBr): 1644, 1624, 1592, 1324, 1164, 1128 Proton nuclear magnetic resonance spectrum (δppm in CDCl$_3$): 7.41–7.26 (4H, m), 6.39 (1H, d, J=2.2 Hz), 6.34 (1H, d, J=2.2 Hz), 5.79 (1H, s), 3.91 (3H, s), 3.86 (3H, s), 2.38 (3H, s) Mass spectrum (EI-MS) m/z (%): 328, 299, 282, 148 Elemental analysis: $C_{18}H_{16}O_4S$ Calculated; C:65.84, H:4.91 Found; C:65.80, H:4.95

EXAMPLE 54

2.03 g of Intermediate (1) obtained in the example, 2.09 g of potassium carbonate, 30 ml acetone, and 30 ml water were placed in a reaction vessel, followed by addition of 1.13 g of 4-methylbenzenethiol. The mixture was stirred for 20 hours at room temperature. Subsequently, water was added to the solution thus reacted. The product was extracted twice with dichloromethane. The organic layer was washed with saturated salt water and dried over sodium sulfate anhydride. The solvent was distilled out under reduced pressure. The crude product was purified by flash column chromatography (chloroform:acetone=30:1) and then recrystallized from 160 ml methanol, whereby 1.89 g of 5,7-dimethoxy-2-(4-methylphenylthio)chromone with the following physicochemical properties was obtained.

Melting points: 209°–210° C. Infrared absorption spectrum (IR, vmax $cm^{-1}$, KBr): 1642, 1624, 1592, 1326, 1218, 1166, 1130 Proton nuclear magnetic resonance spectrum (δppm in $CDCl_3$): 7.48 (2H, d, J=8.1 Hz), 7.25 (2H, d, J=8.1 Hz), 6.39 (1H, d, J=2.2 Hz), 6.33 (1H, d, J=2.2 Hz), 5.73 (1H, s),3.91 (3H, s), 3.86 (3H, s),2.41 (3H, s) Mass spectrum (EI-MS) m/z (%): 328, 299, 282, 148 Elemental analysis: $C_{18}H_{16}O_4S$ Calculated; C:65.84, H:4.91 Found; C:65.85, H:4.85

EXAMPLE 55

2.031 g of Intermediate (1) obtained in the example, 2.089 g of potassium carbonate, 30 ml acetone, and 30 ml water were placed in a reaction vessel, followed by addition of 2.164 g of 4-hydroxy-3,5-di-t-butylbenzenethiol. The mixture was stirred for 2 hours at room temperature. Subsequently, the solution thus reacted was made acidic by addition of 1N hydrochloric acid. The product was extracted twice with dichloromethane. The organic layer was washed with saturated salt water and dried over sodium sulfate anhydride. The solvent was distilled out under reduced pressure. The resulting crystals containing impurities were purified by flash column chromatography (chloroform:acetone=40:1) and then recrystallized from ethanol, whereby 1.813 g of 2-(3,5-di-t-butyl-4-hydroxyphenylthio)-5,7-dimethoxychromone with the following physicochemical properties was obtained.

Melting points: 246°–247° C. Infrared absorption spectrum (IR, vmax $cm^{-1}$, KBr): 3560, 2960, 1626, 1588, 1468, 1422, 1318, 1200, 1160, 1120, 1096 Proton nuclear magnetic resonance spectrum (δppm in $CDCl_3$): 7.39 (2H, s), 6.42 (1H, d, J=2.2 Hz), 6.33 (1H, d, J=2.2 Hz), 5.72 (1H, s), 5.54 (1H, s), 3.91 (3H, s), 3.87 (3H, s), 1.44 (18H, s) Mass spectrum (EI-MS) m/z (%): 442, 427, 409 Elemental analysis: $C_{25}H_{30}O_5S$ Calculated; C:67.85, H:6.83 Found; C:67.57, H:7.03

EXAMPLE 56

2.548 g of Intermediate (1) obtained in the example, 2.622 g of potassium carbonate, 40 ml acetone, and 40 ml water were placed in a reaction vessel, followed by addition of 1.437 g of 2-hydroxybenzenethiol. The mixture was stirred for 20 hours at room temperature. Subsequently, the solution thus reacted was made acidic by addition of 1N hydrochloric acid. Solids thus precipitated were collected by filtration, then washed with water, and dried under reduced pressure. The resulting crystals containing impurities were recrystallized from ethanol, whereby 403 mg of 2-(2-hydroxyphenylthio)-5,7-dimethoxychromone with the following physicochemical properties was obtained.

Melting points: 206°–207° C. Infrared absorption spectrum (IR, vmax $cm^{-1}$, KBr): 3132, 1616, 1580, 1322, 1310, 1160 1124 Proton nuclear magnetic resonance spectrum (δppm in DMSO-$d_6$): 10.42 (1H, br s), 7.49 (1H, dd, J=7.8, 1.4 Hz), 7.40 (1H, ddd, J=8.3, 7.8, 1.4 Hz), 7.04 (1H, dd, J=8.3, 1.0 Hz), 6.93 (1H, td, J=7.8, 1.0 Hz), 6.59, (1H, d, J=2.2 Hz), 6.48 (1H, d, J=2.2 Hz), 5.43 (1H, s), 3.86 (3H, s), 3.80 (3H, s) Mass spectrum (EI-MS) m/z (%): 330, 180, 150, 137 Elemental analysis: $C_{17}H_{14}O_5S$ Calculated; C:61.81, H:4.27 Found; C:61.65, H:4.09

EXAMPLE 57

2.636 g of Intermediate (1) obtained in the example, 2.713 g of potassium carbonate, 40 ml acetone, and 40 ml water were placed in a reaction vessel, followed by addition of 1.487 g of 3-hydroxybenzenethiol. The mixture was stirred for 3 hours at room temperature. Subsequently, the solution thus reacted was made acidic by addition of 1N hydrochloric acid. Solids thus precipitated were collected by filtration, then washed with water, and dried under reduced pressure. The resulting crystals containing impurities were recrystallized from ethanol, whereby 1.197 g of 2-(3-hydroxyphenylthio)-5,7-dimethoxychromone with the following physicochemical properties was obtained.

Melting points: 255°–256° C. Infrared absorption spectrum (IR, vmax $cm^{-1}$, KBr): 1628, 1604, 1572, 1463, 1332, 1164, 1130 Proton nuclear magnetic resonance spectrum (δppm in DMSO-$d_6$): 9.74 (1H, br s), 7.34 (1H, t, J=7.8 Hz), 7.04 (1H, dt, J=7.8, 1.0 Hz), 7.00 (1H, t, J=1.4 Hz), 6.93 (1H, ddd, J=7.8, 1.4, 1.0 Hz), 6.58 (1H, d, J=2.2 Hz), 6.49 (1H, d, J=2.2 Hz), 5.67 (1H, s), 3.86 (3H, s), 3.81 (3H, s) Mass spectrum (EI-MS) m/z (%): 330, 301, 284, 151 Elemental analysis: $C_{17}H_{14}O_5S$ Calculated; C:61.81, H:4.27 Found; C:61.67, H:4.17

EXAMPLE 58

2.052 g of Intermediate (1) obtained in the example, 2.536 g of potassium carbonate, 30 ml acetone, and 30 ml water were placed in a reaction vessel, followed by addition of 1.019 g of 2-mercaptopyridine. The mixture was stirred for 3 hours at room temperature. Subsequently, water was added to the solution thus reacted. The product was extracted twice with dichloromethane. The organic layer was washed with saturated salt water and dried over sodium sulfate anhydride. The solvent was distilled out under reduced pressure. The resulting crystals containing impurities were purified by flash column chromatography (chloroform:acetone=20:1) and then recrystallized from 80 ml methanol, whereby 1.561 g of 5,7-dimethoxy-2-(2-pyridylthio)chromone with the following physicochemical properties was obtained.

Melting points: 164°–165° C. Infrared absorption spectrum (IR, vmax $cm^{-1}$, KBr): 1642, 1622, 1594, 1574, 1458, 1422, 1326, 1224, 1200, 1158, 1116, 1094 Proton nuclear magnetic resonance spectrum (δppm in $CDCl_3$): 8.57 (1H, ddd, J=4.9, 2.0, 1.0 Hz), 7.68 (1H, td, J=7.8, 2.0 Hz), 7.43 (1H, dt, J=7.8, 1.0 Hz), 7.24 (1H, ddd, J=7.8, 4.9, 1.0 Hz), 6.38 (1H, s), 6.37 (1H, d, J=2.4 Hz), 6.35 (1H, d, J=2.4 Hz), 3.93 (3H, s), 3.85 (3H, s), Mass spectrum (EI-MS) m/z (%): 315, 286, 272, 205 Elemental analysis: $C_{16}H_{13}NO_4S$ Calculated; C:60.94, H:4.16, N:4.44 Found; C:60.84, H:4.23, N:4.62

EXAMPLE 59

2.048 g of Intermediate (1) obtained in the example, 2.108 g of potassium carbonate, 30 ml acetone, and 30 ml water were placed in a reaction vessel, followed by addition of 1.018 g of 4-mercaptopyridine. The mixture was stirred for 2 hours at room temperature. Subsequently, water was added to the solution thus reacted. The product was extracted twice with dichloromethane. The organic layer was washed with saturated salt water and dried over sodium sulfate anhydride. The solvent was distilled out under reduced pressure. The resulting crystals containing impurities were purified by flash column chromatography (chloroform:acetone=20:1) and then recrystallized from 50 ml methanol, whereby 916 mg of 5,7-dimethoxy-2-(4-pyridylthio)chromone with the following physicochemical properties was obtained.

Melting points: 165°–166° C. Infrared absorption spectrum (IR, νmax cm$^{-1}$, KBr): 1656, 1622, 1600, 1572, 1460, 1330, 1318, 1158, 1120 Proton nuclear magnetic resonance spectrum (δppm in CDCl$_3$): 8.59 (2H, d, J=6.0 Hz), 7.33 (2H, d, J=6.0 Hz), 6.38 (1H, s), 6.37 (1H, d, J=2.2 Hz), 6.35 (1H, d, J=2.2 Hz), 3.94 (3H, s), 3.85 (3H, s) Mass spectrum (EI-MS) m/z (%): 315, 286, 269, 237, 150 Elemental analysis: $C_{16}H_{13}NO_4S$ Calculated; C:60.94, H:4.16, N:4.44 Found; C:60.88, H:4.09, N:4.67

EXAMPLE 60

2.077 g of Intermediate (1) obtained in the example, 2.139 g of potassium carbonate, 30 ml acetone, and 30 ml water were placed in a reaction vessel, followed by addition of 1.396 g of 2mercaptobenzimidazole. The mixture was stirred for 3 hours at room temperature. Subsequently, water was added to the solution thus reacted. The resulting crystals containing impurities were collected by filtration, then washed with water, and dried under reduced pressure. The product was recrystallized from 100 ml methanol, whereby 1.187 g of 2-(2-benzimidazolylthio)-5,7-dimethoxychromone with the following physicochemical properties was obtained.

Melting points: 233°–235° C. Infrared absorption spectrum (IR, νmax cm$^{-1}$, KBr): 3212, 1630, 1592, 1420, 1322, 1200, 1162, 1124 Proton nuclear magnetic resonance spectrum (δppm in CDCl$_3$): 7.59 (2H, dd, J=6.0, 3.2 Hz), 7.26 (2H, dd, J=6.0, 3.2 Hz), 6.58 (1H, dd, J=2.4 Hz), 6.52 (1H, d, J=2.4 Hz), 6.21 (1H, s), 3.83 (3H, s), 3.82 (3H, s) Mass spectrum (EI-MS) m/z (%): 354, 325, 321, 205 Elemental analysis: $C_{18}H_{14}N_2O_4S$ Calculated; C:61.01, H:3.98, N:7.90 Found; C:60.72, H:3.92, N:8.10

EXAMPLE 61

2.050 g of Intermediate (1) obtained in the example, 2.108 g of potassium carbonate, 30 ml acetone, and 30 ml water were placed in a reaction vessel, followed by addition of 1.535 g of 2mercaptobenzthiazole. The mixture was stirred for 16 hours at room temperature. Subsequently, water was added to the solution thus reacted. The resulting crystals containing impurities were collected by filtration, then washed with water, and dried under reduced pressure. The product was recrystallized from 150 ml methanol, whereby 1.097 g of 2-(2-benzthiazolylthio)-5,7-dimethoxychromone with the following physicochemical properties was obtained.

Melting points: 172°–173° C. Infrared absorption spectrum (IR, νmax cm$^{-1}$, KBr): 1646, 1624, 1592, 1314, 1110 Proton nuclear magnetic resonance spectrum (δppm in CDCl$_3$): 8.04 (1H, ddd, J=7.8, 1.3, 0.5 Hz), 7.84 (1H, ddd, J=7.8, 1.3, 0.5 Hz), 7.52 (1H, td, J=7.8, 1.3 Hz), 7.43 (1H, td, J=7.8, 1.3 Hz), 6.55 (1H, s), 6.42 (1H, d, 2.2 Hz), 6.38 (1H, d, 2.2 Hz), 3.94 (3H, s), 3.85 (3H, s) Mass spectrum (EI-MS) m/z (%): 371, 338, 205 Elemental analysis: $C_{18}H_{13}NO_4S_2$ Calculated; C:58.21, H:3.53, N:3.77 Found; C:58.14, H:3.51, N:3.81

EXAMPLE 62

2.024 g of Intermediate (1) obtained in the example, 2.083 g of potassium carbonate, 30 ml acetone, and 30 ml water were placed in a reaction vessel, followed by addition of 1.080 g of 2-mercaptothiazoline. The mixture was stirred for 3 hours at room temperature. Subsequently, water was added to the solution thus reacted. The product was extracted twice with chloroform. The organic layer was washed with saturated salt water and dried over sodium sulfate anhydride. The solvent was distilled out under reduced pressure. The resulting crystals containing impurities were subjected to recrystallization from 400 ml methanol, whereby 896 mg of 5,7-dimethoxy-2-(2-thiazolynylthio)chromone with the following physicochemical properties was obtained.

Melting points: 242°–244° C. Infrared absorption spectrum (IR, νmax cm$^{-1}$, KBr): 1664, 1642, 1608, 1392, 1342, 1264, 1216, 1204, 1162, 1114, 1062 Proton nuclear magnetic resonance spectrum (δppm in CDCl$_3$): 6.61 (1H, s), 6.42 (1H, d, J=2.2 Hz), 6.38 (1H, d, J=2.2 Hz), 4.55 (2H, t, J=7.4 Hz), 3.94 (3H, s), 3.88 (3H, s), 3.49 (2H, t, J=7.4 Hz) Mass spectrum (EI-MS) m/z (%): 323, 294, 204 Elemental analysis: $C_{14}H_{13}NO_4S_2$ Calculated; C:52.00, H:4.05, N:4.33 Found; C:51.96, H:4.10, N:4.34

EXAMPLE 63

2.018 g of Intermediate (1) obtained in the example, 2.078 g of potassium carbonate, 30 ml acetone, and 30 ml water were placed in a reaction vessel, followed by addition of 1.201 g of 2-amino-5-mercapto-1,3,4-thiadiazole. The mixture was stirred for 15 hours at room temperature. Subsequently, water was added to the solution thus reacted. The resulting crystals containing impurities were collected by filtration, then washed with water, and dried under reduced pressure. The product was recrystallized from methanol-2-methoxyethanol, whereby 1.063 g of 2-(2-amino-5-thiadiazolylthio)-5,7-dimethoxychromone with the following physicochemical properties was obtained.

Melting points: 239°–241° C. Infrared absorption spectrum (IR, νmax cm$^{-1}$, KBr): 3292, 3136, 1644, 1622, 1510, 1494, 1326, 1308, 1160, 1120 Proton nuclear magnetic resonance spectrum (δppm in DMSO-d$_6$): 7.82 (2H, br s), 6.59 (1H, d, J=2.2 Hz), 6.53 (1H, d, J=2.2 Hz), 6.06 (1H, s), 3.87 (3H, s), 3.82 (3H, s) Mass spectrum (EI-MS) m/z (%): 337, 304, 236, 181 Elemental analysis: $C_{13}H_{11}N_3O_4S_2$ Calculated; C:46.28, H:3.29, N: 12.46 Found; C:46.45, H:3.28, N: 12.37

EXAMPLE 64

A mixture consisting of 205 mg of Intermediate (1) obtained in the example, 142 mg of 4-mercaptobenzoic acid, 315 mg of potassium carbonate, 7 ml of acetone, and 7 ml of water was stirred for 3 hours at room temperature. Subsequently, water was added to the solution thus reacted. The product was extracted twice with ethyl acetate. The aqueous layer was made weakly acidic by addition of dilute hydrochloric acid, and the solids thus formed were collected by filtration. 277 mg of the resulting crystals containing impurities were subjected to recrystallization from methanol-DMSO (8 ml-6 ml), whereby 210 mg of 4-(5,7- dimethoxychromonyl-2-thio)benzoic acid with the following physicochemical properties was obtained.

Melting points: 253—Resolve Infrared absorption spectrum (IR, vmax cm$^{-1}$, KBr): 1710, 1608, 1574, 1328, 1312, 1272, 1160, 1128 Proton nuclear magnetic resonance spectrum (δppm in DMSO-d$_6$): 8.02 (2H, d, J=8.3 Hz), 7.69 (2H, d, J=8.3 Hz), 6.57 (1H, d, J=2.4 Hz), 6.50 (1H, d, J=2.4 Hz), 6.01 (1H, s), 3.84 (3H, s), 3.82 (3H, s) Mass spectrum (EI-MS) m/z (%): 358, 329, 327, 312 Elemental analysis: C$_{18}$H$_{14}$O$_6$S Calculated; C:60.33, H:3.94 Found; C:60.09, H:3.94

EXAMPLE 65

A mixture consisting of 257 mg of Intermediate (1) obtained in the example, 322 mg of methyl 4-mercaptobenzoate, 397 mg of potassium carbonate, 4 ml of acetone, and 4 ml of water was stirred for 3 hours at room temperature. Subsequently, water was added to the solution thus reacted. The product was extracted twice with ethyl acetate. The organic layer was washed with saturated salt water and dried over sodium sulfate anhydride. The solvent was distilled out under reduced pressure. 419 mg of the resulting crystals containing impurities were subjected to recrystallization from 30 ml methanol, whereby 316 mg of methyl 4-(5,7-dimethoxychromonyl-2-thio)benzoate with the following physicochemical properties was obtained. Melting points: 186°–187° C. Infrared absorption spectrum (IR, vmax cm$^{-1}$, KBr): 1718, 1640, 1594, 1318, 1282, 1162, 1118, 1106 Proton nuclear magnetic resonance spectrum (δppm in DMSO-d$_6$): 8.08 (2H, d, J=8.3 Hz), 7.61 (2H, d, J=8.3 Hz), 6.35 (1H, d, J=2.2 Hz), 6.33 (1H, d, J=2.2 Hz), 6.06 (1H, s), 3.95 (3H, s), 3.92 (3H, s), 3.85 (3H, s) Mass spectrum (EI-MS) m/z (%): 372, 357, 343, 341, 326 Elemental analysis: C$_{19}$H$_{16}$O$_6$S Calculated; C:61.28, H:4.33 Found; C:61.13, H:4.40

EXAMPLE 66

A mixture consisting of 88 mg of Intermediate (1) obtained in the example, 91 mg of 4-mercaptobenzyl alcohol, 182 mg of potassium carbonate, 3 ml of DMSO was stirred for 3 hours at room temperature and then allowed to stand overnight. Subsequently, the solution thus reacted was made weakly acidic by addition of dilute hydrochloric acid. The product was extracted twice with ethyl acetate. The organic layer was washed with saturated salt water and dried over sodium sulfate anhydride. The solvent was distilled out under reduced pressure. 163 mg of the resulting crystals containing impurities were purified by flash column chromatography (chloroform:acetone=10:1–5:1) and was then subjected to recrystallization from 1.5 ml methanol, whereby 38 mg of 5,7-dimethoxy-2-(4-hydroxymethylphenylthio)chromone with the following physicochemical properties was obtained.

Melting points: 188°–189° C. Infrared absorption spectrum (IR, vmax cm$^{-1}$, KBr): 3408, 1632, 1582, 1462, 1324, 1218, 1164, 1128, 1062 Proton nuclear magnetic resonance spectrum (δppm in CDCl$_3$): 7.59 (2H, d, J=8.3 Hz), 7.46 (2H, d, J=8.3 Hz), 6.39 (1H, d, J=2.2 Hz), 6.34 (1H, d, J=2.2 Hz), 5.77 (1H, s), 4.78 (2H, d, J=5.9 Hz), 3.91 (3H, s), 3.86 (3H, s) Mass spectrum (EI-MS) m/z (%): 344, 342, 313, 298 Elemental analysis: C$_{18}$H$_{16}$O$_5$S Calculated; C:62.78, H:4.68 Found; C:62.56, H:4.77

EXAMPLE 67

A mixture consisting of 37 mg of Intermediate (1) obtained in the example, 32 mg of 3,4-methylenedioxybenzenethiol, 39 mg of potassium carbonate, 1.5 ml of acetone, and 1.5 ml of water was stirred for 1 hour at room temperature. Subsequently, water was added to the solution thus reacted. The product was extracted twice with ethyl acetate. The organic layer was washed with saturated salt water and dried over sodium sulfate anhydride. The solvent was distilled out under reduced pressure. 66 mg of the resulting crystals containing impurities were subjected to recrystallization from 20 ml methanol, whereby 42 mg of 5,7-dimethoxy-2-(3,4-methylenedioxyphenylthio)chromone with the following physicochemical properties was obtained.

Melting points: 232°–233° C. Infrared absorption spectrum (IR, vmax cm$^{-1}$, KBr): 1640, 1590, 1480, 1324, 1254, 1240, 1164, 1126, 1102, 822 Proton nuclear magnetic resonance spectrum (δppm in CDCl$_3$): 7.12 (1H, dd, J=8.1, 1.7 Hz), 7.03 (1H, d, J=1.7 Hz), 6.87 (1H, d, J=8.1 Hz), 6.40 (1H, d, J=2.3 Hz), 6.34 (1H, d, 2.3 Hz), 5.74 (1H, s), 3.91 (3H, s), 3.87 (3H, s) Mass spectrum (EI-MS) m/z (%): 358, 329, 312, 178 Elemental analysis: C$_{18}$H$_{14}$O$_6$S Calculated; C:60.33, H:3.94 Found; C:60.13, H:3.75

EXAMPLE 68

66 mg of 3,4-dihydroxybenzenethiol and 351 mg of borax were dissolved in 3 ml of water, and the mixture was stirred over 30 min. at room temperature, followed by addition of 83 mg of Intermediate (1) obtained in the example and 3 ml of acetonitrile. Then, the mixture was stirred over 20 hours at room temperature. To the solution thus reacted were added dilute hydrochloric acid and a small amount of ethyl acetate, and the resulting white crystals were collected by filtration. This product was washed with water and then dried under reduced pressure, whereby 59 mg of 2-(3,4-dihydroxyphenylthio)-5,7-dimethoxychromone with the following physicochemical properties was obtained.

Melting points: 262° C.—Resolve Infrared absorption spectrum (IR, vmax cm$^{-1}$, KBr): 3440, 1626, 1580, 1494, 1460, 1422, 1390, 1332, 1278, 1218, 1204, 1162, 1126, 828 Proton nuclear magnetic resonance spectrum (δppm in CDCl$_3$): 9.70 (1H, br s), 9.50 (1H, br s), 6.99 (1H, d, J=2.0 Hz), 6.97 (1H, dd, J=8.6, 2.0 Hz), 6.90 (1H, d, J=8.6 Hz), 6.61 (1H, d, J=2.2 Hz), 6.48 (1H, d, 2.2 Hz), 5.40 (1H, s), 3.86 (3H, s), 3.79(3H, s) Mass spectrum (EI-MS) m/z (%): 346, 153 HRMS: C$_{17}$H$_{14}$O$_6$S Calculated; 346.05102 Found; 346.05082

EXAMPLE 69

A mixture consisting of 8.37 g of floroacetophenone, 25.0 g of isopropyl iodide, 20.62 g of potassium carbonate, and 120 ml of acetone was stirred for 2 days under reflux at a bath temperature of 60° C. The solution thus reacted was neutralized with dilute hydrochloric acid. The product was extracted twice with ethyl acetate. The organic layer was washed with saturated salt water and dried over sodium sulfate anhydride. The solvent was distilled out under reduced pressure. 12.46 g of the resulting crystals containing impurities were purified by flash column chromatography (hexane:ethyl acetate=40:1), so that 9.46 g diisopropyl compound was obtained.

399 mg of t-butoxy potassium was suspended in 10 ml THF under cooling on ice. To this solution were added 3 ml of 225 mg of the diisopropyl compound in THF and 3 ml of 135 mg carbon disulfide in THF. The mixture was stirred overnight at room temperature. Methyl iodide was added to the solution thus reacted, followed by stirring for 1 hour. Then, water was added and the product was extracted twice with ethyl acetate. Subsequently, the organic layer was washed with saturated salt water and dried over sodium sulfate anhydride. The solvent was distilled out under reduced pressure. The resulting oil, 345 mg, was purified by flash column chromatography (chloroform:acetone=10:1), to give a sulfide.

A mixture consisting of 136 mg of the resulting sulfide, 271 mg oxone, 3 ml methanol, and 3 ml water was stirred for 2 hours at room temperature. Then, water was added to the mixture thus reacted. The product was extracted twice with chloroform. The organic layer was washed with saturated salt solution and dried over sodium sulfate anhydride. The solvent was distilled out under reduced pressure. 80 mg of the resulting crystals containing impurities were purified by flash column chromatography (chloroform:acetone=10:1), whereby 31 mg sulfoxide was obtained.

A mixture consisting of 29 mg of the sulfoxide, 23 mg of 4-hydroxybenzenethiol, 25 mg of potassium carbonate, and 3 ml acetone was stirred for 20 hours at room temperature. Then, water was added to the solution thus reacted. This solution was made weakly acidic by addition of dilute hydrochloric acid, and the resulting solids were collected ed by filtration. The product was washed with water and then dried. 29 mg of the resulting crystals containing impurities was subjected to recrystallization from 2 ml methanol, thug giving 17 mg of 5,7-diisopropoxy-2-(4-hydroxyphenylthio) chromone with the following physicochemical properties.

Melting points: 234°–236° C. Infrared absorption spectrum (IR, vmax $cm^{-1}$, KBr): 2980, 1612, 1578, 1498, 1452, 1426, 1380, 1322, 1286, 1112 Proton nuclear magnetic resonance spectrum (δppm in $CDCl_3$): 7.47 (2H, d, J=8.3 Hz), 6.92 (2H, d, J=8.3 Hz), 6.56 (1H, d, J=2.4 Hz), 6.41 (1H, d, J=2.4 Hz), 5.32 (1H, s), 4.76 (1H, h, J=6.1 Hz), 4.59 (1H, h, J=6.1 Hz), 1.29 (6H, d, J=6.1 Hz), 1.25 (3H, d, J=6.1 Hz) Mass spectrum (EI-MS) m/z (%): 386, 371, 344, 328, 302, 286, 150 HRMS: $C_{21}H_{22}O_5S$ Calculated; 386.11876 Found; 386.11596

EXAMPLE 70

4.3 g of Intermediate (1) obtained in the example, 5.3 g of p-hydroquinone, and 3.8 g of sodium hydroxide were placed in a reaction vessel, and the atmosphere in the vessel was replaced by nitrogen. 86 ml of water-free dimethyl sulfoxide was added. The mixture was stirred for 1.5 hours at room temperature. The solution thus reacted was poured into 1N glacial acetic acid (pH 1–2), followed by stirring for 10 min. Then, impurities precipitated were collected by filtration, to give yellowish white solids. The solids was subjected to recrystallization from methanol-chloroform-n-hexane, so that 3.91 g of 2-(4-hydroxyphenoxy)-5,7-dimethoxychromone with the following physicochemical properties were obtained in the form of colorless acicular crystals. Melting points: 247°–250° C. Infrared absorption spectrum (IR, vmax $cm^{-1}$, KBr): 3204, 1644, 1606, 1566, 1510, 1494, 1462, 1408, 1356, 1284, 1214, 1162, 1106, 1052, 1016, 962, 944, 830, 818, 744, 636, 496 Proton nuclear magnetic resonance spectrum (δppm in DMSO-$d_6$): 3.80 (3H, s), 3.87 (3H, s), 4.88 (1H, s), 6.52 (1H, d, J=2.4 Hz), 6.68 (1H; d, J=2.4 Hz), 6.86 (2H, d, J=8.8 Hz), 7.15 (2H, d, J=8.8 Hz), 9.71 (1H, s, $D_2O$ exchange) Mass spectrum (EI-MS) m/z (%): 314 (29, $M^+$), 285(8), 268(11), 151 (15), 78(76), 63(100) Elemental analysis: $C_{17}H_{14}O_6$ Calculated; C:64.96, H:4.49 Found; C:64.24, H:4.46

EXAMPLE 71

3.89 g of Intermediate (1) obtained in the example, 2.43 g of 4-hydroxybenzenethiol, and 1.40 g of sodium hydroxide were placed in a reaction vessel, and then the atmosphere in the vessel was replaced by nitrogen. 78 ml of water-free dimethyl sulfoxide was added. The mixture was stirred overnight at room temperature. The solution thus reacted was poured into 1N glacial acetic acid. Impurities precipitated were collected by filtration (and sufficiently washed with water), to give white solids. The solids was subjected to recrystallization from methanol-chloroform-n-hexane, whereby 3.18 g of 2-(4-hydroxyphenylthio)-5,7-dimethoxychromone with the following physicochemical properties was obtained as colorless fine acicular crystal. &p Melting points: 272°–275° C. Infrared absorption spectrum (IR, vmax $cm^{-1}$, KBr): 3208, 1626, 1578, 1496, 1458, 1330, 1272, 1204, 1164, 1124, 1106, 1060, 920, 834, 692, 670, 598, 528 Proton nuclear magnetic resonance spectrum (δppm in DMSO-$d_6$): 3.79 (3H, s), 3.86 (3H, s), 5.36 (1H, s), 6.49 (1H, d, J=2.4 Hz), 6.61 (1H, d, J=2.4 Hz), 6.93 (2H, d, J=8.8 Hz), 7.50 (2H, d, J=8.8 Hz), 10.22 (1H, s, $D_2O$ exchange) Mass spectrum (EI-MS) m/z (%): 330 (100, $M^+$), 313(6), 301(26), 284 (36), 181(9), 151 (32) Elemental analysis: $C_{17}H_{14}O_5S$ Calculated; C:61.81, H:4.27 Found; C:61.49, H:4.24

EXAMPLE 72

2.22 g of 2-(4-hydroxyphenylthio)-5,7-dimethoxychromone obtained in Example 71 was placed in a reaction vessel, and then the atmosphere in the vessel was replaced by nitrogen. 25 ml of water-free methylene chloride was added, thus making a suspension. 25 ml of 0.8M boron tribromide in methylene chloride was added at −40° C. Subsequently, the mixture was stirred at −40 C. for 10 min., followed by stirring for 1 hour at room temperature. The solution thus reacted was poured into 300 ml of ice water, and impurities were given by filtration (and were then sufficiently washed with water), whereby yellow solids were obtained. This product was then subjected to recrystallization from acetone-n-hexane, so that 5-hydroxy-2-(4-hydroxyphenylthio)-7-methoxychromone, 1.57 g, was obtained as colorless acicular crystal.

Infrared absorption spectrum (IR, vmax $cm^{-1}$, KBr): 3164, 1660, 1590, 1494, 1436, 1336, 1286, 1198, 1166, 1130, 1110, 1040, 916, 860, 832, 800, 766, 686, 538, 524 Proton nuclear magnetic resonance spectrum (δppm in DMSO-$d_6$): 3.83 (3H, s), 5.51 (1H, s), 6.38 (1H, d, J=2.4 Hz), 6.59 (1H, d, l=2.4 Hz), 6.96 (2H, d, J=8.8 Hz), 7.52 (2H, d, J=8.8 Hz), 10.29 (1H, s, $D_2O$ exchange) 12.61 (1H, s, $D_2O$ exchange) Mass spectrum (EI-MS) m/z (%): 316 (100, $M^+$), 287 (13), 167 (53), 150 (30), 138 (10), 121 (12), 95 (10) Elemental analysis: $C_{16}H_{12}O_5S$ Calculated; C:60.75, H:3.82 Found; C:60.77, H:3.84

EXAMPLE 73

4.0 g of 4-hydroxy-5,7-dimethoxychromene-2-thione and 3.0 ml of 4-methoxybenzyl chloride were placed in a reaction vessel, and the atmosphere in the vessel was replaced by nitrogen. 80 ml water-free acetone was added, thus making a suspension. 3.0 ml of 4-methoxybenzyl chloride was added at room temperature, and the mixture was stirred overnight at room temperature. The solvent was distilled out under reduced pressure from the solution thus reacted, followed by addition of water. The product was extracted twice with chloroform (200 ml×2), and the chloroform layer was washed with saturated salt water and then dried over magnesium sulfate. The solvent was distilled out under reduced pressure, whereby gray solids were obtained. This product was subjected to recrystallization from acetone-n- hexane, whereby 4.12 g of 5,7-dimethoxy-2-(4-methoxybenzylthio)chromone with the following physicochemical properties was obtained as colorless prism crystal.

Melting point: 136°–139° C. Infrared absorption spectrum (IR, vmax cm$^{-1}$, KBr): 1644, 1612, 1590, 1564, 1510, 1462, 1420, 1314, 1246, 1204, 1162, 1124, 1094, 1018, 916, 824, 758, 594, 526 Proton nuclear magnetic resonance spectrum (δppm in DMSO-d$_6$): 3.72 (3H, s), 3.80 (3H, s), 3.87 (3H, s), 4.35 (2H, s), 6.09 (1H, s), 6.49 (1H, d, J=2.4 Hz), 6.71 (1H, d, J=2.4 Hz), 6.90 (2H, d, J=8.8 Hz), 7.35 (2H, d, J=8.8 Hz) Mass spectrum (EI-MS) m/z (%): 358 (35, M$^+$), 238 (6), 209 (6), 181 (14), 121 (100) Elemental analysis: C$_{19}$H$_{18}$O$_5$S Calculated; C:63.67, H:5.06 Found; C:63.66, H:5.05

EXAMPLE 74

2.5 g of 5,7-dimethoxy-2-(4-methoxybenzylthio) chromone obtained in Example 73 was placed in a reaction vessel, and then the atmosphere in the vessel was replaced by nitrogen. 26 ml of water-free methylene chloride was added, thus making a suspension. 26 ml of 0.8M boron tribromide in methylene chloride was added at −40° C. Subsequently, the mixture was stirred at −40 C. for 10 min., followed by stirring for 1 hour at room temperature. The solution thus reacted was poured into 300 ml of ice water, and impurities (sufficiently washed with water) were given by filtration in the form of orange solids. This product was then applied to flash column chromatography (ethyl acetate:n-hexane=2:3) and fractionated into 80 ml per fraction. Fractions Nos. 8 to 13 were combined and recrystallized from acetone-n-hexane, whereby 1.22 g of 5-hydroxy-2-(4-hydroxybenzylthio)-7-methoxychromone with the following physicochemical properties was obtained as colorless acicular crystal.

Melting point: 180°–183° C. Infrared absorption spectrum (IR, vmax cm$^{-1}$, KBr): 3276, 1666, 1592, 1514, 1492, 1440, 1336, 1232, 1202, 1166, 1126, 1110, 1044, 920, 864, 824, 798, 756, 690, 638, 562, 530 Proton nuclear magnetic resonance spectrum (δppm in DMSO-d$_6$): 3.85 (3H, s), 4.38 (2H, s), 6.34 (1H, s), 6.38 (1H, d, J=2.4 Hz), 6.68 (1H, d, J=2.4 Hz), 6.73 (2H, d, J=8.8 Hz), 7.26 (2H, d, J=8.8 Hz), 9.49 (1H, s, D$_2$O exchange), 12.73(1H, s, D$_2$O exchange) Mass spectrum (EI-IRIS) m/z (%): 330 (7, M$^+$), 224 (100), 195 (25), 167 (15), 138 (9), 107 (71) Elemental analysis: C$_{17}$H$_{14}$O$_5$S Calculated; C:61.81, H:4.27 Found; C:61.72, H:4.33

EXAMPLE 75

In the flash column chromatography in Example 74, Fractions Nos. 15 to 23 were combined and recrystallized from acetone-n-hexane, whereby 0.34 g of 5,7-dihydroxy-2-(4-hydroxybenzylthio)chromone was obtained as colorless fine acicular crystals.

Melting point: 222°–225° C. Infrared absorption spectrum (IR, vmax cm$^{-1}$, KBr): 3268, 1660, 1604, 1574, 1500, 1342, 1254, 1170, 1126, 1108, 924, 820 750 Proton nuclear magnetic resonance spectrum (δppm in DMSO-d$_6$): 4.36 (2H, s), 6.18 (1H, d, J=1.0 Hz), 6.27 (1H, s), 6.38 (1H, d, J=1.0 Hz), 6.72 (2H, d, J=8.3 Hz), 7.24 (2H, d, J=8.3 Hz), 9.48 (1H, s, D$_2$O exchange), 10.86 (1H, s, D$_2$O exchange), 12.71 (1H, s, D$_2$O exchange) Mass spectrum (EI-MS) m/z (%): 316 (80, M$^+$), 283 (43), 222 (35), 210 (68), 153 (100)

EXAMPLE 76

3.94 g of 5,7-dimethoxy-2-methylchromone obtained in the example was placed in a reaction vessel, and then the atmosphere in the vessel was replaced by nitrogen. 58 ml of water-free methylene chloride was added, and then 58 ml of 0.8M boron tribromide in methylene chloride was added at −40° C. Subsequently, the mixture was stirred at −40° C. for 30 min., followed by stirring for 30 min. at room temperature. The solution thus reacted was poured into 300 ml of ice water, and impurities were collected by filtration (and sufficiently washed with water) to give yellow solids. The filtrate was subjected to extraction with chloroform. The chloroform layer was washed with saturated salt water and dried over magnesium sulfate, and the solvent was distilled out under reduced pressure, whereby brown solids were obtained. The products thus obtained were applied to flash column chromatography (ethyl acetate:n-hexane=1:2) and fractionated into 150 ml per fraction. Fractions Nos. 7 to 28 were combined, to give 2.95 g of 5-hydroxy-7-methoxy-2-methylthiochromone with the following physicochemical properties was obtained.

This product was further subjected to recrystallization from acetone-n-hexane, thereby giving light yellow fine acicular crystals.

Melting points: 164°–166° C. Infrared absorption spectrum (IR, vmax cm$^{-1}$, KBr): 3080, 1654, 1614, 1506, 1434, 1382, 1320, 1304, 1264, 1216, 1162, 1132, 1108, 1032, 960, 916 844, 568 Proton nuclear magnetic resonance spectrum (δppm in CDCl$_3$): 2.53 (3H, s), 3.85 (3H, s), 6.04 (1H, s), 6.35 (2H, s), 12.66 (1H, s, D$_2$O exchange), Mass spectrum (EI-MS) m/z (%): 238 (100, M$^+$), 223 (19), 209 (32), 195 (12), 166 (22), 138 (21), 95(14), 69(18)

EXAMPLE 77

(1) 3.5 g of 5-hydroxy-7-methoxy-2-methylchromone obtained in Example 76 was placed into the reaction vessel, followed by addition of 70 ml chloroform. 3.38 g of m-chloroperbenzoic acid was added little by little over approx. 5 min. under stirring on ice. Then, the solution was stirred at room temperature for 2 hours. An aqueous saturated sodium bisulfite solution was added to the solution thus reacted. Following stirring over 10 min. at room temperature, the product was extracted with chloroform. The chloroform layer was washed with an aqueous saturated sodium bicarbonate solution and then with saturated salt water. The resulting solution was dried over magnesium sulfate, and the solvent was distilled out under reduced pressure, whereby yellow solids were obtained. The product was then recrystallized from chloroform-n-hexane, so that 5-hydroxy-7-methoxy-2-methylsulfinyl chromone, 3.07 g, was obtained as colorless acicular crystal.

Melting point: 194°–196° C. Infrared absorption spectrum (IR, vmax cm$^{-1}$, KBr): 3064, 1658, 1610, 1502, 1440, 1334, 1300, 1204, 1156, 1092, 1072, 1040, 966, 870, 824, 774, 674, 554 Proton nuclear magnetic resonance spectrum (δppm in DMSO-d$_6$): 3.02 (3H, s), 3.87 (3H, s), 6.48 (1H, d, J=2.4 Hz), 6.67 (1H, s), 6.75 (1H, d, J=2.4 Hz), 12.36 (1H, s, D$_2$O exchange) Mass spectrum (EI-MS) m/z (%): 254 (70, M$^+$), 238 (35), 211 (19), 179 (80), 167 (35), 135 (32), 78 (71), 63 (100)

(2) 2.70 g of 5-hydroxy-7-methoxy-2-methylsulfinyl chromone and 6.43 g of p-aminophenol were placed in a reaction vessel. The atmosphere in the vessel was replaced by nitrogen. 60 ml water-free dimethylformamide was added, and the mixture was stirred overnight at room temperature. The solution thus reacted was poured into 300 ml ice water, and impurities were collected by filtration (and washed sufficiently with water), so that gray solids were obtained. The solids were subjected to recrystallization from methanol, whereby 2.56 g of 5-hydroxy-2-(4-hydroxyanilino)-7-methoxychromone with the following physicochemical properties was obtained as colorless fine acicular crystal.

Melting point: more than 300° C. Infrared absorption spectrum (IR, vmax cm$^{-1}$, KBr): 392, 3232, 3124, 3064, 1656, 1600, 1542, 1498, 1338, 1266, 1244, 1210, 1158, 1126, 1088, 1038, 830, 806, 756, 686, 610 Proton nuclear magnetic resonance spectrum (δppm in DMSO-d$_6$): 3.81 (3H, s), 5.14 (1H, s), 6.27 (1H, d, J=2.0 Hz), 6.38 (1H, d, J=2.0 Hz), 6.82 (2H, d, J=8.8 Hz), 7.15 (2H, d, J=8.8 Hz), 9.55 (1H, s, D$_2$O exchange) 9.97 (1H, s, D$_2$O exchange) 13.85(1H, s, D$_2$O exchange) Mass spectrum (EI-MS) m/z (%): 299 (100, M$^+$), 270 (12), 180 (7), 167 (60), 133 (43) Elemental analysis: C$_{16}$H$_{13}$O$_5$N Calculated; C:64.21, H:4.38, N:4.68 Found; C:63.92, H:4.17, N:4.62

EXAMPLE 78

(1) Under cooling on ice, potassium hydride (0.5 ml of 35% mineral oil) was suspended in 2 ml THF. Then 2 ml THF solution of 126 mg (0.492 mmol)2'-hydroxy-4',6'-bis (methoxymethoxy)acetophenone and 130 mg (0.492 mmol) 18-crown-6 was added dropwise to the above suspension, followed by stirring for 1 hour. 0.89 ml (14.76 mmol) carbon disulfide was added to the solution, and the mixture was stirred for 20 hours at room temperature. After 0.5 ml methyl iodide was added, the mixture was stirred for 30 min. Subsequently, water was slowly added to the solution thus reacted. The product was extracted twice with ether, and the organic layer was washed with brine and dried over anhydrous sodium sulfate. The solvent was distilled out under reduced pressure. The resulting crude product was washed with hexane, so that 133.5 mg of 5,7-bis(methoxymethoxy)-2-methylthiochromone was obtained (yield: 87%).

Melting Point: 109°–110° C. IR (vmax$^{cm^{-1}}$, KBr) 1640, 1620, 1588, 1316, 152, 1126, 1092, 1074, 1036, 904 1H-NMR(δ$_{ppm}$, in CDCl$_3$): 6.73 (d, 2.5 Hz, 1H), 6.71 (d, 2.5 Hz, 1H), 6.04 (s, 1H), 5.31 (s, 2H), 5.22 (s, 2H), 3.55(s, 3H), 3.50 (s, 3H), 2.49 (s, 3H) MS (FAB): 313 (MH+) HRMS: C$_{14}$H$_{17}$O$_6$S Calculated; 313.07459 Found; 313.07433

(2) Under cooling on ice, 70 ml HCl-methanol was added to 70 ml of 9.47 g (30.35 mmol) 5,7-bis(methoxymethoxy)-2-methylthiochromone in THF. The mixture was stirred overnight at room temperature. Subsequently, water was added to the solution thus reacted. The product was extracted twice with ethyl acetate, and the organic layer was washed with brine and dried over anhydrous sodium sulfate. The solvent was distilled out under reduced pressure, whereby 6.88 g of 5,7-dihydroxy-2-methylthiochromone was obtained. This product was used without being purified in the following reaction.

Melting Point 244°–246° C. IR (vmax$^{cm^{-1}}$, KBr) 1650, 1610, 1582, 1564, 1498, 1354, 1346, 1164 $^1$H-NMR (δppm, in acetone-d$_6$): 12.82 (s, 1H), 9.70 (brs, 1H), 6.37 (d, 2.0 Hz, 1H), 6.23 (d, 2.0 Hz, 1H), 2.64 (s, 3H) MS (FAB): 225 (MH+) HRMS: C$_{10}$H$_9$O$_4$S Calculated; 225.02216 Found; 225.02406

(3) 1 ml of an aqueous solution of 82 mg (0.134 mmol) oxone was added dropwise to 1 ml of 30 mg (0.134 mmol) 5,7-dihydroxy-2-methylthiochromone in methanol. The mixture was stirred over 1 hour at room temperature. Subsequently, water was added to the solution thus reacted. The product was extracted twice with ethyl acetate, and the organic layer was washed with brine and dried over anhydrous sodium sulfate. The solvent was distilled out under reduced pressure, whereby 32 mg of 5,7-dihydroxy-2-methylsulfinylchromone (containing a small amount of sulfone) was obtained. This product was used without being purified in the following reaction.

$^1$H-NMR ppm (v$_{ppm}$ t in acetone-d$_6$): -12.46 (s, 1H), 6.64 (s, 1H), 6.49 (d, 2.4 Hz, 1H), 6.32 (d, 2.4 Hz, 1H), 3.03 (s, 3H) MS (FAB) 241 (MH+) HRMS: C$_{10}$H$_9$O$_5$S Calculated; 241.01856 Found; 241.01707

(4) A mixture consisting of 32 mg (0.134 mmol) 5,7-dihydroxy-2-methylsulfinylchromone, 20 mg (0.161 mmol) 4-hydroxybenzenethiol, 41 mg (0.295 mmol) potassium carbonate, and 2 ml acetone was stirred overnight at room temperature. The solution thus reacted was neutralized by addition of dilute hydrochloric acid. Subsequently, the product was extracted twice with ethyl acetate. The organic layer was washed with brine and dried over anhydrous sodium sulfate. The solvent was distilled out under reduced pressure. The resulting crude product was subjected to recrystallization from acetone-hexane, whereby 14.6 mg of 5,7-dihydroxy-2-(4-hydroxyphenylthio)chromone was obtained (yield: 36%).

Melting Point: 249°–251° C. IR (vmax$^{cm^{-1}}$, KBr) 3400, 1702, 1642, 1604, 1582, 1574, 1500, 1348, 1334, 1164, 830, $^1$H-NMR (δ$_{ppm}$, in acetone-d$_6$): 12.72 (s, 1H), 7.56 (d, 8.8 Hz, 2H), 7.05 (d, 8.8 Hz, 2H), 6.33 (d, 2.0 Hz, 1H), 6.23 (d, 2.0 Hz, 1H), 5.54 (s, 1H) MS (EI): 302 (M+), 153, 150 HRMS: C$_{15}$H$_{10}$O$_5$S Calculated; 302.02490 Found; 302.02526

EXAMPLE 79

(1) A mixture consisting of 6.88 g (30.35 mmol) 5,7-dihydroxy-2-methylthiochromone, 12.56 g (91.05 mmol) potassium carbonate, 6.07 ml (60.70 mmol) isopropyl iodide, and 150 ml DMF was stirred at 60° C. for 30 min. Subsequently, water was added to the solution. The product was extracted twice with ethyl acetate. The organic layer was washed with brine and dried over anhydrous sodium sulfate. The solvent was distilled out under reduced pressure. The resulting crude product was purified by flash column chromatography (hexane ethyl acetate=4:1), whereby 6.71 g of 5-hydroxy-7-isopropoxy-2-methylthiochromone was obtained (yield: 83%).

Melting Point : 119 120C IR (vmax$^{cm^{-1}}$, KBr) 1664,1592, 1498,1484,1430,1342,1322,1164,1132,1110 $^1$H-NMR (δ$_{ppm}$,in CDCl$_3$): 12.59 (s, 1H), 6.31 (s, 2H), 6.03 (s, 1H), 4,59 (m, 1H), 2.52 (s, 3H), 1.37 (d, 5.9 Hz, 6H) MS (FAB): 267 (M11+), 225 HRMS: C$_{13}$H$_{15}$O$_4$S Calculated; 267.06911 Found; 267.06964

(2) Under cooling on ice, 50 ml of 5.11 g (29.51 mmol) m-chloroperbenzoic acid in dichloromethane was added dropwise to 150 ml of 6.54 g (24.59 mmol) 5-hyderoxy-7-isopropoxy-2-methylthiochromone in dichloromethane. The mixture was stirred over 1 hour. Subsequently, an aqueous solution of sodium bicarbonate was added to the solution thus reacted. The product was extracted twice with chloroform, and the organic layer was washed with brine and dried over anhydrous sodium sulfate. The solvent was distilled out under reduced pressure, whereby 7.01 g of 5-hydroxy-7-isopropoxy-2-methylsulfinylchromone was obtained. This product was used without being purified in the following reaction.

IR (vmax$^{cm^{-1}}$, KBr): 1664, 1608, 1068 $^1$H-NMR(δ$_{ppm}$, in CDCl$_3$): 12.27 (s, 1H), 6.81 (s, 1H), 6.37 (s, 2H), 4.62 (m, 1H), 2.96 (m, 1H), 2.96 (s, 3H) 1,38(d, 6.4 Hz 6H)

(3) A mixture consisting of 7.01 g (24.59 mmol) 5-hydroxy-7-isopropoxy-2-methylsulfinylchromone, 3.72 g (29.51 mmol) 4-hydroxybenzenethiol, 4.07 g (29.51 mmol)

potassium carbonate, and 170 ml acetone was stirred over 1 hour at room temperature. The solution thus reacted was neutralized by addition of dilute hydrochloric acid. Subsequently, the product was extracted twice with chloroform. The organic layer was washed with brine and dried over anhydrous sodium sulfate. The solvent was distilled out under reduced pressure. The resulting crude product was subjected to recrystallization from ethanol-methanol, whereby 6.64 g of 5-hydroxy-2-(4-hydroxyphenylthio)-7-isopropoxychromone was obtained (yield: 78%).

Melting Point: 205°–207° C. IR (vmax$^{cm^{-1}}$, KBr) 3300, 1656, 1594, 1496, 1322 $^1$H-NMR ($\delta_{ppm}$, in CDCl$_3$): 12.26 (s, 1H), 7.97 (brs, 1H), 7.41 (d, 8.8 Hz, 2H), 6.87 (d, 8.8HZ, 2H), 6.36 (d, 2.4 Hz, 1H), 6.32 (d, 2.4 Hz, 1H): 5.59 (s, 1H), 4.61 (m, 1H) 1.37 (d, 5.9HZ, 6H) MS (EI): 344 (M+), 302 HRMS: C$_{18}$H$_{16}$O$_5$S Calculated; 344.07185 Found; 344.07170

EXAMPLE 80

(1) A mixture consisting of 354 mg (1.58 mmol) of 5,7-dihydroxy-2-methylthiochromone, 1.09 g (7.90 mmol) potassium carbonate, 0.79 ml (7.90 mmol) isopropyl iodide, and 20 ml acetone was refluxed overnight. Then, 2.95 ml (47.4 mmol) methyl iodide was added, and the mixture was further refluxed overnight. Water was added to the solution thus reacted. The product was extracted twice with ethyl acetate. The organic layer was washed with brine and dried over anhydrous sodium sulfate. The solvent was distilled out under reduced pressure. The resulting crude product was purified by flash column chromatography (hexane:ethyl acetate=1:3–1:6), whereby 228 mg of 7-isopropoxy-5-methoxy-2-methylthiochromone was obtained (yield: 52%).

Melting Point: 113°–114° C. IR (vmax$^{cm^{-1}}$, KBr):1 640, 1586, 1308, 1124 $^1$HNMR ($\delta_{ppm}$, in CDCl$_3$): 6.39 (d, 2.2 Hz, 1H), 6.32 (d, 2.2 Hz, 1H), 6.04 (s, 1H), 4.61 (m, 1H), 3.92 (s, 3H), 2.48 (s, 3H), 1.39 (d, 6.1 Hz , 6H), MS (FAB): 2.81(MH+), 239 HRMS: C$_{14}$H$_{17}$O$_4$S Calculated; 281.08476 Found; 281.08588

(2) 2 ml of an aqueous solution of 347 mg (0.564 mmol) oxone was added dropwise to 4 ml of 158 mg (0.564 mmol) 7-isopropoxy-5-methoxy-2-methylthiochromone in methanol. The mixture was stirred for 30 min. Subsequently, water was added to the solution thus reacted. The product was extracted twice with ethyl acetate. The organic layer was washed with brine and dried over anhydrous sodium sulfate. The solvent was distilled out under reduced pressure, whereby 147 mg of 7 isopropoxy-5-methoxy-2-methylsulfinylchromone (containing a little amount of sulfone) was obtained. This product was used for the following reaction without purification.

$^1$H-NMR ($v_{ppm}$, in CDCl$_3$): 6.73 (s, 1H), 6.45 (d, 2.2 Hz, 1H), 6.38 (d, 2.2 Hz, 1H), 4.63 (m, 1H), 3.94 (s, 3H0, 2.95 (s, 3H), 1.40 (d, 6.1 Hz, 6H), (3) A mixture consisting of 146 mg (0.493 mmol) 7-isopropoxy-5-methoxy-2-methylsulfinylchromone, 93 mg (0.740 mmol) 4-hydroxybensenethiol, 102 mg (0.740 mmol) potassium carbonate, and 6 ml acetone was stirred over 2 hours at room temperature. The solution thus reacted was neutralized with dilute hydrochloric acid. The product was extracted twice with ethyl acetate. The organic layer was washed with brine and dried over anhydrous sodium sulfate. The solvent was distilled out under reduced pressure. The resulting crude product was subjected to recrystallization from acetone-methanol, whereby 102 mg of 2-(4-hydroxyphenylthio)-7-isopropoxy-5-methoxychromone was obtained (yield: 57%).

Melting Point: 263°–265° C. IR (vmax$^{cm^{-1}}$, KBr): 3200, 1626, 1598, 1582, 1320, 1126 $^1$H-NMR ($\delta_{ppm}$, in DMSO-d$_6$): 7.48 (d, 8.5 Hz, 2H), 6.93 (d, 8.5 Hz, 2H), 6.60 (d, 2.0 Hz, 1H), 6.42 (d, 2.0 Hz, 1H), 5.32 (s, 1H), 4.78 (m, 1H), 3.78 (s, 3H).

EXAMPLE 81

(1) Corn starch 34.5 g
(2) Magnesium stearate 50 g
(3) Carboxylmethyl cellulose calcium 5 g
(4) Light silicic anhydride 0.5 g
(5) Compound obtained in Example 39 10 g
Total 100 g According to the above formulation, ingredients (1) to (5) were uniformly mixed, then compression-molded using a compression molding machine, and crushed using a crusher, followed by being screened, whereby granules were given.

1 g of the granules thus prepared contains 100 mg of the compound obtained in Example 39. 2–5 g granules are orally administered per day into an adult at suitable intervals.

EXAMPLE 82

(1) Crystalline cellulose 55 g
(2) 10% hydroxypropyl cellulose in ethanol 35 g
(3) Compound obtained in Example 57 10 g
Total 100 g According to the above formulation, ingredients (1) to (3) were uniformly mixed, then kneaded, and formed into granules by an extrusion granulating machine. The granules were then dried and ground, followed by being screened, thereby giving granules. 1 g of the granules thus prepared contains 100 mg of the compound obtained in EXAMPLE 57. 2–5 g granules are orally administered per day into an adult at suitable intervals.

EXAMPLE 83

(1) Corn starch 84.5 g
(2) Light silicic anhydride 0.5 g
(3) Compound obtained in Example 71 10 g
Total 100 g According to the above formulation, the compounds (1) to (3) were uniformly mixed, and 200 mg of the mixture was introduced into No. 2 capsule.

1 capsule thus prepared contains 20 mg of the compound obtained in Example 71. 10–25 capsules are orally administered per day into an adult at suitable intervals.

EXAMPLE 84

(1) Soybean oil 5 g
(2) Distilled water for injection 89.5 g
(3) Phospholipids derived from soybean 2.5 g
(4) Glycerin 2 g
(5) Compound obtained in Example 76 1 g
Total 100 g According to the above formulation, ingredient (5) was dissolved in ingredients (1) and (3). A solution of ingredients (2) and (4) was added to the mixture, whereby an emulsion for use in injection was prepared.

Utility Possibility in Industry

As stated, the present chromone derivatives and aldose reductase inhibitor exhibit superior inhititory action on aldose reductase and are useful for the treatment of various complications of diseases in diabetes, such as cataract, retinosis, keratopathy, nephrosis, and peripheral nervous system disorder.

What is claimed is:

1. A method for inhibiting aldose reductase comprising: employing a chromone derivative or a pharmaceutically acceptable salt thereof represented by Formula (I):

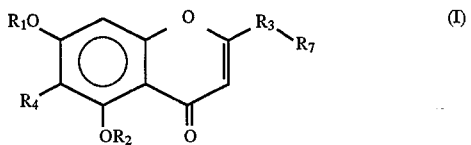

wherein $R_1$ and $R_2$ are selected from the group consisting of a hydrogen atom, a lower alkyl group, a lower alkenyl group, an aliphatic acyl group and an aromatic acyl group; $R_3$ represents a sulfur atom; $R_4$ is selected from the group consisting of a hydrogen atom and a lower alkoxy group; $R_7$ is selected from the group consisting of a phenyl, benzyl, and a nitrogen-containing heterocyclic group selected from the group consisting of pyridyl, benzimidazolyl, benzthiazolyl, thiazolynyl and thiadiazolyl, substituted or unsubstituted, wherein substituents are selected from the group consisting of $C_{1-6}$ alkyl group, a halogen atom, an amino, hydroxy, nitro, carboxyl, hydroxymethyl, methylenedioxy, $C_{1-6}$ alkoxy, $C_{2-6}$ alkenyloxy, $C_{1-6}$ alkoxycarbonyl, tert-butyldimethylsilyloxy, a glycyloxy group, a β-aspartyloxy group, a 4-(4-methylpiperazinomethyl)benzoyloxy group and a benzoyloxy group.

2. A method according to claim 1, wherein $R_7$ is a substituted phenyl group wherein substituents are selected from the group consisting of $C_{1-6}$ alkyl group, a halogen atom, an amino, hydroxy, nitro, carboxyl, hydroxymethyl, methylenedioxy, $C_{1-6}$ alkoxy, $C_{2-6}$ alkenyloxy, $C_{1-6}$ alkoxycarbonyl, tert-butyldimethylsilyloxy, a glycyloxy group, a β-aspartyloxy group, a 4-(4-methylpiperazinomethyl)benzoyloxy group and a benzoyloxy group.

3. A method according to claim 1, wherein $R_1$ is selected from the group consisting of ethyl and a branched alkyl group represented by Formula (II):

wherein $R_8$ and $R_9$ are each selected from the group consisting of methyl and ethyl; and $R_2$ is selected from the group consisting of a hydrogen atom, methyl, ethyl and a branched alkyl group represented by Formula (II).

4. A method according to claim 1, wherein $R_1$ is selected from the group consisting of ethyl and a branched alkyl group represented by Formula (II):

wherein $R_8$ and $R_9$ are each selected from the group consisting of methyl and ethyl; and $R_2$ is selected from the group consisting of a hydrogen atom, methyl, ethyl and a branched alkyl group represented by Formula (II) and $R_7$ represents a phenyl group substituted by a hydroxy group.

5. A method for inhibiting aldose reductase according to claim 1 comprising employing a chromone derivative or a pharmaceutically acceptable salt thereof selected from the group consisting of 5,7-diisopropoxy-2-(4-hydroxyphenylthio)-6-methoxychromone, 5,7-diethoxy-2-(4-hydroxyphenylthio)-6-methoxychromone, 5,7-di-s-butoxy-2-(4-hydroxyphenylthio)-6-methoxychromone, 7-s-butoxy-2-(4-hydroxyphenylthio)-5-isopropoxy-6-methoxychromone, 5-ethoxy-2-(4-hydroxyphenylthio)-7-isopropoxy-6-methoxychromone, 5-hydroxy-2-(4-hydroxyphenylthio)-7-isopropoxy-6-methoxychromone, 5,6-dimethoxy-2-(4-hydroxyphenylthio)-7-isopropoxychromone, 7-s-butoxy-5,6-dimethoxy-2-(4-hydroxyphenylthio)chromone, 5,6-dimethoxy-7-(1-ethylpropoxy)-2-(4-hydroxyphenylthio)chromone and 5,7-diisopropoxy-2-(4-hydroxyphenylthio)chromone.

6. A method according to claim 1, wherein the chromone derivative or pharmaceutically acceptable salt thereof is employed by administering the chromone derivative or pharmaceutically acceptable salt to a patient with diabetes.

7. A method according to claim 6, comprising the further step of treating a symptom of diabetes.

8. A method for inhibiting aldose reductase comprising: employing a chromone derivative or a pharmaceutically acceptable salt thereof represented by Formula (I):

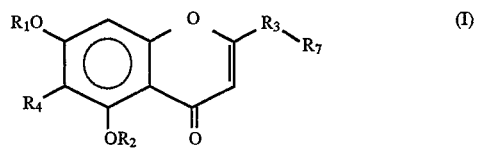

wherein $R_1$ and $R_2$ are selected from the group consisting of a hydrogen atom, a lower alkyl group, a lower alkenyl group, and an acyl group; $R_3$ represents a sulfur atom; $R_4$ is selected from the group consisting of a hydrogen atom and a lower alkoxy group; $R_7$ represents a phenyl group which is substituted by a hydroxy group, a glycyloxy group, β-aspartyloxy or a 4-(4-methylpiperazinomethyl) benzoyloxy group.

9. A method according to claim 8, wherein $R_1$ is selected from the group consisting of ethyl and a branched alkyl group represented by Formula (II):

wherein $R_8$ and $R_9$ are each selected from the group consisting of methyl and ethyl; and $R_2$ is selected from the group consisting of a hydrogen atom, methyl, ethyl and a branched alkyl group represented by Formula (II).

10. A method for inhibiting aldose reductase according to claim 8 comprising: employing a pharmaceutically acceptable acid addition salt of compound of Formula (I) wherein $R_7$ represents a phenyl group which is substituted by a glycyloxy group, β-aspartyloxy, or a 4-(4-methylpiperazinomethyl)benzoyloxy group.

11. A method according to claim 8, wherein the chromone derivative or pharmaceutically acceptable salt thereof is employed by administering the chromone derivative or pharmaceutically acceptable salt to a patient with diabetes.

12. A method according to claim 11, comprising the further step of treating a symptom of diabetes.

13. A method for inhibiting aldose reductase according to claim 1 comprising employing a chromone derivative or a pharmaceutically acceptable acid addition salt of a compound of Formula (I) wherein $R_7$ represents a phenyl group which is substituted by a glycyloxy group, a β-aspartyloxy group or a 4-(4-methylpiperazinomethyl)benzoyloxy group.

14. A method for inhibiting aldose reductase according to claim 1 comprising employing a chromone derivative or a pharmaceutically acceptable salt thereof selected from the group consisting of 5,6-dimethoxy-2-(4-glycyloxyphenylthio)-7-isopropoxychromone hydrochloride, 5-ethoxy-2-(4-glycyloxyphenylthio)-7-isopropoxy-6-methoxychromone hydrochloride, 7-(1-ethylpropoxy)-5,6-dimethoxy-2-(4-glycyloxyphenylthio) chromone hydrochloride, 2-(4-β-aspartyloxyphenylthio)-5-ethoxy-7-isopropoxy-6-methoxychromone hydrochloride, 5,6-dimethoxy-7-(1-ethylpropoxy)-2-{4-[4-(4-methylpiperazinomethyl)benzoyloxy]phenylthio}chromone dihydrochloride and 7-(1-ethylpropoxy)-5-hydroxy-2-{4-[4-(4-methylpiperazinomethyl)benzoyloxy]phenylthio}-6-methoxychromone dihydrochloride.

15. A method according to claim 6, comprising the further step of preventing a symptom of diabetes.

16. A method according to claim 11, comprising the further step of preventing a symptom of diabetes.

* * * * *